(12) United States Patent
Nakagawa et al.

(10) Patent No.: US 8,399,621 B2
(45) Date of Patent: Mar. 19, 2013

(54) ANTI-CD4 ANTIBODY

(75) Inventors: Tomoaki Nakagawa, Tokyo (JP); Sayaka Hori, Tokyo (JP); Rinpei Niwa, Tokyo (JP); Tsuguo Kubota, Tokyo (JP); Kazuhiro Masuda, Tokyo (JP); Kazuyasu Nakamura, Tokyo (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 307 days.

(21) Appl. No.: 12/647,698

(22) Filed: Dec. 28, 2009

(65) Prior Publication Data

US 2010/0310573 A1  Dec. 9, 2010

Related U.S. Application Data

(60) Provisional application No. 61/141,393, filed on Dec. 30, 2008.

(30) Foreign Application Priority Data

Dec. 26, 2008  (JP) ................ P2008-331904

(51) Int. Cl.
    C07K 16/00  (2006.01)
(52) U.S. Cl. .................. 530/387.1; 424/144.1
(58) Field of Classification Search .......... None
    See application file for complete search history.

(56) References Cited

U.S. PATENT DOCUMENTS

| 7,037,496 | B2* | 5/2006 | Ghrayeb et al. ........... 424/133.1 |
| 7,214,775 | B2 | 5/2007 | Hanai et al. |
| 2006/0183195 | A1 | 8/2006 | Lonberg et al. |
| 2007/0148165 | A1 | 6/2007 | Shitara et al. |

FOREIGN PATENT DOCUMENTS

| WO | 97/09351 A1 | 3/1997 |
| WO | 97/13852 A1 | 4/1997 |
| WO | 2007/009469 A2 | 1/2007 |

OTHER PUBLICATIONS

Carter (Nature Reviews, Immunology, vol. 6, May 2006, p. 343-357).*
Newman, et al., "'Primatization' of Recombinant Antibodies for Immunotherapy of Human Diseases: A Macaque/Human Chimeric Antibody Against Human CD4", Biotechnology, Nov. 1992, p. 1455-1460, vol. 10, Nature Publishing Company.
Reinherz, et al., "Separation of functional subsets of human T cells by a monoclonal antibody", Immunology, Proc. Natl. Acad. Sci. USA, Aug. 1979, pp. 4061-4065, vol. 76, No. 8.
Kim, et al., "Clinical efficacy of zanolimumab (HuMax-CD4): two phase 2 studies in refractory cutaneous T-cell lymphoma", Blood, Jun. 1, 2007, pp. 4655-4662, vol. 109 No. 11, doi:10.1182/blood-2006-12-062877.
Kon, et al., "Randomised, dose-ranging, placebo-controlled study of chimeric antibody to CD4 (keliximab) in chronic severe asthma", The Lancet, Oct. 3, 1998, pp. 1109-1113, vol. 352.
Anderson, et al., "A Primatized MAb to Human CD4 Causes Receptor Modulation without Marked Reduction in CD4+ T Cells in Chimpanzees: In Vitro and in Vivo Characterization of a MAb (IDEC-CE9. 1) to Human CD4", Clinical Immunology and Immunopathology, Jul. 1997, pp. 73-84, vol. 84, No. 1, Article No. II974363.
Rider, et al., "A Human CD4 Monoclonal Antibody for the Treatment of T-Cell Lymphoma Combines Inhibition of T-Cell Signaling by a Dual Mechanism with Potent Fc-Dependent Effector Activity", Cancer Research, Oct. 15, 2007, pp. 9945-9953, vol. 67 (20), DOI:10.1158/0008-5472.CAN-07-1148.
Reddy, et al., "Elimination of Fc Receptor-Dependent Effector Functions of a Modified IgG4 Monoclonal Antibody to Human CD4", BioLegend Expanding Brilliance, The Journal of Immunology, 2000, pp. 1925-1933, vol. 164, The American Association of Immunologists, Inc.
Merkenschlarger, et al., "Functional Epitope Analysis of the Human CD4 Molecule, The MHC Class II-Dependent Activation of Resting T Cells Is Inhibited by Monoclonal Antibodies to CD4 Regardless whether or Not They Recognize Epitopes Involved in the Binding of MHC Class II or HIV gp120", The Journal of Immunology, Nov. 1, 1990, pp. 2839-2845, vol. 145, No. 9, The American Association of Immunologists.
Troadec, et al., "Biological activities on T lymphocytes of a baculovirus-expressed chimeric recombinant IgG1 antibody with specificity for the CDR3-like loop on the D1 domain of the CD4 molecule", Clinical Immunology, 2006, pp. 38-50, vol. 119.
Ragupathi, et al., "Antibodies against Tumor Cell Glycolipids and Proteins, but Not Mucins, Mediate Complement-Dependent Cytotoxicity", The Journal of Immunology, 2005, pp. 5706-5712, vol. 174, The American Association of Immunologists, Inc.
Natsume, et al., "Engineered Antibodies of IgG1/IgG3 Mixed Isotype with Enhanced Cytotoxic Activities", Cancer Research, May 15, 2008, pp. 3863-3872, vol. 68 (10), DOI:10.1158/0008-5472. CAN-07-6297.
International Searching Authority, International Search Report for PCT/JP2009/071681 dated Feb. 2, 2010 [PCT/ISA/210].
European Patent Office, Search Report dated Dec. 19, 2012 issued in counterpart European Application No. 09835062.2.
Troadec, Samuel, et al., "In Vitro Antitumoral Activity of Baculovirus-expressed Chimeric Recombinant Anti-CD4 Antibody 13B8.2 on T-cell Lymphomas," Journal of Immunotherapy, 2007, 30(2): 190-202.
Choy, Ernest H. S., et al., "Chimaeric anti-CD4 monoclonal antibody cross-linked by monocyte Fc gamma receptor mediates apoptosis of human CD4 lymphocytes," European Journal of Immunology, 1993, 23(10): 2676-2681.

* cited by examiner

Primary Examiner — Laura B Goddard
Assistant Examiner — Meera Natarajan
(74) Attorney, Agent, or Firm — Sughrue Mion, PLLC

(57) ABSTRACT

An anti-CD4 antibody which binds to CD4, has a high affinity and has a high effector activity, such as an antibody-dependent cellular cytotoxicity (ADCC activity) or complement-dependent cellular cytotoxicity (CDC activity), is required for a disease relating to a CD4-expressing cell.
The present invention can provide a monoclonal antibody or an antibody fragment thereof, which binds to a CD4 extracellular region with high affinity and also exhibits a high ADCC activity or a high CDC activity; a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent using the antibody or the antibody fragment thereof or a diagnostic agent using the antibody or the antibody fragment thereof.

11 Claims, 15 Drawing Sheets

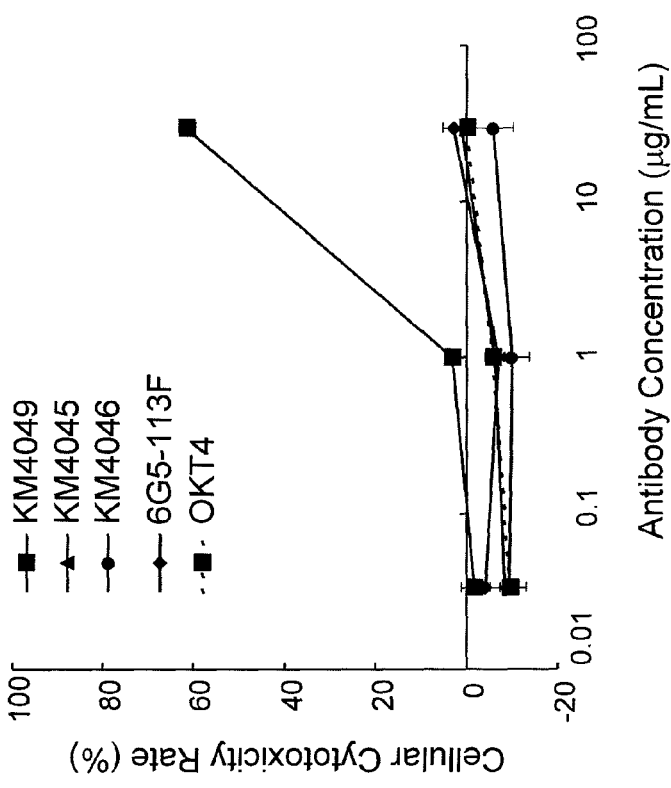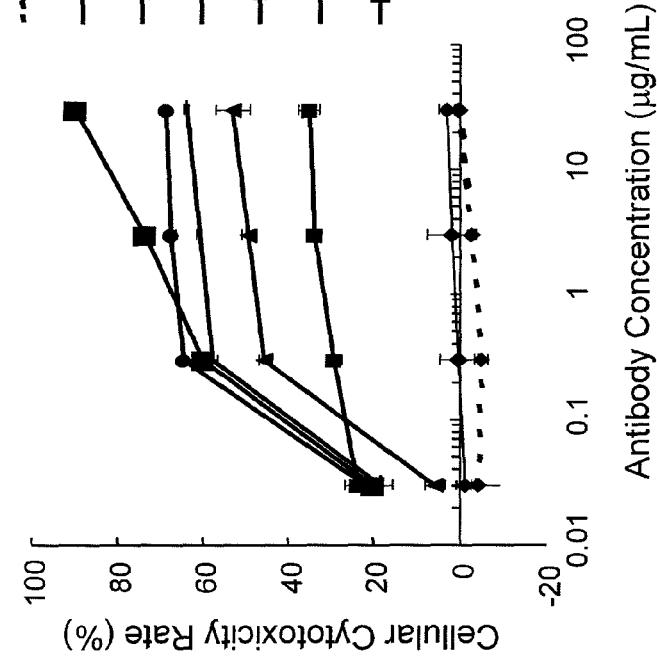
Fig. 10 (A)
Fig. 10 (B)

SEQUENCE LISTING

<160> NUMBER OF SEQ ID NOS: 102

<210> SEQ ID NO 1
<211> LENGTH: 458
<212> TYPE: PRT
<213> ORGANISM: Homo sapiens

<400> SEQUENCE: 1

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
                35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu

```
                      165                 170                 175
Gln Asp Ser Gly Thr Trp Thr Cys Thr Val Leu Gln Asn Gln Lys Lys
                180                 185                 190

Val Glu Phe Lys Ile Asp Ile Val Leu Ala Phe Gln Lys Ala Ser
            195                 200                 205

Ser Ile Val Tyr Lys Lys Glu Gly Glu Gln Val Glu Phe Ser Phe Pro
        210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
        290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
450                 455

<210> SEQ ID NO 2
<211> LENGTH: 1377
<212> TYPE: DNA
<213> ORGANISM: Homo sapiens

<400> SEQUENCE: 2
atgaaccggg gagtcccttt taggcacttg cttctggtgc tgcaactggc gctcctccca      60
gcagccactc agggaaagaa agtggtgctg gcaaaaaag gggatacagt ggaactgacc     120
tgtacagctt cccagaagaa gagcatacaa ttccactgga aaaactccaa ccagataaag     180
attctgggaa atcagggctc cttcttaact aaaggtccat ccaagctgaa tgatcgcgct     240
gactcaagaa gaagcctttg ggaccaagga aactttcccc tgatcatcaa gaatcttaag     300
atagaagact cagatactta catctgtgaa gtggaggacc agaaggagga ggtgcaattg     360
ctagtgttcg gattgactgc caactctgac acccacctgc ttcaggggca gagcctgacc     420
ctgaccttgg agccccccc tggtagtagc ccctcagtgc aatgtaggag tccaagggt     480 aaaaacatac agggggggaa gaccctctcc gtgtctcagc tggagctcca ggatagtggc     540
```

```
acctggacat gcactgtctt gcagaaccag aagaaggtgg agttcaaaat agacatcgtg    600
gtgctagctt tccagaaggc ctccagcata gtctataaga aagaggggga acaggtggag    660
ttctccttcc cactcgcctt tacagttgaa aagctgacgg gcagtggcga gctgtggtgg    720
caggcggaga gggcttcctc ctccaagtct tggatcacct ttgacctgaa gaacaaggaa    780
gtgtctgtaa acgggttac ccaggaccct aagctccaga tgggcaagaa gctcccgctc    840
cacctcaccc tgccccaggc cttgcctcag tatgctggct ctggaaacct caccctggcc    900
cttgaagcga aaacaggaaa gttgcatcag gaagtgaacc tggtggtgat gagagccact    960
cagctccaga aaatttgac ctgtgaggtg tggggaccca cctcccctaa gctgatgctg    1020
agcttgaaac tggagaacaa ggaggcaaag gtctcgaagc gggagaaggc ggtgtgggtg    1080
ctgaaccctg aggcggggat gtggcagtgt ctgctgagtg actcgggaca ggtcctgctg    1140
gaatccaaca tcaaggttct gcccacatgg tccaccccgg tgcagccaat ggccctgatt    1200
gtgctggggg gcgtcgccgg cctcctgctt ttcattgggc taggcatctt cttctgtgtc    1260
aggtgccggc accgaaggcg ccaagcagag cggatgtctc agatcaagag actcctcagt    1320
gagaagaaga cctgccagtg ccctcaccgg tttcagaaga catgtagccc catttga    1377

<210> SEQ ID NO 3
<211> LENGTH: 29
<212> TYPE: DNA
<213> ORGANISM: Artificial sequence
<220> FEATURE:
<223> OTHER INFORMATION: Description of artificial sequence:
      rat IgG1 specific primer

<400> SEQUENCE: 3
gtacatatac aaggcttgca atcacctcc                                      29

<210> SEQ ID NO 4
<211> LENGTH: 26
<212> TYPE: DNA
<213> ORGANISM: Artificial sequence
<220> FEATURE:
<223> OTHER INFORMATION: Description of artificial sequence:
      rat IgG2a specific primer

<400> SEQUENCE: 4
ccacaaggat tgcattccct tggcac                                         26

<210> SEQ ID NO 5
<211> LENGTH: 28
<212> TYPE: DNA
<213> ORGANISM: Artificial sequence
<220> FEATURE:
<223> OTHER INFORMATION: Description of artificial sequence:
      rat IgG2b specific primer

<400> SEQUENCE: 5
gggcatgtag ggcatttgtg tccaatgc                                       28

<210> SEQ ID NO 6
<211> LENGTH: 29
<212> TYPE: DNA
<213> ORGANISM: Artificial sequence
<220> FEATURE:
<223> OTHER INFORMATION: Description of artificial sequence:
      rat IgG kapper specific primer

<400> SEQUENCE: 6
cctgttgaag ctcttgacga cgggtgagg                                      29
```

<210> SEQ ID NO 7
<211> LENGTH: 417
<212> TYPE: DNA
<213> ORGANISM: Rattus norvegicus

<400> SEQUENCE: 7

| | | | | | |
|---|---|---|---|---|---|
| atggacatca | ggctcagctt | ggcttcctt | gtccttttca | taaaaggtgt | ccagtgtgag | 60 |
| gtgcaactgg | tagagtctgg | gggcggttta | gtgcagcctg | aaggtccat | gaaactctcc | 120 |
| tgtgcagcct | caggattcac | tttcagtaac | tatggcatgg | cctgggtccg | ccaggctcca | 180 |
| acgaaggggc | tggagtgggt | tgcaaccatt | agttatgatg | aagtatcac | ttattatcga | 240 |
| gactccgtga | agggccgatt | cactatctcc | agagatcatg | caaaaagcac | cctatacctg | 300 |
| caaatgaaca | gtctgaggtc | tgaggacacg | gccacttatt | actgtacaag | agaggaacaa | 360 |
| tatagcagct | ggtactttga | cttctggggc | ccaggaataa | tggtcaccgt | gtcctca | 417 |

<210> SEQ ID NO 8
<211> LENGTH: 429
<212> TYPE: DNA
<213> ORGANISM: Rattus norvegicus

<400> SEQUENCE: 8

| | | | | | |
|---|---|---|---|---|---|
| atgaatttca | gcaacacctt | ggttttcctt | ttgtttcttt | taaaaggtat | cctgtgtgag | 60 |
| gtgcagctgg | aggagtctgg | aggaggctta | gtgcagcctg | aaggtccct | gaaactctcc | 120 |
| tgtttagcct | ctggattcac | tttcagtaac | tatggaatga | actggattcg | ccaggctcca | 180 |
| gggaagggac | tggagtgggt | tgcatctatt | agtggtagta | gcacttacat | ctactatgca | 240 |
| gacacagtga | agggccgatt | caccatctcc | agagaaaatg | ccgagaacac | cctttacctg | 300 |
| caaatgacca | gtctgaggtc | tgaagacact | gccttgtatt | actgtgctag | agagggtct | 360 |
| tctacggatc | gttactacga | ggtttcgttt | gcctactggg | gccaaggcac | tctggtcact | 420 |
| gtctcttca | | | | | | 429 |

<210> SEQ ID NO 9
<211> LENGTH: 417
<212> TYPE: DNA
<213> ORGANISM: Rattus norvegicus

<400> SEQUENCE: 9

| | | | | | |
|---|---|---|---|---|---|
| atgggatgga | tctgtatcat | ctttcttgtg | gcaacagcta | caggtgtcca | ctcccaggtc | 60 |
| aagctgctgc | agtctggggc | tgcactggtg | aagcctggag | cctctgtgaa | gatgtcttgc | 120 |
| aaagcttctg | gttatacatt | cactgactac | tgggtgcact | gggtgaagca | gagtcatgga | 180 |
| aagagccttg | agtggattgg | ggaaatttat | cctaataata | atactactaa | cttcaatgaa | 240 |
| aaattcaagg | gcaaggccac | attgactgta | gacaaattca | ccagcacagc | ctacatggag | 300 |
| ctcagcagat | tgacatctga | ggactctgca | atctattact | gtacaagagg | aactgtatat | 360 |
| tacggattag | gctactttga | tcactggggc | caaggagtca | tggtcacagt | ctcttca | 417 |

<210> SEQ ID NO 10
<211> LENGTH: 414
<212> TYPE: DNA
<213> ORGANISM: Rattus norvegicus

<400> SEQUENCE: 10

| | | | | | |
|---|---|---|---|---|---|
| atggctgtcc | tggtgctgtt | gctctgcctg | ttgatatttc | caagctgtgt | cctgtcccaa | 60 |
| gtgcaactaa | aggagtcagg | acctggtctg | gtacagccat | cacagaccct | gtctctcacc | 120 |

```
tgcactgtct ctgggttatc attaaccagc aatagtgtaa gctggattcg gcagcctcca      180
ggaaagggtc tggagtggat gggaataata tggagtaatg gagacacaga ttataattca      240
gctatcaaat cccgactgag catcagcagg gacacctcga agagccaagt tttcttaaag      300
atgaacagtc tgcaaactga agacacagcc atgtacttct gtgccaatcc ttattatggg      360
tataacttcc cctttgatta ctggggccaa ggagtcatgg tcacagtctc ctca            414
```

<210> SEQ ID NO 11
<211> LENGTH: 414
<212> TYPE: DNA
<213> ORGANISM: Rattus norvegicus

<400> SEQUENCE: 11

```
atggctgtcc tggtgctgtt gctctgcctg ttgatatttc caagctgtgt cctgtcccaa       60
gtgcaactaa aggagtcagg gcctggtctg gtacagccat cacagaccct gtctctcacc      120
tgcactgtct ctgggtcatc tttaaccagc aatagtgtaa gctggattcg gcagcctcca      180
ggaaagggtc tggagtggat gggagtaatt tggagtaatg gagacgcaga ttataattca      240
gctatcaaat cccgactgag catcagcagg gacacctcga agagccaagt tttcttaaag      300
atgaacagtc tgcaaactga agacacagcc atgtacttct gtgccagtcc ttactatggg      360
tattacttcc cctttgatta ctggggccaa ggagtcatgg tcacagtctc ctca            414
```

<210> SEQ ID NO 12
<211> LENGTH: 139
<212> TYPE: PRT
<213> ORGANISM: Rattus norvegicus

<400> SEQUENCE: 12

```
Met Asp Ile Arg Leu Ser Leu Ala Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Arg Ser Met Lys Leu Ser Cys Ala Ala Ser Gly Phe Thr Phe
        35                  40                  45

Ser Asn Tyr Gly Met Ala Trp Val Arg Gln Ala Pro Thr Lys Gly Leu
    50                  55                  60

Glu Trp Val Ala Thr Ile Ser Tyr Asp Gly Ser Ile Thr Tyr Tyr Arg
65                  70                  75                  80

Asp Ser Val Lys Gly Arg Phe Thr Ile Ser Arg Asp His Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Glu Glu Gln Tyr Ser Ser Trp Tyr Phe Asp Phe
        115                 120                 125

Trp Gly Pro Gly Ile Met Val Thr Val Ser Ser
    130                 135
```

<210> SEQ ID NO 13
<211> LENGTH: 143
<212> TYPE: PRT
<213> ORGANISM: Rattus norvegicus

<400> SEQUENCE: 13

```
Met Asn Phe Ser Asn Thr Leu Val Phe Leu Leu Phe Leu Leu Lys Gly
1               5                   10                  15

Ile Leu Cys Glu Val Gln Leu Glu Glu Ser Gly Gly Gly Leu Val Gln
```

```
                       20                   25                   30
Pro Gly Arg Ser Leu Lys Leu Ser Cys Leu Ala Ser Gly Phe Thr Phe
            35                   40                   45

Ser Asn Tyr Gly Met Asn Trp Ile Arg Gln Ala Pro Gly Lys Gly Leu
        50                   55                   60

Glu Trp Val Ala Ser Ile Ser Gly Ser Ser Thr Tyr Ile Tyr Tyr Ala
65                   70                   75                   80

Asp Thr Val Lys Gly Arg Phe Thr Ile Ser Arg Glu Asn Ala Glu Asn
                85                   90                   95

Thr Leu Tyr Leu Gln Met Thr Ser Leu Arg Ser Glu Asp Thr Ala Leu
            100                  105                  110

Tyr Tyr Cys Ala Arg Glu Gly Ser Ser Thr Asp Arg Tyr Tyr Glu Val
        115                  120                  125

Ser Phe Ala Tyr Trp Gly Gln Gly Thr Leu Val Thr Val Ser Ser
    130                  135                  140

<210> SEQ ID NO 14
<211> LENGTH: 139
<212> TYPE: PRT
<213> ORGANISM: Rattus norvegicus

<400> SEQUENCE: 14

Met Gly Trp Ile Cys Ile Ile Phe Leu Val Ala Thr Ala Thr Gly Val
1               5                   10                  15

His Ser Gln Val Lys Leu Leu Gln Ser Gly Ala Ala Leu Val Lys Pro
            20                  25                  30

Gly Ala Ser Val Lys Met Ser Cys Lys Ala Ser Gly Tyr Thr Phe Thr
        35                  40                  45

Asp Tyr Trp Val His Trp Val Lys Gln Ser His Gly Lys Ser Leu Glu
    50                  55                  60

Trp Ile Gly Glu Ile Tyr Pro Asn Asn Asn Thr Thr Asn Phe Asn Glu
65              70                  75                  80

Lys Phe Lys Gly Lys Ala Thr Leu Thr Val Asp Lys Phe Ser Thr
            85                  90                  95

Ala Tyr Met Glu Leu Ser Arg Leu Thr Ser Glu Asp Ser Ala Ile Tyr
        100                 105                 110

Tyr Cys Thr Arg Gly Thr Val Tyr Tyr Gly Leu Gly Tyr Phe Asp His
    115                 120                 125

Trp Gly Gln Gly Val Met Val Thr Val Ser Ser
    130                 135

<210> SEQ ID NO 15
<211> LENGTH: 138
<212> TYPE: PRT
<213> ORGANISM: Rattus norvegicus

<400> SEQUENCE: 15

Met Ala Val Leu Val Leu Leu Leu Cys Leu Leu Ile Phe Pro Ser Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Leu Ser Leu
        35                  40                  45

Thr Ser Asn Ser Val Ser Trp Ile Arg Gln Pro Pro Gly Lys Gly Leu
    50                  55                  60

Glu Trp Met Gly Ile Ile Trp Ser Asn Gly Asp Thr Asp Tyr Asn Ser
65              70                  75                  80
```

Ala Ile Lys Ser Arg Leu Ser Ile Ser Arg Asp Thr Ser Lys Ser Gln
            85                  90                  95

Val Phe Leu Lys Met Asn Ser Leu Gln Thr Glu Asp Thr Ala Met Tyr
        100                 105                 110

Phe Cys Ala Asn Pro Tyr Tyr Gly Tyr Asn Phe Pro Phe Asp Tyr Trp
            115                 120                 125

Gly Gln Gly Val Met Val Thr Val Ser Ser
        130                 135

<210> SEQ ID NO 16
<211> LENGTH: 138
<212> TYPE: PRT
<213> ORGANISM: Rattus norvegicus

<400> SEQUENCE: 16

Met Ala Val Leu Val Leu Leu Cys Leu Leu Ile Phe Pro Ser Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Ser Ser Leu
        35                  40                  45

Thr Ser Asn Ser Val Ser Trp Ile Arg Gln Pro Pro Gly Lys Gly Leu
    50                  55                  60

Glu Trp Met Gly Val Ile Trp Ser Asn Gly Asp Ala Asp Tyr Asn Ser
65                  70                  75                  80

Ala Ile Lys Ser Arg Leu Ser Ile Ser Arg Asp Thr Ser Lys Ser Gln
            85                  90                  95

Val Phe Leu Lys Met Asn Ser Leu Gln Thr Glu Asp Thr Ala Met Tyr
        100                 105                 110

Phe Cys Ala Ser Pro Tyr Tyr Gly Tyr Tyr Phe Pro Phe Asp Tyr Trp
            115                 120                 125

Gly Gln Gly Val Met Val Thr Val Ser Ser
        130                 135

<210> SEQ ID NO 17
<211> LENGTH: 390
<212> TYPE: DNA
<213> ORGANISM: Rattus norvegicus

<400> SEQUENCE: 17
atggagacag acacactcct gctatgggtg ctgctgctct gggttccagg ctccactggt      60
gacattgtgc tgacccagtc tcctgctttg ctgtgtctc tagggcagag ggccacaatc      120
tcctgtagag ccagccaaag tgtcagtata tctagccatg atctcatgca gtggtaccaa     180
cagaaaccag acagcaacc caaactcctc atctatgatg cattcaacct agcatctggg      240
atccctgtca ggttcagtgg cagtgggtct gggacagact tcaccctcac cattgatcct      300
gtgcaggctg atgatattgc aacctattac tgtcagcaga gtaaggatga tccgtacacg     360
tttggagctg ggaccaagct ggaactgaaa                                      390

<210> SEQ ID NO 18
<211> LENGTH: 393
<212> TYPE: DNA
<213> ORGANISM: Rattus norvegicus

<400> SEQUENCE: 18
atgaaagtgc tggtaggct gctggtgctg ttgttttgga ttccagcttc caggagtgat       60

| | |
|---|---|
| gttgtgttga cacaaactcc agtttccctg tctgtcacac ttggagatca agcttctata | 120 |
| tcttgcaggt ctagtcagag cctgaatat agtgatggat acacttattt ggaatggtac | 180 |
| ctacagaagc caggccagtc tccacaggtc tcatctatg agtttccaa ccgatttct | 240 |
| ggggtcccag acaggttcat tggcagtggg tcagggacag atttcaccct caagatcagc | 300 |
| agagtagagc ctgaggactt gggagtttat tactgcttcc aagctacaca tgatccgtac | 360 |
| acgtttgggg ctgggaccag gctggaactg aaa | 393 |

<210> SEQ ID NO 19
<211> LENGTH: 384
<212> TYPE: DNA
<213> ORGANISM: Rattus norvegicus

<400> SEQUENCE: 19

| | |
|---|---|
| atgggtgtgc ctactcatct cctgggtttg ttgctgctct ggattacaca tgccatatgt | 60 |
| gatatccgga tgacacagtc tccagcttcc ctgtctgcat ctctgggaga aactgtcaac | 120 |
| atcgaatgtc tagcaagtga ggacgtttac agtgatttag catggtatca gcagaagcca | 180 |
| gggaaatctc ctcagctcct gatctataat gcaataatt tacaaagtgg ggtcccttca | 240 |
| cggtttagtg gcagtggatc tggcacacgg tattctctaa aaataaacag cctgcaatct | 300 |
| gaagatgtcg cgacttattt ctgtcaacaa tataacaatt atcctccgta cacgtttgga | 360 |
| gctgggacca agctggaact gaaa | 384 |

<210> SEQ ID NO 20
<211> LENGTH: 381
<212> TYPE: DNA
<213> ORGANISM: Rattus norvegicus

<400> SEQUENCE: 20

| | |
|---|---|
| atgaacgtgc ccactcaact ccttgggttg ctgctactct ggcttacagg tggtaaatgt | 60 |
| gacatccaga tgacacagtc tcctgcctcc ctgtctgctt ctctggaaga aattgtcacc | 120 |
| atcacctgca aggcaagcca gggcattgat aattacttat catggtatca gcagaaacca | 180 |
| gggaaatctc ctcagctcct gatctatgat gcaaccagct ggcagatggg gtcccatca | 240 |
| cggttcagcg gcagtagatc tggcacacag tattctctta agatcagcag accacaggtt | 300 |
| gatgattctg gaatctatta ctgtctacag agttacagta ctccattcac gttcggctca | 360 |
| gggacgaagt tggaaataaa a | 381 |

<210> SEQ ID NO 21
<211> LENGTH: 381
<212> TYPE: DNA
<213> ORGANISM: Rattus norvegicus

<400> SEQUENCE: 21

| | |
|---|---|
| atgaacgtgc ccactcaact ccttgggttg ctgctactct ggcttacagg tggtaaatgt | 60 |
| gacatccaga tgacacagtc tcctgcctcc ctgtctgctt ctctggaaga aattgtcacc | 120 |
| atcacctgca aggcaagcca ggccattgat gcttacttat catggtatca gcagaaacca | 180 |
| gggaaatctc ctcagctcct gatctatgat gcaaccagct ggcagatggg gtcccatca | 240 |
| cggttcagcg gcagtagatc tggcacacag tattctctta agatcagcag accacaggtt | 300 |
| gatgattctg gaatctatta ctgtctacag agttacagta ctccattcac gttcggctca | 360 |
| gggacgaagt tggaaataaa a | 381 |

<210> SEQ ID NO 22

```
<211> LENGTH: 130
<212> TYPE: PRT
<213> ORGANISM: Rattus norvegicus

<400> SEQUENCE: 22

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Asp Pro Tyr Thr Phe Gly Ala Gly Thr Lys Leu Glu
        115                 120                 125

Leu Lys
    130

<210> SEQ ID NO 23
<211> LENGTH: 131
<212> TYPE: PRT
<213> ORGANISM: Rattus norvegicus

<400> SEQUENCE: 23

Met Lys Val Pro Gly Arg Leu Leu Val Leu Leu Phe Trp Ile Pro Ala
1               5                   10                  15

Ser Arg Ser Asp Val Val Leu Thr Gln Thr Pro Val Ser Leu Ser Val
            20                  25                  30

Thr Leu Gly Asp Gln Ala Ser Ile Ser Cys Arg Ser Ser Gln Ser Leu
        35                  40                  45

Glu Tyr Ser Asp Gly Tyr Thr Tyr Leu Glu Trp Tyr Leu Gln Lys Pro
    50                  55                  60

Gly Gln Ser Pro Gln Val Leu Ile Tyr Gly Val Ser Asn Arg Phe Ser
65                  70                  75                  80

Gly Val Pro Asp Arg Phe Ile Gly Ser Gly Ser Gly Thr Asp Phe Thr
                85                  90                  95

Leu Lys Ile Ser Arg Val Glu Pro Glu Asp Leu Gly Val Tyr Tyr Cys
            100                 105                 110

Phe Gln Ala Thr His Asp Pro Tyr Thr Phe Gly Ala Gly Thr Arg Leu
        115                 120                 125

Glu Leu Lys
    130

<210> SEQ ID NO 24
<211> LENGTH: 128
<212> TYPE: PRT
<213> ORGANISM: Rattus norvegicus

<400> SEQUENCE: 24

Met Gly Val Pro Thr His Leu Leu Gly Leu Leu Leu Leu Trp Ile Thr
1               5                   10                  15

His Ala Ile Cys Asp Ile Arg Met Thr Gln Ser Pro Ala Ser Leu Ser
```

```
            20                  25                  30
Ala Ser Leu Gly Glu Thr Val Asn Ile Glu Cys Leu Ala Ser Glu Asp
        35                  40                  45

Val Tyr Ser Asp Leu Ala Trp Tyr Gln Gln Lys Pro Gly Lys Ser Pro
    50                  55                  60

Gln Leu Leu Ile Tyr Asn Ala Asn Asn Leu Gln Ser Gly Val Pro Ser
65                  70                  75                  80

Arg Phe Ser Gly Ser Gly Ser Gly Thr Arg Tyr Ser Leu Lys Ile Asn
                85                  90                  95

Ser Leu Gln Ser Glu Asp Val Ala Thr Tyr Phe Cys Gln Gln Tyr Asn
            100                 105                 110

Asn Tyr Pro Pro Tyr Thr Phe Gly Ala Gly Thr Lys Leu Glu Leu Lys
        115                 120                 125

<210> SEQ ID NO 25
<211> LENGTH: 127
<212> TYPE: PRT
<213> ORGANISM: Rattus norvegicus

<400> SEQUENCE: 25

Met Asn Val Pro Thr Gln Leu Leu Gly Leu Leu Leu Leu Trp Leu Thr
1               5                   10                  15

Gly Gly Lys Cys Asp Ile Gln Met Thr Gln Ser Pro Ala Ser Leu Ser
            20                  25                  30

Ala Ser Leu Glu Glu Ile Val Thr Ile Thr Cys Lys Ala Ser Gln Gly
        35                  40                  45

Ile Asp Asn Tyr Leu Ser Trp Tyr Gln Gln Lys Pro Gly Lys Ser Pro
    50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys
        115                 120                 125

<210> SEQ ID NO 26
<211> LENGTH: 127
<212> TYPE: PRT
<213> ORGANISM: Rattus norvegicus

<400> SEQUENCE: 26

Met Asn Val Pro Thr Gln Leu Leu Gly Leu Leu Leu Leu Trp Leu Thr
1               5                   10                  15

Gly Gly Lys Cys Asp Ile Gln Met Thr Gln Ser Pro Ala Ser Leu Ser
            20                  25                  30

Ala Ser Leu Glu Glu Ile Val Thr Ile Thr Cys Lys Ala Ser Gln Ala
        35                  40                  45

Ile Asp Ala Tyr Leu Ser Trp Tyr Gln Gln Lys Pro Gly Lys Ser Pro
    50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110
```

```
Ser Thr Pro Phe Thr Phe Gly Ser Gly Thr Lys Leu Glu Ile Lys
        115                 120                 125

<210> SEQ ID NO 27
<211> LENGTH: 5
<212> TYPE: PRT
<213> ORGANISM: Artificial sequence
<220> FEATURE:
<223> OTHER INFORMATION: Description of artificial sequence:
      KM4065 HCDR1

<400> SEQUENCE: 27

Asn Tyr Gly Met Ala
1               5

<210> SEQ ID NO 28
<211> LENGTH: 17
<212> TYPE: PRT
<213> ORGANISM: Artificial sequence
<220> FEATURE:
<223> OTHER INFORMATION: Description of artificial sequence:
      KM4065 HCDR2

<400> SEQUENCE: 28

Thr Ile Ser Tyr Asp Gly Ser Ile Thr Tyr Tyr Arg Asp Ser Val Lys
1               5                   10                  15
Gly

<210> SEQ ID NO 29
<211> LENGTH: 11
<212> TYPE: PRT
<213> ORGANISM: Artificial sequence
<220> FEATURE:
<223> OTHER INFORMATION: Description of artificial sequence:
      KM4065 HCDR3

<400> SEQUENCE: 29

Glu Glu Gln Tyr Ser Ser Trp Tyr Phe Asp Phe
1               5                   10

<210> SEQ ID NO 30
<211> LENGTH: 15
<212> TYPE: PRT
<213> ORGANISM: Artificial sequence
<220> FEATURE:
<223> OTHER INFORMATION: Description of artificial sequence:
      KM4065 LCDR1

<400> SEQUENCE: 30

Arg Ala Ser Gln Ser Val Ser Ile Ser Ser His Asp Leu Met Gln
1               5                   10                  15

<210> SEQ ID NO 31
<211> LENGTH: 7
<212> TYPE: PRT
<213> ORGANISM: Artificial sequence
<220> FEATURE:
<223> OTHER INFORMATION: Description of artificial sequence:
      KM4065 LCDR2

<400> SEQUENCE: 31

Asp Ala Phe Asn Leu Ala Ser
1               5

<210> SEQ ID NO 32
<211> LENGTH: 9
<212> TYPE: PRT
```

```
<213> ORGANISM: Artificial sequence
<220> FEATURE:
<223> OTHER INFORMATION: Description of artificial sequence:
      KM4065 LCDR3

<400> SEQUENCE: 32

Gln Gln Ser Lys Asp Asp Pro Tyr Thr
1               5

<210> SEQ ID NO 33
<211> LENGTH: 5
<212> TYPE: PRT
<213> ORGANISM: Artificial sequence
<220> FEATURE:
<223> OTHER INFORMATION: Description of artificial sequence:
      KM4066 HCDR1

<400> SEQUENCE: 33

Asn Tyr Gly Met Asn
1               5

<210> SEQ ID NO 34
<211> LENGTH: 17
<212> TYPE: PRT
<213> ORGANISM: Artificial sequence
<220> FEATURE:
<223> OTHER INFORMATION: Description of artificial sequence:
      KM4066 HCDR2

<400> SEQUENCE: 34

Ser Ile Ser Gly Ser Ser Thr Tyr Ile Tyr Tyr Ala Asp Thr Val Lys
1               5                   10                  15

Gly

<210> SEQ ID NO 35
<211> LENGTH: 15
<212> TYPE: PRT
<213> ORGANISM: Artificial sequence
<220> FEATURE:
<223> OTHER INFORMATION: Description of artificial sequence:
      KM4066 HCDR3

<400> SEQUENCE: 35

Glu Gly Ser Ser Thr Asp Arg Tyr Tyr Glu Val Ser Phe Ala Tyr
1               5                   10                  15

<210> SEQ ID NO 36
<211> LENGTH: 16
<212> TYPE: PRT
<213> ORGANISM: Artificial sequence
<220> FEATURE:
<223> OTHER INFORMATION: Description of artificial sequence:
      KM4066 LCDR1

<400> SEQUENCE: 36

Arg Ser Ser Gln Ser Leu Glu Tyr Ser Asp Gly Tyr Thr Tyr Leu Glu
1               5                   10                  15

<210> SEQ ID NO 37
<211> LENGTH: 7
<212> TYPE: PRT
<213> ORGANISM: Artificial sequence
<220> FEATURE:
<223> OTHER INFORMATION: Description of artificial sequence:
      KM4066 LCDR2

<400> SEQUENCE: 37

Gly Val Ser Asn Arg Phe Ser
```

<210> SEQ ID NO 38
<211> LENGTH: 9
<212> TYPE: PRT
<213> ORGANISM: Artificial sequence
<220> FEATURE:
<223> OTHER INFORMATION: Description of artificial sequence:
      KM4066 LCDR3

<400> SEQUENCE: 38

Phe Gln Ala Thr His Asp Pro Tyr Thr
1               5

<210> SEQ ID NO 39
<211> LENGTH: 5
<212> TYPE: PRT
<213> ORGANISM: Artificial sequence
<220> FEATURE:
<223> OTHER INFORMATION: Description of artificial sequence:
      KM4067 HCDR1

<400> SEQUENCE: 39

Thr Phe Thr Asp Tyr
1               5

<210> SEQ ID NO 40
<211> LENGTH: 17
<212> TYPE: PRT
<213> ORGANISM: Artificial sequence
<220> FEATURE:
<223> OTHER INFORMATION: Description of artificial sequence:
      KM4067 HCDR2

<400> SEQUENCE: 40

Glu Ile Tyr Pro Asn Asn Asn Thr Thr Asn Phe Asn Glu Lys Phe Lys
1               5                   10                  15

Gly

<210> SEQ ID NO 41
<211> LENGTH: 13
<212> TYPE: PRT
<213> ORGANISM: Artificial sequence
<220> FEATURE:
<223> OTHER INFORMATION: Description of artificial sequence:
      KM4067 HCDR3

<400> SEQUENCE: 41

Arg Gly Thr Val Tyr Tyr Gly Leu Gly Tyr Phe Asp His
1               5                   10

<210> SEQ ID NO 42
<211> LENGTH: 11
<212> TYPE: PRT
<213> ORGANISM: Artificial sequence
<220> FEATURE:
<223> OTHER INFORMATION: Description of artificial sequence:
      KM4067 LCDR1

<400> SEQUENCE: 42

Leu Ala Ser Glu Asp Val Tyr Ser Asp Leu Ala
1               5                   10

<210> SEQ ID NO 43
<211> LENGTH: 7
<212> TYPE: PRT
<213> ORGANISM: Artificial sequence
<220> FEATURE:

<223> OTHER INFORMATION: Description of artificial sequence:
      KM4067 LCDR2

<400> SEQUENCE: 43

Asn Ala Asn Asn Leu Gln Ser
1               5

<210> SEQ ID NO 44
<211> LENGTH: 10
<212> TYPE: PRT
<213> ORGANISM: Artificial sequence
<220> FEATURE:
<223> OTHER INFORMATION: Description of artificial sequence:
      KM4067 LCDR3

<400> SEQUENCE: 44

Gln Gln Tyr Asn Asn Tyr Pro Pro Tyr Thr
1               5                   10

<210> SEQ ID NO 45
<211> LENGTH: 5
<212> TYPE: PRT
<213> ORGANISM: Artificial sequence
<220> FEATURE:
<223> OTHER INFORMATION: Description of artificial sequence:
      KM4068 HCDR1

<400> SEQUENCE: 45

Ser Asn Ser Val Ser
1               5

<210> SEQ ID NO 46
<211> LENGTH: 16
<212> TYPE: PRT
<213> ORGANISM: Artificial sequence
<220> FEATURE:
<223> OTHER INFORMATION: Description of artificial sequence:
      KM4068 HCDR2

<400> SEQUENCE: 46

Ile Ile Trp Ser Asn Gly Asp Thr Asp Tyr Asn Ser Ala Ile Lys Ser
1               5                   10                  15

<210> SEQ ID NO 47
<211> LENGTH: 13
<212> TYPE: PRT
<213> ORGANISM: Artificial sequence
<220> FEATURE:
<223> OTHER INFORMATION: Description of artificial sequence:
      KM4068 HCDR3

<400> SEQUENCE: 47

Ala Asn Pro Tyr Tyr Gly Tyr Asn Phe Pro Phe Asp Tyr
1               5                   10

<210> SEQ ID NO 48
<211> LENGTH: 11
<212> TYPE: PRT
<213> ORGANISM: Artificial sequence
<220> FEATURE:
<223> OTHER INFORMATION: Description of artificial sequence:
      KM4068 LCDR1

<400> SEQUENCE: 48

Lys Ala Ser Gln Gly Ile Asp Asn Tyr Leu Ser
1               5                   10

<210> SEQ ID NO 49

```
<211> LENGTH: 7
<212> TYPE: PRT
<213> ORGANISM: Artificial sequence
<220> FEATURE:
<223> OTHER INFORMATION: Description of artificial sequence:
      KM4068 LCDR2

<400> SEQUENCE: 49

Asp Ala Thr Ser Leu Ala Asp
1               5

<210> SEQ ID NO 50
<211> LENGTH: 9
<212> TYPE: PRT
<213> ORGANISM: Artificial sequence
<220> FEATURE:
<223> OTHER INFORMATION: Description of artificial sequence:
      KM4068 LCDR3

<400> SEQUENCE: 50

Leu Gln Ser Tyr Ser Thr Pro Phe Thr
1               5

<210> SEQ ID NO 51
<211> LENGTH: 5
<212> TYPE: PRT
<213> ORGANISM: Artificial sequence
<220> FEATURE:
<223> OTHER INFORMATION: Description of artificial sequence:
      KM4069 HCDR1

<400> SEQUENCE: 51

Ser Asn Ser Val Ser
1               5

<210> SEQ ID NO 52
<211> LENGTH: 16
<212> TYPE: PRT
<213> ORGANISM: Artificial sequence
<220> FEATURE:
<223> OTHER INFORMATION: Description of artificial sequence:
      KM4069 HCDR2

<400> SEQUENCE: 52

Val Ile Trp Ser Asn Gly Asp Ala Asp Tyr Asn Ser Ala Ile Lys Ser
1               5                   10                  15

<210> SEQ ID NO 53
<211> LENGTH: 13
<212> TYPE: PRT
<213> ORGANISM: Artificial sequence
<220> FEATURE:
<223> OTHER INFORMATION: Description of artificial sequence:
      KM4069 HCDR3

<400> SEQUENCE: 53

Ala Asn Pro Tyr Tyr Gly Tyr Tyr Phe Pro Phe Asp Tyr
1               5                   10

<210> SEQ ID NO 54
<211> LENGTH: 11
<212> TYPE: PRT
<213> ORGANISM: Artificial sequence
<220> FEATURE:
<223> OTHER INFORMATION: Description of artificial sequence:
      KM4069 LCDR1

<400> SEQUENCE: 54

Lys Ala Ser Gln Ala Ile Asp Ala Tyr Leu Ser
```

<210> SEQ ID NO 55
<211> LENGTH: 7
<212> TYPE: PRT
<213> ORGANISM: Artificial sequence
<220> FEATURE:
<223> OTHER INFORMATION: Description of artificial sequence:
      KM4069 LCDR2

<400> SEQUENCE: 55

Asp Ala Thr Ser Leu Ala Asp
1               5

<210> SEQ ID NO 56
<211> LENGTH: 9
<212> TYPE: PRT
<213> ORGANISM: Artificial sequence
<220> FEATURE:
<223> OTHER INFORMATION: Description of artificial sequence:
      KM4069 LCDR3

<400> SEQUENCE: 56

Leu Gln Ser Tyr Ser Thr Pro Phe Thr
1               5

<210> SEQ ID NO 57
<211> LENGTH: 132
<212> TYPE: DNA
<213> ORGANISM: Artificial sequence
<220> FEATURE:
<223> OTHER INFORMATION: Description of artificial sequence:
      KM4065VH chmeric primer1

<400> SEQUENCE: 57
ccaattaacc ctcactaaag gggcggccgc gacccctcac catgaacctc gggctcagtt      60
tgattttcct tgccctcatt ttaaaaggtg tccagtgtga ggtgcaactg gtagagtctg     120
ggggcggttt ag                                                         132

<210> SEQ ID NO 58
<211> LENGTH: 80
<212> TYPE: DNA
<213> ORGANISM: Artificial sequence
<220> FEATURE:
<223> OTHER INFORMATION: Description of artificial sequence:
      KM4065VH chimeric primer2

<400> SEQUENCE: 58
gggtaatacg actcactata gggcgggccc ttggtggagg ctgaggacac ggtgaccatt      60
attcctggtc cccagaagtc                                                  80

<210> SEQ ID NO 59
<211> LENGTH: 116
<212> TYPE: DNA
<213> ORGANISM: Artificial sequence
<220> FEATURE:
<223> OTHER INFORMATION: Description of artificial sequence:
      KM4065VL chimeric primer1

<400> SEQUENCE: 59
ccaattaacc ctcactaaag gggaattcgc ctcttcaaaa tgaagttgcc tgttaggctg      60
ttggtgctga tgttctggat tcctgcttcc agcagtgaca ttgtgctgac ccagtc        116

<210> SEQ ID NO 60
<211> LENGTH: 50

```
<210> SEQ ID NO 61
<211> LENGTH: 118
<212> TYPE: DNA
<213> ORGANISM: Artificial sequence
<220> FEATURE:
<223> OTHER INFORMATION: Description of artificial sequence:
      KM4065VL chimeric primer2

<400> SEQUENCE: 60
gggtaatacg actcactata gggccgtacg tttcagttcc agcttggtcc            50

<210> SEQ ID NO 61
<211> LENGTH: 118
<212> TYPE: DNA
<213> ORGANISM: Artificial sequence
<220> FEATURE:
<223> OTHER INFORMATION: Description of artificial sequence:
      KM4066 chimeric primer1

<400> SEQUENCE: 61
ccaattaacc ctcactaaag gggcggccgc gaccectcac catgaacctc gggctcagtt    60
tgattttcct tgccctcatt ttaaaaggtg tccagtgtga ggtgcagctg gaggagtc     118

<210> SEQ ID NO 62
<211> LENGTH: 61
<212> TYPE: DNA
<213> ORGANISM: Artificial sequence
<220> FEATURE:
<223> OTHER INFORMATION: Description of artificial sequence:
      KM4066VH chimeric primer2

<400> SEQUENCE: 62
gggtaatacg actcactata gggcgggccc ttggtggagg ctgaagagac agtgaccaga    60
g                                                                    61

<210> SEQ ID NO 63
<211> LENGTH: 118
<212> TYPE: DNA
<213> ORGANISM: Artificial sequence
<220> FEATURE:
<223> OTHER INFORMATION: Description of artificial sequence:
      KM4066 chimeric primer1

<400> SEQUENCE: 63
ccaattaacc ctcactaaag gggaattcgc ctcttcaaaa tgaagttgcc tgttaggctg    60
ttggtgctga tgttctggat tcctgcttcc agcagtgatg ttgtgttgac acaaactc     118

<210> SEQ ID NO 64
<211> LENGTH: 50
<212> TYPE: DNA
<213> ORGANISM: Artificial sequence
<220> FEATURE:
<223> OTHER INFORMATION: Description of artificial sequence:
      KM4066VL chimeric primer2

<400> SEQUENCE: 64
gggtaatacg actcactata gggccgtacg tttcagttcc agcctggtcc            50

<210> SEQ ID NO 65
<211> LENGTH: 115
<212> TYPE: DNA
<213> ORGANISM: Artificial sequence
<220> FEATURE:
<223> OTHER INFORMATION: Description of artificial sequence:
      KM4067VH chimeric primer1

<400> SEQUENCE: 65
ccaattaacc ctcactaaag gggcggccgc gaccectcac catgagagtg cttattttat    60
```
tgtggctgtt cacagccttt cctggtattc ttagtcaggt caagctgctg cagtc        115

<210> SEQ ID NO 66
<211> LENGTH: 62
<212> TYPE: DNA
<213> ORGANISM: Artificial sequence
<220> FEATURE:
<223> OTHER INFORMATION: Description of artificial sequence:
      KM4067VH chimeric primer2

<400> SEQUENCE: 66
gggtaatacg actcactata gggcgggccc ttggtggagg ctgaagagac tgtgaccatg        60
ac        62

<210> SEQ ID NO 67
<211> LENGTH: 125
<212> TYPE: DNA
<213> ORGANISM: Artificial sequence
<220> FEATURE:
<223> OTHER INFORMATION: Description of artificial sequence:
      KM4067VL chimeric primer1

<400> SEQUENCE: 67
ccaattaacc ctcactaaag gggaattcgc ctcctcaaaa tgcattttca agtgcagatt        60
ttcagcttcc tgcttatttc ggcctcagtc ataatgtcca gaggagatat ccggatgaca       120
cagtc       125

<210> SEQ ID NO 68
<211> LENGTH: 50
<212> TYPE: DNA
<213> ORGANISM: Artificial sequence
<220> FEATURE:
<223> OTHER INFORMATION: Description of artificial sequence:
      KM4067VL chimeric primer2

<400> SEQUENCE: 68
gggtaatacg actcactata gggccgtacg tttcagttcc agcttggtcc        50

<210> SEQ ID NO 69
<211> LENGTH: 115
<212> TYPE: DNA
<213> ORGANISM: Artificial sequence
<220> FEATURE:
<223> OTHER INFORMATION: Description of artificial sequence:
      KM4068VH chimeric primer1

<400> SEQUENCE: 69
ccaattaacc ctcactaaag ggcggccgc gacccctcac catgagagtg cttattttat        60
tgtggctgtt cacagccttt cctggtattc ttagtcaagt gcaactaaag gagtc        115

<210> SEQ ID NO 70
<211> LENGTH: 60
<212> TYPE: DNA
<213> ORGANISM: Artificial sequence
<220> FEATURE:
<223> OTHER INFORMATION: Description of artificial sequence:
      KM4068VH chimeric primer2

<400> SEQUENCE: 70
gggtaatacg actcactata gggcgggccc ttggtggagg ctgaggagac tgtgaccatg        60

<210> SEQ ID NO 71
<211> LENGTH: 125
<212> TYPE: DNA

```
<213> ORGANISM: Artificial sequence
<220> FEATURE:
<223> OTHER INFORMATION: Description of artificial sequence:
      KM4068VL chimeric primer1

<400> SEQUENCE: 71
ccaattaacc ctcactaaag gggaattcgc ctcctcaaaa tgcattttca agtgcagatt    60
ttcagcttcc tgcttatttc ggcctcagtc ataatgtcca gaggagacat ccagatgaca   120
cagtc                                                               125

<210> SEQ ID NO 72
<211> LENGTH: 51
<212> TYPE: DNA
<213> ORGANISM: Artificial sequence
<220> FEATURE:
<223> OTHER INFORMATION: Description of artificial sequence:
      KM4068VL chimeric primer2

<400> SEQUENCE: 72
gggtaatacg actcactata gggccgtacg ttttatttcc aacttcgtcc c             51

<210> SEQ ID NO 73
<211> LENGTH: 115
<212> TYPE: DNA
<213> ORGANISM: Artificial sequence
<220> FEATURE:
<223> OTHER INFORMATION: Description of artificial sequence:
      KM4069 chimeric primer1

<400> SEQUENCE: 73
ccaattaacc ctcactaaag gggcggccgc gaccectcac catgagagtg cttattttat    60
tgtggctgtt cacagccttt cctggtattc ttagtcaagt gcaactaaag gagtc        115

<210> SEQ ID NO 74
<211> LENGTH: 61
<212> TYPE: DNA
<213> ORGANISM: Artificial sequence
<220> FEATURE:
<223> OTHER INFORMATION: Description of artificial sequence:
      KM4069VH chimeric primer2

<400> SEQUENCE: 74
gggtaatacg actcactata gggcgggccc ttggtggagg ctgaggagac tgtgaccatg    60
a                                                                    61

<210> SEQ ID NO 75
<211> LENGTH: 125
<212> TYPE: DNA
<213> ORGANISM: Artificial sequence
<220> FEATURE:
<223> OTHER INFORMATION: Description of artificial sequence:
      KM4069VL chimeric primer1

<400> SEQUENCE: 75
ccaattaacc ctcactaaag gggaattcgc ctcctcaaaa tgcattttca agtgcagatt    60
ttcagcttcc tgcttatttc ggcctcagtc ataatgtcca gaggagacat ccagatgaca   120
cagtc                                                               125

<210> SEQ ID NO 76
<211> LENGTH: 51
<212> TYPE: DNA
<213> ORGANISM: Artificial sequence
<220> FEATURE:
<223> OTHER INFORMATION: Description of artificial sequence:
```

KM4069VL chimeric primer2

<400> SEQUENCE: 76
gggtaatacg actcactata gggccgtacg ttttatttcc aacttcgtcc c          51

<210> SEQ ID NO 77
<211> LENGTH: 120
<212> TYPE: PRT
<213> ORGANISM: Artificial sequence
<220> FEATURE:
<223> OTHER INFORMATION: Description of artificial sequence:
      KM4065 HV0 amino acid sequence

<400> SEQUENCE: 77

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Leu Glu Trp Val
        35                  40                  45

Ala Thr Ile Ser Tyr Asp Gly Ser Ile Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Gln Tyr Ser Ser Trp Tyr Phe Asp Phe Trp Gly Gln
            100                 105                 110

Gly Thr Leu Val Thr Val Ser Ser
        115                 120
```

<210> SEQ ID NO 78
<211> LENGTH: 111
<212> TYPE: PRT
<213> ORGANISM: Artificial sequence
<220> FEATURE:
<223> OTHER INFORMATION: Description of artificial sequence:
      KM4065 LV0 amino acid sequence

<400> SEQUENCE: 78

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Ser Ile Ser
            20                  25                  30

Ser His Asp Leu Met Gln Trp Tyr Gln Gln Lys Pro Gly Lys Ala Pro
        35                  40                  45

Lys Leu Leu Ile Tyr Asp Ala Phe Asn Leu Ala Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Lys
                85                  90                  95

Asp Asp Pro Tyr Thr Phe Gly Gln Gly Thr Lys Leu Glu Ile Lys
            100                 105                 110
```

<210> SEQ ID NO 79
<211> LENGTH: 60
<212> TYPE: DNA
<213> ORGANISM: Artificial sequence
<220> FEATURE:
<223> OTHER INFORMATION: Description of artificial sequence:

A primer1 of CD4 expression vector

<400> SEQUENCE: 79
ccaattaacc ctcactaaag gggaattcga cccctcacca tgaaccgggg agtccctttt    60

<210> SEQ ID NO 80
<211> LENGTH: 59
<212> TYPE: DNA
<213> ORGANISM: Artificial sequence
<220> FEATURE:
<223> OTHER INFORMATION: Description of artificial sequence:
      A primer2 of CD4 expression vector

<400> SEQUENCE: 80
gggtaatacg actcactata gggcactagt gtcgcactca aatggggcta catgtcttc    59

<210> SEQ ID NO 81
<211> LENGTH: 41
<212> TYPE: DNA
<213> ORGANISM: Artificial sequence
<220> FEATURE:
<223> OTHER INFORMATION: Description of artificial sequence:
      A primer1 of CD4-Fc expression vector

<400> SEQUENCE: 81
tctgcccaca tggtccaccg agcccaaatc ttgtgacaaa a                        41

<210> SEQ ID NO 82
<211> LENGTH: 44
<212> TYPE: DNA
<213> ORGANISM: Artificial sequence
<220> FEATURE:
<223> OTHER INFORMATION: Description of artificial sequence:
      A primer2 of CD4-Fc expression vector

<400> SEQUENCE: 82
gggtaatacg actcactata gggcactagt ggatccgtcg cact                    44

<210> SEQ ID NO 83
<211> LENGTH: 92
<212> TYPE: DNA
<213> ORGANISM: Artificial sequence
<220> FEATURE:
<223> OTHER INFORMATION: Description of artificial sequence:
      A primer1 of 6G5VL

<400> SEQUENCE: 83
ccaattaacc ctcactaaag gggaattcga cccctcacca tgatggtccc agctcagctc    60
ctcggtctcc tgctgctctg gttcccaggt tc                                  92

<210> SEQ ID NO 84
<211> LENGTH: 93
<212> TYPE: DNA
<213> ORGANISM: Artificial sequence
<220> FEATURE:
<223> OTHER INFORMATION: Description of artificial sequence:
      A primer2 of 6G5VL

<400> SEQUENCE: 84
agtgatggtg actctgtctc ctacagatgc agacacggaa gatggagact gggtcatctg    60
gatgtcgcat ctggaacctg gaaccagag cag                                  93

<210> SEQ ID NO 85
<211> LENGTH: 93
<212> TYPE: DNA
<213> ORGANISM: Artificial sequence

```
<220> FEATURE:
<223> OTHER INFORMATION: Description of artificial sequence:
      A primer3 of 6G5VL

<400> SEQUENCE: 85
ggagacagag tcaccatcac ttgtcgggcg agtcaggata ttagcagctg gttagcctgg      60
tatcagcata aaccaggtaa agcacctaag ctc                                   93

<210> SEQ ID NO 86
<211> LENGTH: 101
<212> TYPE: DNA
<213> ORGANISM: Artificial sequence
<220> FEATURE:
<223> OTHER INFORMATION: Description of artificial sequence:
      A primer4 of 6G5VL

<400> SEQUENCE: 86
agagtgaaat ctgtcccaga tccacttccg ctgaaccttg atgggacacc actttgcaaa      60
ctggatgcag catagatcag gagcttaggt gctttacctg g                         101

<210> SEQ ID NO 87
<211> LENGTH: 94
<212> TYPE: DNA
<213> ORGANISM: Artificial sequence
<220> FEATURE:
<223> OTHER INFORMATION: Description of artificial sequence:
      A primer5 of 6G5VL

<400> SEQUENCE: 87
gatctgggac agatttcact ctcactatca gcagcctgca gcctgaagat tttgcaactt      60
actattgtca acaggctaat agtttcccgt acac                                  94

<210> SEQ ID NO 88
<211> LENGTH: 89
<212> TYPE: DNA
<213> ORGANISM: Artificial sequence
<220> FEATURE:
<223> OTHER INFORMATION: Description of artificial sequence:
      A primer6 of 6G5VL

<400> SEQUENCE: 88
gggtaatacg actcactata gggcggatcc cgtacgtttg atctccagct tggttccctg      60
accaaaagtg tacgggaaac tattagcct                                        89

<210> SEQ ID NO 89
<211> LENGTH: 148
<212> TYPE: DNA
<213> ORGANISM: Artificial sequence
<220> FEATURE:
<223> OTHER INFORMATION: Description of artificial sequence:
      A primer1 of 6G5VH

<400> SEQUENCE: 89
ccaattaacc ctcactaaag gggaattcgc ggccgcgacc cctcaccatg aaacacctgt      60
ggttcttcct cctcctggtg gcagctccta gatgggtcct gtctcaggtg cagctacagc    120
agtggggcgc aggactgttg aagccttc                                       148

<210> SEQ ID NO 90
<211> LENGTH: 129
<212> TYPE: DNA
<213> ORGANISM: Artificial sequence
<220> FEATURE:
<223> OTHER INFORMATION: Description of artificial sequence:
      A primer2 of 6G5VH
```

<400> SEQUENCE: 90
gatttcacca atccactcca gacccttacc tggtggctgg cggatccagc tccagtagta    60
accactgaag gaaccaccat agacagcgca ggtgagggac agggtctccg aaggcttcaa   120
cagtcctgc                                                          129

<210> SEQ ID NO 91
<211> LENGTH: 156
<212> TYPE: DNA
<213> ORGANISM: Artificial sequence
<220> FEATURE:
<223> OTHER INFORMATION: Description of artificial sequence:
      A primer3 of 6G5VH

<400> SEQUENCE: 91
ctggagtgga ttggtgaaat caatcatagt ggaagcacca actacaaccc gtctctcaag    60
agtcgagtca ccatatcagt agacacgtcc aagaaccagt tctctctgaa actgagctct   120
gtgaccgctg cggacacggc tgtgtattac tgtgcg                             156

<210> SEQ ID NO 92
<211> LENGTH: 124
<212> TYPE: DNA
<213> ORGANISM: Artificial sequence
<220> FEATURE:
<223> OTHER INFORMATION: Description of artificial sequence:
      A primer4 of 6G5VH

<400> SEQUENCE: 92
gggtaatacg actcactata gggcggatcc gggcccttgg ttgaggctga ggagacggtg    60
accagggttc cctggcccca aggtcgaac caattaatta ctctcgcaca gtaatacaca   120
gccg                                                               124

<210> SEQ ID NO 93
<211> LENGTH: 360
<212> TYPE: DNA
<213> ORGANISM: Artificial sequence
<220> FEATURE:
<223> OTHER INFORMATION: Description of artificial sequence:
      A DNA sequence of KM4065 HV0

<400> SEQUENCE: 93
gaggtgcagc tggtggagtc tgggggcggc ttggtacagc ctgggcggtc cctgcggctc    60
tcctgtgcag cctctgggtt cacctttagt aactatggca tggcctgggt ccgccaggct   120
ccagggaagg ggctggagtg ggtcgcaacc attagttatg atggcagtat cacttattat   180
cgagactccg tgaagggccg gttcaccatc tcccgggaca attccaagaa cacgctgtac   240
ctgcaaatga acagcctgcg agccgaggac acggccgtat attactgtgc gcgggaggaa   300
caatatagca gctggtactt tgacttctgg ggccagggga ccctggtcac cgtctcctca   360

<210> SEQ ID NO 94
<211> LENGTH: 333
<212> TYPE: DNA
<213> ORGANISM: Artificial sequence
<220> FEATURE:
<223> OTHER INFORMATION: Description of artificial sequence:
      A DNA sequence of KM4065 LV0

<400> SEQUENCE: 94
gacatccagc tgacccagtc tccatcctcc ctgtctgcat ctgtaggtga ccgggtcacc    60
atcacttgtc gggccagcca agtgtcagt atctctagcc atgatctcat gcagtggtat   120

```
cagcagaaac cagggaaagc ccctaagctc ctgatctatg atgcattcaa cctggcatct    180
ggggtcccat cacggttcag cggcagtggt tctgggacag atttcactct caccatcagc    240
agcctgcagc ctgaagattt tgcaacttat tactgccagc agagtaagga tgatccgtac    300
acgttcggcc aggggaccaa gctggagatc aaa                                  333
```

<210> SEQ ID NO 95
<211> LENGTH: 360
<212> TYPE: DNA
<213> ORGANISM: Artificial sequence
<220> FEATURE:
<223> OTHER INFORMATION: Description of artificial sequence:
      HV2 DNA sequence
<220> FEATURE:
<221> NAME/KEY: CDS
<222> LOCATION: (1)..(360)

<400> SEQUENCE: 95

```
gag gtg cag ctg gtg gag tct ggg ggc ggc ttg gta cag cct ggg cgg    48
Glu Val Gln Leu Val Glu Ser Gly Gly Gly Leu Val Gln Pro Gly Arg
1               5                   10                  15 tcc ctg cgg ctc tcc tgt gca gcc tct ggg ttc acc ttt agt aac tat    96
Ser Leu Arg Leu Ser Cys Ala Ala Ser Gly Phe Thr Phe Ser Asn Tyr
            20                  25                  30 ggc atg gcc tgg gtc cgc cag gct cca ggg aag ggg ctg gag tgg gtc   144
Gly Met Ala Trp Val Arg Gln Ala Pro Gly Lys Gly Leu Glu Trp Val
        35                  40                  45 gca acc att agt tat gat ggc agt atc act tat tat cga gac tcc gtg   192
Ala Thr Ile Ser Tyr Asp Gly Ser Ile Thr Tyr Tyr Arg Asp Ser Val
    50                  55                  60 aag ggc cgg ttc acc atc tcc cgg gac aat tcc aag aac acg ctg tac   240
Lys Gly Arg Phe Thr Ile Ser Arg Asp Asn Ser Lys Asn Thr Leu Tyr
65                  70                  75                  80 ctg caa atg aac agc ctg cga gcc gag gac acg gcc gta tat tac tgt   288
Leu Gln Met Asn Ser Leu Arg Ala Glu Asp Thr Ala Val Tyr Tyr Cys
                85                  90                  95 acg cgg gag gaa caa tat agc agc tgg tac ttt gac ttc tgg ggc cag   336
Thr Arg Glu Glu Gln Tyr Ser Ser Trp Tyr Phe Asp Phe Trp Gly Gln
            100                 105                 110 ggg atc ctg gtc acc gtc tcc tca                                     360
Gly Ile Leu Val Thr Val Ser Ser
        115                 120
```

<210> SEQ ID NO 96
<211> LENGTH: 120
<212> TYPE: PRT
<213> ORGANISM: Artificial sequence
<220> FEATURE:
<223> OTHER INFORMATION: Description of artificial sequence:
      HV2 amino acid sequence

<400> SEQUENCE: 96

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Leu Glu Trp Val
        35                  40                  45

Ala Thr Ile Ser Tyr Asp Gly Ser Ile Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Thr Arg Glu Glu Gln Tyr Ser Ser Trp Tyr Phe Asp Phe Trp Gly Gln
            100                 105                 110

Gly Ile Leu Val Thr Val Ser Ser
        115                 120

<210> SEQ ID NO 97
<211> LENGTH: 360
<212> TYPE: DNA
<213> ORGANISM: Artificial sequence
<220> FEATURE:
<223> OTHER INFORMATION: Description of artificial sequence:
      HV3 DNA sequence
<220> FEATURE:
<221> NAME/KEY: CDS
<222> LOCATION: (1)..(360)

<400> SEQUENCE: 97 gag gtg cag ctg gtg gag tct ggg ggc ggc ttg gta cag cct ggg cgg        48
Glu Val Gln Leu Val Glu Ser Gly Gly Gly Leu Val Gln Pro Gly Arg
1               5                   10                  15 tcc ctg cgg ctc tcc tgt gca gcc tct ggg ttc acc ttt agt aac tat        96
Ser Leu Arg Leu Ser Cys Ala Ala Ser Gly Phe Thr Phe Ser Asn Tyr
            20                  25                  30 ggc atg gcc tgg gtc cgc cag gct cca ggg aag ggg ctg gag tgg gtc       144
Gly Met Ala Trp Val Arg Gln Ala Pro Gly Lys Gly Leu Glu Trp Val
        35                  40                  45 gca acc att agt tat gat ggc agt atc act tat tat cga gac tcc gtg       192
Ala Thr Ile Ser Tyr Asp Gly Ser Ile Thr Tyr Tyr Arg Asp Ser Val
    50                  55                  60 aag ggc cgg ttc acc atc tcc cgg gac aat tcc aag aac acg ctg tac       240
Lys Gly Arg Phe Thr Ile Ser Arg Asp Asn Ser Lys Asn Thr Leu Tyr
65                  70                  75                  80 ctg caa atg aac agc ctg cga gcc gag gac acg gcc acc tat tac tgt       288
Leu Gln Met Asn Ser Leu Arg Ala Glu Asp Thr Ala Thr Tyr Tyr Cys
                85                  90                  95 acc cgg gag gaa caa tat agc agc tgg tac ttt gac ttc tgg ggc cag       336
Thr Arg Glu Glu Gln Tyr Ser Ser Trp Tyr Phe Asp Phe Trp Gly Gln
            100                 105                 110 ggg atc ctg gtc acc gtc tcc tca                                       360
Gly Ile Leu Val Thr Val Ser Ser
        115                 120

<210> SEQ ID NO 98
<211> LENGTH: 120
<212> TYPE: PRT
<213> ORGANISM: Artificial sequence
<220> FEATURE:
<223> OTHER INFORMATION: Description of artificial sequence:
      HV3 amino acid sequence

<400> SEQUENCE: 98

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Gly Met Ala Trp Val Arg Gln Ala Pro Gly Lys Gly Leu Glu Trp Val
        35                  40                  45

Ala Thr Ile Ser Tyr Asp Gly Ser Ile Thr Tyr Tyr Arg Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Thr Tyr Tyr Cys
                    85                  90                  95

Thr Arg Glu Glu Gln Tyr Ser Ser Trp Tyr Phe Asp Phe Trp Gly Gln
                    100                 105                 110

Gly Ile Leu Val Thr Val Ser Ser
            115                 120

<210> SEQ ID NO 99
<211> LENGTH: 360
<212> TYPE: DNA
<213> ORGANISM: Artificial sequence
<220> FEATURE:
<223> OTHER INFORMATION: Description of artificial sequence:
      HV4 DNA sequence
<220> FEATURE:
<221> NAME/KEY: CDS
<222> LOCATION: (1)..(360)

<400> SEQUENCE: 99 gag gtg cag ctg gtg gag tct ggg ggc ggc ttg gta cag cct ggg cgg        48
Glu Val Gln Leu Val Glu Ser Gly Gly Gly Leu Val Gln Pro Gly Arg
1               5                   10                  15 tcc atg cgg ctc tcc tgt gca gcc tct ggg ttc acc ttt agt aac tat        96
Ser Met Arg Leu Ser Cys Ala Ala Ser Gly Phe Thr Phe Ser Asn Tyr
                20                  25                  30 ggc atg gcc tgg gtc cgc cag gct cca ggg aag ggg ctg gag tgg gtc       144
Gly Met Ala Trp Val Arg Gln Ala Pro Gly Lys Gly Leu Glu Trp Val
            35                  40                  45 gca acc att agt tat gat ggc agt atc act tat tat cga gac tcc gtg       192
Ala Thr Ile Ser Tyr Asp Gly Ser Ile Thr Tyr Tyr Arg Asp Ser Val
        50                  55                  60 aag ggc cgg ttc acc atc tcc cgg gac aat tcc aag aac acg ctg tac       240
Lys Gly Arg Phe Thr Ile Ser Arg Asp Asn Ser Lys Asn Thr Leu Tyr
65                  70                  75                  80 ctg caa atg aac agc ctg cga gcc gag gac acg gcc acc tat tac tgt       288
Leu Gln Met Asn Ser Leu Arg Ala Glu Asp Thr Ala Thr Tyr Tyr Cys
                85                  90                  95 acc cgg gag gaa caa tat agc agc tgg tac ttt gac ttc tgg ggc cag       336
Thr Arg Glu Glu Gln Tyr Ser Ser Trp Tyr Phe Asp Phe Trp Gly Gln
                100                 105                 110 ggg atc ctg gtc acc gtc tcc tca                                       360
Gly Ile Leu Val Thr Val Ser Ser
            115                 120

<210> SEQ ID NO 100
<211> LENGTH: 120
<212> TYPE: PRT
<213> ORGANISM: Artificial sequence
<220> FEATURE:
<223> OTHER INFORMATION: Description of artificial sequence:
      HV4 amino acid sequence

<400> SEQUENCE: 100

Glu Val Gln Leu Val Glu Ser Gly Gly Gly Leu Val Gln Pro Gly Arg
1               5                   10                  15

Ser Met Arg Leu Ser Cys Ala Ala Ser Gly Phe Thr Phe Ser Asn Tyr
                20                  25                  30

Gly Met Ala Trp Val Arg Gln Ala Pro Gly Lys Gly Leu Glu Trp Val
            35                  40                  45

Ala Thr Ile Ser Tyr Asp Gly Ser Ile Thr Tyr Tyr Arg Asp Ser Val
        50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Thr Tyr Tyr Cys
                 85                  90                  95

Thr Arg Glu Glu Gln Tyr Ser Ser Trp Tyr Phe Asp Phe Trp Gly Gln
            100                 105                 110

Gly Ile Leu Val Thr Val Ser Ser
        115                 120

<210> SEQ ID NO 101
<211> LENGTH: 333
<212> TYPE: DNA
<213> ORGANISM: Artificial sequence
<220> FEATURE:
<223> OTHER INFORMATION: Description of artificial sequence:
      LV6 DNA sequence
<220> FEATURE:
<221> NAME/KEY: CDS
<222> LOCATION: (1)..(333)

<400> SEQUENCE: 101 gac atc cag ctg acc cag tct cca tcc tcc ctg tct gtc tct ctt ggt    48
Asp Ile Gln Leu Thr Gln Ser Pro Ser Ser Leu Ser Val Ser Leu Gly
 1               5                  10                  15 gac cgg gcc acc atc act tgt cgg gcc agc caa agt gtc agt atc tct    96
Asp Arg Ala Thr Ile Thr Cys Arg Ala Ser Gln Ser Val Ser Ile Ser
             20                  25                  30 agc cat gat ctc atg cag tgg tat cag cag aaa cca ggg aaa cag cct   144
Ser His Asp Leu Met Gln Trp Tyr Gln Gln Lys Pro Gly Lys Gln Pro
         35                  40                  45 aag ctc ctg atc tat gat gca ttc aac ctg gca tct ggg atc cca tca   192
Lys Leu Leu Ile Tyr Asp Ala Phe Asn Leu Ala Ser Gly Ile Pro Ser
     50                  55                  60 cgg ttc agc ggc agt ggt tct ggg aca gat ttc act ctc acc atc agc   240
Arg Phe Ser Gly Ser Gly Ser Gly Thr Asp Phe Thr Leu Thr Ile Ser
 65                  70                  75                  80 agc gtg cag cct gaa gat ttt gca act tat tac tgc cag cag agt aag   288
Ser Val Gln Pro Glu Asp Phe Ala Thr Tyr Tyr Cys Gln Gln Ser Lys
                 85                  90                  95 gat gat ccg tac acg ttc ggc cag ggg acc aag ctg gag atc aaa       333
Asp Asp Pro Tyr Thr Phe Gly Gln Gly Thr Lys Leu Glu Ile Lys
            100                 105                 110

<210> SEQ ID NO 102
<211> LENGTH: 111
<212> TYPE: PRT
<213> ORGANISM: Artificial sequence
<220> FEATURE:
<223> OTHER INFORMATION: Description of artificial sequence:
      LV6 amino acid sequence

<400> SEQUENCE: 102

Asp Ile Gln Leu Thr Gln Ser Pro Ser Ser Leu Ser Val Ser Leu Gly
 1               5                  10                  15

Asp Arg Ala Thr Ile Thr Cys Arg Ala Ser Gln Ser Val Ser Ile Ser
             20                  25                  30

Ser His Asp Leu Met Gln Trp Tyr Gln Gln Lys Pro Gly Lys Gln Pro
         35                  40                  45
```

-continued

```
Lys Leu Leu Ile Tyr Asp Ala Phe Asn Leu Ala Ser Gly Ile Pro Ser
    50              55                  60

Arg Phe Ser Gly Ser Gly Ser Gly Thr Asp Phe Thr Leu Thr Ile Ser
65              70                  75                  80

Ser Val Gln Pro Glu Asp Phe Ala Thr Tyr Tyr Cys Gln Gln Ser Lys
                85                  90                  95

Asp Asp Pro Tyr Thr Phe Gly Gln Gly Thr Lys Leu Glu Ile Lys
            100                 105                 110
```

ANTI-CD4 ANTIBODY

BACKGROUND OF THE INVENTION

1. Field of the Invention

The present invention relates to a monoclonal antibody or an antibody fragment thereof, which binds to human CD4 extracellular region with a high affinity and also exhibits a high antibody-dependent cellular cytotoxicity (hereinafter, referred to as "ADCC activity") or a high complement-dependent cellular cytotoxicity (hereinafter, referred to as "CDC activity"); a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent and a diagnostic agent using the antibody or the antibody fragment thereof.

2. Brief Description of the Background Art

Cluster of differentiation 4 (hereinafter, referred to as "CD4") is a glycoprotein having a molecular weight of about 55 kDa, which is expressed on the cell surface of most of thymic cells, about ⅔ of peripheral blood T cells, monocytes, and macrophage. CD4 is a type I transmembrane protein in which four immunoglobulin superfamily domains (designated in order as D1 to D4 from the N terminal to the cell membrane side) are present on the outside of the cells, and two N-linked sugar chains in total are bound to the domains D3 to D4. CD4 binds to a major histocompatibility complex (MHC) class II molecule through D1 and D2 domains, and then activates the T cells. Further, it is also known that CD4 polymerizes through D3 and D4 domains. D1 domain of CD4 is known to serve as a receptor for a human immunodeficiency virus (hereinafter, referred to as "HIV") (Non-Patent Literature 1).

CD4 is also known as T4, and the gene has been cloned in 1985 (Non-Patent Literature 2), and the DNA sequence, the amino acid sequence and the three-dimensional structure of CD4 are publicly available from a known database. For example, these can be obtained by reference to Accession Nos. P01730 (SWISSPROT), M12807 (EMBL), and the like.

The anti-CD4 monoclonal antibody OKT4 was first confirmed as a monoclonal antibody (hereinafter, referred to as "mAb") which binds to CD4 (Non-Patent Literature 3). Since then, a large number of monoclonal antibodies against CD4 (hereinafter, referred to as "anti-CD4 mAbs") have been reported. Most of anti-CD4 mAbs reported hitherto are known to recognize D1 domain (Non-Patent Literature 1). Some of anti-CD4 mAbs are under clinical development for the purpose of treating cancers, immune diseases, and infections. For example, based on the fact that the binding between CD4 and HIV is essential for the infection of HIV, an antibody which recognizes D1 domain of CD4 can inhibit the infection of HIV, under the development as an HIV therapeutic agent.

Examples of the anti-CD4 mAb developed as a therapeutic agent for cancers or immune diseases include zanolimumab (6G5) (Non-Patent Literature 4), keliximab (CE9.1) (Non-Patent Literature 5), and the like. These antibodies are antibodies which exert their medicinal efficacy by specifically attacking CD4-expressing cells which are target cells, and it is considered that the mechanism of medicinal efficacy is mainly due to an ADCC activity (Non-Patent Literatures 6 and 7). Meanwhile, these antibodies are shown to be devoid of a CDC activity which is generally known as one of the main mechanism of medicinal efficacy of therapeutic antibodies, like ADCC (Non-Patent Literatures 6 and 7).

The potency of CDC activity is different depending on the subclass of antibodies, and human IgG1 and IgG3 subclasses have a high CDC activity. It is known that the intensity of CDC activity among the subclasses is generally in the order of IgG3≧IgG1>>IgG2≈IgG4. In addition, there is a case where the CDC activity of an antibody is exerted or is not exerted depending on an antigen to which the antibody binds (Non-Patent Literature 11). Accordingly, every antibody cannot always exhibit the CDC activity.

Among the anti-CD4 mAbs confirmed hitherto, little is known of the antibodies having a CDC activity. Uniquely, even though it is known that OKT4 exhibits a CDC activity against a CD4-positive human cell line only when a rabbit serum which is high in complement number is used (Non-Patent Literature 8), no examples of an antibody which exhibits a CDC activity against a CD4-positive human cell line when a human complement is used have been reported.

A dissociation constant $K_D$ of an antibody for several known anti-CD4 mAbs has been reported. For example, antibodies shown in the following table have been reported to have a dissociation constant $K_D$ of about 7 to 0.01 nM (Table 1). Upon the calculation of dissociation constants, there is a possibility that measurement values vary depending on assay equipments, assay methods, and analysis methods. Therefore, when comparing dissociation constants, the values which were measured and analyzed under the same conditions are required.

TABLE 1

| Clone Name | Dissociation Constant [M] |
|---|---|
| 6G5* | $7.1 \times 10^{-9}$ |
| CE9.1* | $3.2 \times 10^{-11}$ |
| Leu-3a** | $1.0 \times 10^{-11}$ |
| 13B8.2*** | $5.0 \times 10^{-9}$ |

*WO97/13852,
**Non-Patent Literature 9,
***Non-Patent Literature 10

Non-Patent Literature 1: *Leucocyte Typing* VI, 49 (1997)
Non-Patent Literature 2: *Cell*, 42, 93 (1985)
Non-Patent Literature 3: *Proc. Natl. Acad. Sci. USA*, 76, 4061 (1979)
Non-Patent Literature 4: *Blood*, 109, 4655 (2007)
Non-Patent Literature 5: *Lancet*, 352, 1109 (1998)
Non-Patent Literature 6: *Clin Immunol Immunopathol*, 84, 73 (1997)
Non-Patent Literature 7: *Cancer Res*, 67, 9945 (2007)
Non-Patent Literature 8: *J Immunol*, 164, 1925 (2000)
Non-Patent Literature 9: *J Immunol*, 145, 2839 (1990)
Non-Patent Literature 10: *Clinical Immunology*, 119, 38 (2006)
Non-Patent Literature 11: *J. Immunol.*, 174, 5706(2005)

SUMMARY OF THE INVENTION

An object of the present invention is to provide a monoclonal antibody or an antibody fragment thereof, which binds to a CD4 extracellular region with high affinity and also exhibits a high ADCC activity or CDC activity; a hybridoma which produces the antibody; a DNA which encodes the antibody; a vector which contains the DNA; a transformant obtainable by introducing the vector; a process for producing an antibody or an antibody fragment thereof using the hybridoma or the transformant; and a therapeutic agent or a diagnostic agent using the antibody or the antibody fragment thereof.

BRIEF DESCRIPTION OF THE DRAWINGS

In FIG. 3(A), ● represents an anti-CD4 rat monoclonal antibody KM4065, and × represents an anti-CD4 rat monoclonal antibody KM4069. In FIG. 3(B), × represents an anti-CD4 rat monoclonal antibody KM4068. In FIG. 3(C), ■ represents an anti-CD4 rat monoclonal antibody KM4066, and □ represents an anti-CD4 rat monoclonal antibody KM4067. In FIG. 3(D), ● represents an anti-CD4 mouse monoclonal antibody OKT4.

FIG. 9(A) shows an ADCC activity when HPB-ALL was used as a target cell. FIG. 9(B) shows an ADCC activity when HUT78 was used as a target cell. FIG. 9(C) shows an ADCC activity when SUP-T1 is used as a target cell. FIG. 9(D) shows an ADCC activity when HPB-ALL was used as a target cell.

FIGS. 10(A) to 10(B) show a complement-dependent cellular cytotoxicity (CDC activity) of various anti-CD4 antibodies on a CD4-expressing transfectant or a human lymphoma cell line. The ordinate represents a cellular cytotoxicity rate (%), and the abscissa represents an antibody concentration of each antibody. FIG. 10(A) shows a CDC activity on a CD4-expressing transfectant. FIG. 10(B) shows a CDC activity on the human lymphoma cell line HPB-ALL. ♦ in the broken line represents an anti-CD4 human antibody 6G5-1, ♦ in the solid line represents an anti-CD4 human antibody 6G5-113F, ▲ represents an anti-CD4 chimeric antibody KM4045, ● represents an anti-CD4 chimeric antibody KM4046, ■ represents an anti-CD4 chimeric antibody KM4047, – represents an anti-CD4 chimeric antibody KM4048, ■ represents an anti-CD4 chimeric antibody KM4049, and ■ in the broken line represents an anti-CD4 mouse antibody OKT4.

FIG. 12(A) shows an ADCC activity when HPB-ALL was used as a target cell. FIG. 12(B) shows an ADCC activity when HUT78 was used as a target cell. FIG. 12(C) shows an ADCC activity when CCRF-CEM was used as a target cell.

In FIG. 14(A), the ordinate represents a liver weight ratio. In FIG. 14(B), the ordinate represents a kidney weight ratio. The bar represents a standard deviation.

DETAILED DESCRIPTION OF THE INVENTION

Figure 1:
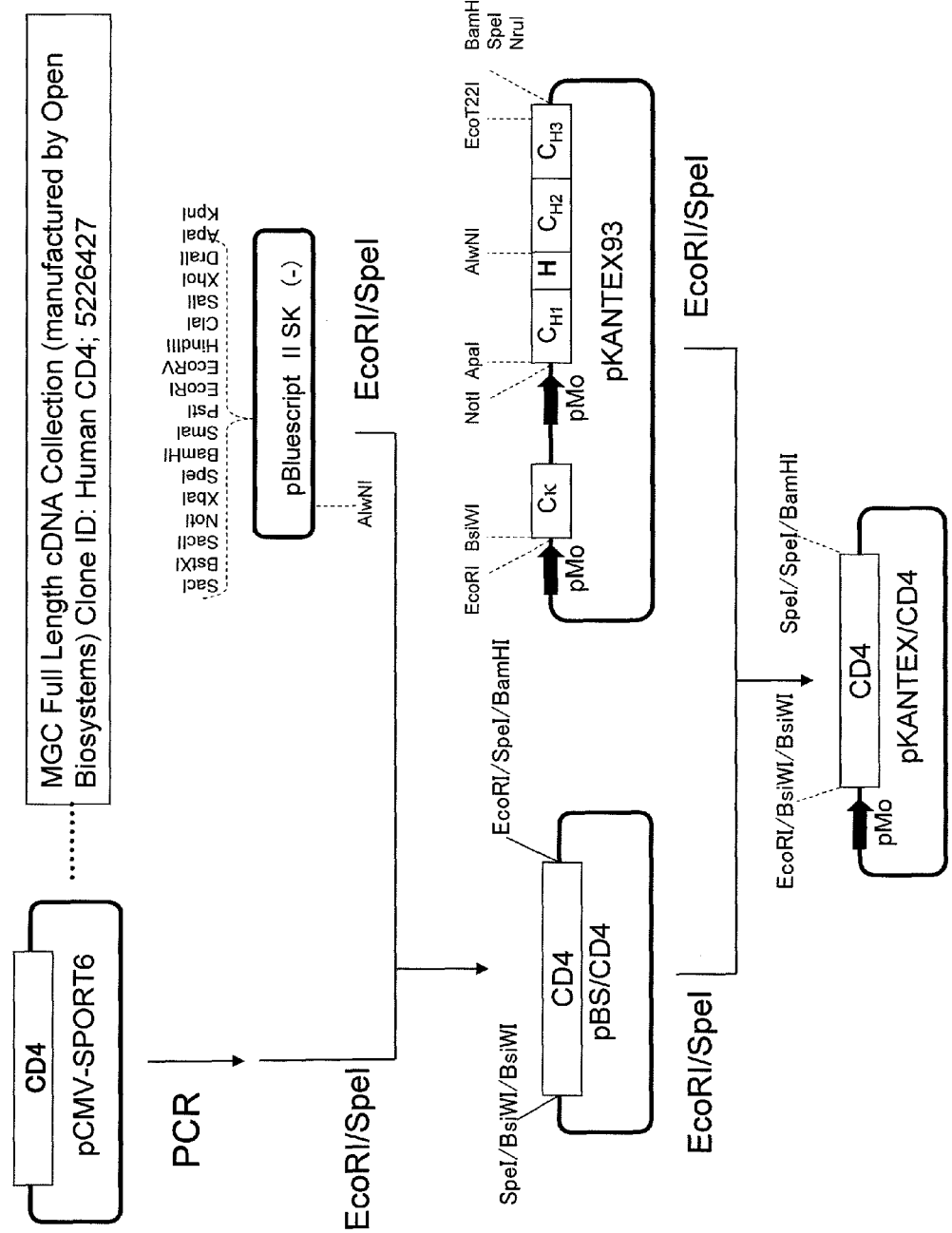
FIG. 1 shows a construction process of a CD4 expression vector.

The present invention relates to the following (1) to (35):
(1) A monoclonal antibody against human CD4 or an antibody fragment thereof, which has a dissociation constant (hereinafter, referred to as "$K_D$") less than $1 \times 10^{-9}$M of an antibody to an antigen, binds to an extracellular region of human CD4 with high affinity and has a high antibody-dependent cellular cytotoxicity (hereinafter, referred to as "ADCC activity");
(2) The monoclonal antibody or the antibody fragment thereof described in the above (1), wherein the antibody is an antibody having a high complement-dependent cellular cytotoxicity (CDC activity);
(3) The monoclonal antibody or the antibody fragment thereof described in the above (2), wherein the antibody is an antibody which has a CDC activity on a human cancer cell line expressing human CD4;
(4) The monoclonal antibody or the antibody fragment thereof described in any one of the above (1) to (3), wherein the monoclonal antibody is a monoclonal antibody which competes with an antibody in which complementarity determining regions (hereinafter, referred to as "CDRs") 1 to 3 of a heavy chain (hereinafter, referred to as "H chain") of the antibody comprise the amino acid sequences of SEQ ID NOs:51 to 53, respectively, and CDRs 1 to 3 of a light chain (hereinafter, referred to as "L chain") of the antibody comprise the amino acid sequences of SEQ ID NOs:54 to 56, respectively, to bind to an extracellular region of CD4;
(5) The monoclonal antibody or the antibody fragment thereof described in any one of the above (1) to (4), the monoclonal antibody is a monoclonal antibody which binds to the same epitope as an epitope in an extracellular region of CD4 to which an antibody in which CDRs 1 to 3 of an H chain of the antibody comprise the amino acid sequences of SEQ ID NOs:51 to 53, respectively, and CDRs 1 to 3 of an L chain of the antibody comprise the amino acid sequences of SEQ ID NOs:54 to 56, respectively, binds;
(6) The monoclonal antibody or the antibody fragment thereof described in any one of the above (1) to (2), wherein the monoclonal antibody is a monoclonal antibody which competes with an antibody in which CDRs 1 to 3 of an H chain of the antibody comprise the amino acid sequences of SEQ ID NOs:27 to 29, respectively, and CDRs 1 to 3 of an L chain of the antibody comprise the amino acid sequences of SEQ ID NOs:30 to 32, respectively, to bind to an extracellular region of CD4.
(7) The monoclonal antibody or the antibody fragment thereof described in any one of the above (1) to (2) and (6), wherein the monoclonal antibody is a monoclonal antibody which binds to the same epitope in an extracellular region of CD4 as an epitope to which an antibody in which CDRs 1 to 3 of an H chain of the antibody comprise the amino acid sequences of SEQ ID NOs:27 to 29, respectively, and CDRs 1 to 3 of an L chain of the antibody comprise the amino acid sequences of SEQ ID NOs:30 to 32, respectively, binds;
(8) The antibody or the antibody fragment thereof described in any one of the above (1) to (7), wherein the monoclonal antibody is a recombinant antibody;
(9) The recombinant antibody or the antibody fragment thereof described in the above (8), wherein the recombinant antibody is a recombinant antibody selected from a human chimeric antibody, a humanized antibody and a human antibody;
(10) The recombinant antibody or the antibody fragment thereof described in the above (9), wherein an H chain variable region (hereinafter, referred to as "VH") of the antibody and an L chain variable region (hereinafter, referred to as "VL") of the antibody comprise the amino acid sequences of any one group selected from SEQ ID NO:16 and SEQ ID NO:26, respectively; and SEQ ID NO:12 and SEQ ID NO:22, respectively;
(11) The recombinant antibody or the antibody fragment thereof described in the above (9), wherein CDRs 1 to 3 of an H chain of the antibody and CDRs 1 to 3 of the L chain of an antibody comprise the amino acid sequences of any one group selected from SEQ ID NOs:51 to 53 and SEQ ID NOs:54 to 56, respectively; and SEQ ID NOs:27 to 29 and SEQ ID NOs:30 to 32, respectively;
(12) The humanized antibody or the antibody fragment thereof described in the above (9), wherein the recombinant antibody is a humanized antibody, and VH and VL of the antibody comprise the amino acid sequences of any one group selected from SEQ ID NO:77 and SEQ ID NO:78, respectively; SEQ ID NO:96 and SEQ ID NO:78, respectively; SEQ ID NO:98 and SEQ ID NO:78, respectively; SEQ ID NO:100 and SEQ ID NO:78, respectively; and SEQ ID NO:100 and SEQ ID NO:102, respectively;
(13) The antibody or the antibody fragment thereof described in any one of the above (1) to (13), wherein the antibody fragment is an antibody fragment selected from Fab, Fab', F(ab')$_2$, a single chain antibody (scFv), a dimerized V region (diabody), a disulfide stabilized V region (dsFv) and a peptide comprising CDR;
(14) A DNA which encodes the antibody or the antibody fragment thereof described in any one of the above (1) to (13);
(15) A recombinant vector which comprises the DNA described in the above (14);
(16) A transformant obtainable by introducing the recombinant vector described in the above (15) into a host cell;
(17) A process for producing the monoclonal antibody or the antibody fragment thereof described in any one of the above (1) to (13), comprising culturing the transformant described in the above (16) in a medium to produce and accumulate the antibody or the antibody fragment thereof described in any one of the above (1) to (14) in the culture, and collecting the antibody or the antibody fragment thereof from the culture;
(18) A method for immunologically detecting or measuring human CD4, comprising using the antibody or the antibody fragment thereof described in any one of the above (1) to (13);
(19) An agent for detecting or measuring human CD4, comprising using the antibody or the antibody fragment thereof described in any one of the above (1) to (13);
(20) A diagnostic agent for a disease relating to human CD4, comprising using the antibody or the antibody fragment thereof described in any one of the above (1) to (13);
(21) The diagnostic agent described in the above (20), wherein the disease relating to human CD4-positive cell is a cancer;
(22) The diagnostic agent described in the above (20), wherein the disease relating to a human CD4-positive cell is an allergic disease or an autoimmune disease;

(23) A therapeutic agent for a relating to human CD4-positive cell, comprising the antibody or the antibody fragment thereof described in any one of the above (1) to (13) as an active ingredient;

(24) The therapeutic agent described in the above (23), wherein the disease relating to a human CD4-positive cell is a cancer;

(25) The therapeutic agent described in the above (23), wherein the disease relating to a human CD4-positive cell is an allergic disease or an autoimmune disease;

(26) A method for diagnosing a disease relating to a human CD4-positive cell, comprising detecting or measuring a human CD4-positive cell;

(27) A method for diagnosing a disease relating to a human CD4-positive cell, comprising detecting or measuring a human CD4;

(28) The method for diagnosing described in the above (26) or (27), wherein the disease relating to a human CD4-positive cell is a cancer;

(29) The method for diagnosing described in the above (26) or (27), wherein the disease relating to a human CD4-positive cell is an allergic disease or an autoimmune disease;

(30) Use of the antibody or the antibody fragment thereof described in any one of the above (1) to (13) for the manufacture of a diagnostic agent for a disease relating to a human CD4-positive cell;

(31) The use of the antibody or the antibody fragment thereof described in the above (30), wherein the disease relating to a human CD4-positive cell is a caner;

(32) The use of the antibody or the antibody fragment thereof described in the above (30), wherein the disease relating to a human CD4-positive cell is an allergic disease or an autoimmune disease;

(33) Use of the antibody or the antibody fragment thereof described in any one of the above (1) to (13) for the manufacture of a therapeutic agent for a disease relating to a human CD4-positive cell;

(34) The use of the antibody or the antibody fragment thereof described in the above (33), wherein the disease relating to a human CD4-positive cell is a caner; and

(35) The use of the antibody or the antibody fragment thereof described in the above (33), wherein the disease relating to a human CD4-positive cell is an allergic disease or an autoimmune disease.

The present invention can provide a monoclonal antibody or an antibody fragment thereof, which specifically recognizes an extracellular region of human CD4 and binds to the extracellular region with a high affinity, and also exhibits a high ADCC activity or a high CDC activity; a hybridoma which produces the antibody; a DNA which encodes the antibody; a vector which comprises the DNA; a transformant obtainable by introducing the vector; a process for producing the antibody or the antibody fragment thereof using the hybridoma or the transformant; and a therapeutic agent and a diagnostic agent using the antibody or the antibody fragment thereof.

The present invention relates to a monoclonal antibody or an antibody fragment thereof, which binds with a high affinity to an extracellular region of CD4 and accordingly has a high antibody-dependent cellular cytotoxicity (hereinafter, referred to as "ADCC activity").

CD4 of the present invention includes a polypeptide comprising the amino acid sequence represented by SEQ ID NO:1 or EMBL Accession No. M12807; a polypeptide comprising an amino acid sequence in which one or more amino acid residue(s) is/are deleted, substituted or added in the amino acid sequence represented by SEQ ID NO:1 or EMBL Accession No. M12807, and having the activity of CD4; a polypeptide comprising an amino acid sequence having at least 60% homology, preferably at least 80% homology, more preferably at least 90% homology, and most preferably at least 95% homology, with the amino acid sequence represented by SEQ ID NO:1 or EMBL Accession No. M12807, and having the activity of CD4; and the like.

The polypeptide comprising an amino acid sequence in which one or more amino acid residue(s) is/are deleted, substituted and/or added in the amino acid sequence represented by SEQ ID NO:1 or EMBL Accession No. M12807 can be obtained, for example, by introducing a site-specific mutation into DNA encoding a polypeptide comprising the amino acid sequence represented by SEQ ID NO:1 by site-specific mutagenesis [*Molecular Cloning, A Laboratory Manual,* Second Edition, Cold Spring Harbor Laboratory Press (1989), *Current Protocols in Molecular Biology,* John Wiley & Sons (1987-1997), *Nucleic Acids Research,* 10, 6487 (1982), *Proc. Natl. Acad. Sci. USA,* 79, 6409 (1982), *Gene,* 34, 315 (1985), *Nucleic Acids Research,* 13, 4431 (1985), or *Proc. Natl. Acad. Sci. USA,* 82, 488 (1985)] or the like. The number of amino acid residues which are deleted, substituted or added is not particularly limited, and the number is preferably, 1 to dozens, such as 1 to 20, and more preferably 1 to several, such as 1 to 5.

As a gene encoding CD4, the nucleotide sequence represented by SEQ ID NO:2 or EMBL Accession No. M12807 may be exemplified. As the gene encoding CD4, the gene encoding CD4 of the present invention also included a gene containing a DNA comprising a nucleotide sequence having deletion(s), substitution(s) or addition(s) of one or more nucleotides in the nucleotide sequence represented by SEQ ID NO:2 or EMBL Accession No. M12807 and also encoding a polypeptide having the function of CD4; a gene containing a DNA consisting of a nucleotide sequence having at least 60% or higher homology, preferably 80% or higher homology, and more preferably 95% or higher homology, with the nucleotide sequence represented by SEQ ID NO:2 or EMBL Accession No. M12807, and also encoding a polypeptide having the function of CD4; a gene consisting of a DNA which hybridizes with a DNA having the nucleotide sequence represented by SEQ ID NO:2 or EMBL Accession No. M12807 under stringent conditions and also containing a DNA that encodes a polypeptide having the function of CD4; and the like.

In the present invention, the DNA which hybridizes under stringent conditions refers to a DNA which is obtained by colony hybridization, plaque hybridization, Southern blot hybridization, DNA microarray or the like using a DNA having the nucleotide sequence represented by SEQ ID NO:2 or EMBL Accession No. M12807 as a probe. A specific example of such DNA is a hybridized colony- or plaque derived DNA which can be identified by performing hybridization at 65° C. in the presence of 0.7 to 1.0 mol/L sodium chloride using a filter or slide glass with the PCR product or oligo DNA having immobilized thereon, and then washing the filter or slide glass at 65° C. with a 0.1 to 2-fold concentration SSC solution (1-fold concentration SSC solution: 150 mmol/L sodium chloride and 15 mmol/L sodium citrate). Hybridization can be carried out according to the methods [*Molecular Cloning, A Laboratory Manual,* Second Edition, Cold Spring Harbor Lab. Press (1989), *Current Protocols in Molecular Biology,* John Wiley & Sons (1987-1997); *DNA Cloning* 1: *Core Techniques, A Practical Approach,* Second Edition, Oxford University (1995)] and the like. Specifically, the DNA capable of hybridization includes DNA having at least 60% or more homology, preferably 80% or more homology, more preferably 90% or more homology, and most preferably 95% or more homology to the nucleotide sequence represented by SEQ ID NO:2 or EMBL Accession No. M12807.

In the nucleotide sequence of the gene encoding a protein of a eukaryote, genetic polymorphism is often recognized. The CD4 gene used in the present invention also includes a gene in which small modification is generated in the nucleotide sequence by such polymorphism as the gene used in the present invention.

The number of the homology in the present invention may be a number calculated by using a homology search program known by the skilled person, unless otherwise indicated. Regarding the nucleotide sequence, the number may be calculated by using BLAST [*J. Mol. Biol.*, 215, 403 (1990)] with a default parameter or the like, and regarding the amino acid sequence, the number may be calculated by using BLAST2 [*Nucleic Acids Res.*, 25, 3389 (1997); *Genome Res.*, 7, 649 (1997) with a default parameter; http://www.ncbi.nlm.nih.gov/Education/BLASTinfo/information3.html] or the like.

As the default parameter, G (cost to open gap) is 5 for the nucleotide sequence and 11 for the amino acid sequence; –E (cost to extend gap) is 2 for the nucleotide sequence and 1 for the amino acid sequence; –q (penalty for nucleotide mismatch) is –3; –r (reward for nucleotide match) is 1; –e (expect value) is 10; –W (wordsize) is 11 residues for the nucleotide sequence and 3 residues for the amino acid sequence; –y [dropoff (X) for blast extensions in bits] is 20 for blastn and 7 for a program other than blastn; –X (X dropoff value for gapped alignment in bits) is 15; and –Z (final X dropoff value for gapped alignment in bits) is 50 for blastn and 25 for a program other than blastn (http://www.ncbi.nlm.nih.gov/blast/html/blastcgihelp.html).

The polypeptide comprising a partial sequence of the amino acid sequence represented by SEQ ID NO:1 or EMBL Accession No. M12807 can be prepared according to a method known by the skilled person. For example, it can be prepared by deleting a part of DNA encoding the amino acid sequence represented by SEQ ID NO:2 and culturing a transformant into which an expression vector containing the DNA is introduced. Also, based on the polypeptide or DNA prepared by using the above method, a polypeptide comprising an amino acid sequence in which one or more amino acid(s) is/are deleted, substituted or added in a partial sequence of the amino acid sequence represented by SEQ ID NO:1 or EMBL Accession No. M12807 can be prepared in the same manner as described above. In addition, the polypeptide comprising a partial sequence of the amino acid sequence represented by SEQ ID NO:1 or EMBL Accession No. M12807; or a polypeptide comprising an amino acid sequence in which one or more amino acid(s) is/are deleted, substituted or added in a partial sequence of the amino acid sequence represented by SEQ ID NO:1 or EMBL Accession No. M12807 can be produced by a chemical synthesis method such as fluorenylmethoxycarbonyl (Fmoc) method or t-butyloxycarbonyl (tBoc) method.

In the present invention, the extracellular region of CD4 includes, for example, regions predicted from the amino acid sequence of the polypeptide represented by SEQ ID NO:1 by using conventionally known transmembrane region deducing program SOSUI (http://bp.nuap.nagoya-u.ac.jp/SOSUI/SOSUI_submit.), TMHMM ver. 2 (http://www.cbs.dtu.dk/services/TMHMM-2.0/), ExPASy Proteomics Server (http://Ca.expasy.org/) or the like.

Examples of the extracellular region of CD4 in the present invention include regions corresponding to N-terminal to position 394 in the extracellular domain predicted by SOSUI. The extracellular region comprises immunoglobulin superfamily domains (D1 to D4) and every domain is comprised in the predicted extracellular domain.

The extracellular region of CD4 in the present invention may be any structure, so long as it has a structure equivalent to a structure which can be taken in a native state by the extracellular region of CD4 having the amino acid sequence represented by SEQ ID NO:1 or EMBL Accession No. M12807. The term "structure which can be taken in a native state by the extracellular region of CD4" refers to a native three-dimensional (comformational) structure of CD4 which is expressed on a cell membrane.

The function of CD4 in the present invention means that CD4 induces the activation or differentiation of T cells by acting as a cofactor of a T cell receptor when CD4 binds to an MHC class II-antigen complex which is expressed on an antigen-presenting cell, through the T cell receptor which is expressed on T cells. In addition, examples of the function of CD4 also includes its participation in the infection of T cells with HIV by such a manner that CD4 expressed on a cell membrane of T cells binds to gp120 which is one of envelope proteins of a human immunodeficiency virus (HIV).

Binding of the antibody or antibody fragment of the present invention to the extracellular region of CD4 can be confirmed by a method in which the binding ability of a cell expressing a specified antigen and an antibody for the specific antigen can be examined, for example, by a radioimmunoassay using a solid phase sandwich method or the like, or a conventionally known immunological detecting method for a cell expressing CD4 using an enzyme immuno assay (ELISA) method, preferably a fluorescent cell staining method or the like. Examples include a fluorescent antibody staining method using the FMAT8100HTS system (manufactured by Applied Biosystem), [*Cancer Immunol. Immunother.*, 36, 373 (1993)], a fluorescent cell staining method using a flow cytometry, a surface plasmon resonance using the Biacore system (manufactured by GE Healthcare) and the like. In addition, it can also be confirmed by a combination of conventionally known immunological detecting methods [*Monoclonal Antibodies—Principles and Practice,* Third edition, Academic Press (1996), *Antibodies—A Laboratory Manual,* Cold Spring Harbor Laboratory (1988), *Monoclonal Antibody Experiment Manual,* Kodansha Scientific (1987)] and the like.

In the present invention, as a cell expressing CD4 includes any cells which so long as express CD4. Examples include a cell which exists in human body, a cell line which is established from naturally existing cell in human body, and a cell line which is produced by using gene recombinant techniques.

The cell which is naturally present in the human body includes a cell expressing CD4 in the body of a patient suffering from autoimmune disease, an allergic patient and a cancer patient. Examples include a cell expressing CD4 among tumor cells obtained by biopsy or the like.

The cell line established from the cell which is naturally present in the human body includes a cell line expressing CD4 among the cell lines obtained by establishing the above-described cells expressing CD4 obtained from a cancer patient, such as a human T cell lymphoma cell line HPB-ALL (DSMZ NO: ACC483) or HUT78 (ATCC No: TIB16).

Specific examples of the cell obtained by using gene recombination technique includes a cell expressing CD4, which is prepared by introducing an expression vector comprising cDNA encoding CD4 into an insect cell, an animal cell, etc., and the like.

Examples of the antibody of the present invention include a monoclonal antibody or an antibody fragment thereof against human CD4 which has a dissociation constant (hereinafter, referred to as "$K_D$") less than $1\times10^{-9}$M of the antibody to CD4, binds to an extracellular region of human CD4 with high affinity and has high ADCC activity.

Examples of the antibody of the present invention include a monoclonal antibody or an antibody fragment thereof against human CD4 which has a dissociation constant "$K_D$" of the antibody of $1\times10^{-9}$M or less to the antigen and has a high ADCC activity and a high complement-dependent cellular cytotoxicity (CDC activity). Examples of the antibody of the present invention also include an antibody or an antibody fragment which has CDC activity on a human cancer cell line expressing human CD4.

The monoclonal antibody of the present invention includes an antibody produced by a hybridoma and a recombinant antibody produced by a transformant transformed with an expression vector containing a gene encoding the antibody.

The monoclonal antibody is an antibody secreted by a single clone antibody-producing cell, and recognizes only one epitope (also called antigen determinant) and has uniform amino acid sequence (primary structure).

In the present invention, the monoclonal antibody has a structure comprising a heterotetramer consisting of two H chains and two L chains. A H chain comprises a H chain variable region (hereinafter referred to as "VH") and a H chain constant region (hereinafter referred to as "CH"); and a L chain comprises a L chain variable region (hereinafter referred to as "VL") and a L chain constant region (hereinafter referred to as "CL"). In addition, CH comprises four domains: CH1 domain, hinge domain, CH2 domain and CH3 domain. Furthermore, a domain consisting of CH2 domain and CH3 domain together is defined as "Fc region", "Fc domain" or simply "Fc" of an antibody.

Examples of the epitope include a single amino acid sequence, a three-dimensional structure formed by an amino acid sequence, an amino acid sequence having a sugar chain bound thereto, a three-dimensional structure formed by an amino acid sequence having a sugar chain bound thereto, and the like, which a monoclonal antibody recognizes and binds to. Examples of the epitope of the monoclonal antibody of the present invention include preferably the extracellular region of CD4, and an epitope corresponding to position 1 to 394 of the amino acid sequence represented by SEQ ID NO:1, more preferably an epitope comprising D1 or D2 of the extracellular region of CD4, and an epitope comprising D3 or D4 of the extracellular region of CD4 near a cell membrane and the like.

In the present invention, an antibody which binds to CD4 with high affinity is an antibody which has enough affinity for a therapeutic antibody, preferably an antibody which binds to CD4 with dissociation constant $K_D$ value less than $1\times10^{-9}$M, preferably less than $7\times10^{-10}$M, more preferably less than $2\times10^{-10}$M in terms of affinity. Zanolimumab (6G5) with which a clinical trial has already started has affinity with dissociation constant $K_D$ value of $7.1\times10^{-9}$M and exhibited high therapeutic effects. Therefore, the antibody of the present invention can exhibit high therapeutic effects.

Affinity is measured by kinetic analysis, and for example, can be measured by using a Biacore T100 (manufactured by GE Healthcare Bio-Sciences), or the like.

In the present invention, the term "dissociation is slow" means that a value of a dissociation rate constant kd of an antibody calculated by Biacore T100 has a smaller value. The smaller dissociation rate constant represents that an antibody does not easily dissociate from an antigen-expressing cell. By increasing an amount of an antibody binding to the cell surface to thereby extend the effective time of the antibody, then a high medicinal efficacy can be expected. A dissociation rate constant kd is measured, for example, using a Biacore T100 (manufactured by GE Healthcare Bio-Sciences), and can be calculated by software attached to the apparatus, Biacore T100 evaluation software (manufactured by Biacore).

As used herein, the term "antibody having a high ADCC activity" refers to an antibody having a higher ADCC activity than anti-CD4 antibodies 6G5 and CE9.1 which had been reported to have an ADCC activity, when ADCC activities of plural antibodies were simultaneously measured for CD4-expressing cells, using a known assay method [*Cancer Immunol. Immunother.*, 36, 373(1993)].

The term "ADCC activity" refers to an activity which leads to the cytotoxicity to a target cell by such a manner that an antibody bound to an antigen on the target cell binds to an Fc receptor of an immune cell through an Fc region of the antibody, consequently resulting in the activation of the immune cell (natural killer cell, etc.).

An Fc receptor (hereinafter referred to as "FcR") is a receptor which binds to Fc region of an antibody and leads to various effector activities by binding to the antibody. An FcR corresponds to a subclass of an antibody, and IgG, IgE, IgA and IgM specifically binds to FcγR, FcεR, FcαR and FcμR, respectively. Moreover, an FcγR has subtypes of FcγRI (CD64), FcγRII (CD32) and FcγRIII (CD16) and these have isoforms of FcγRIA, FcγRIB, FcγRIC, FcγRIIA, FcγRIIB, FcγRIIC, FcγRIIIA and FcγRIIIB, respectively. The above different FcγRs exist on different cells (*Annu. Rev. Immunol.*, 9:457-492 (1991)). In human, FcγRIIIB specifically expresses on a neutrophil and FcγRIIIA expresses on a monocyte, a Natural Killer cell (NK cell) and some part of T cell. Binding of an antibody through FcγRIIIA leads to an NK cell-dependent ADCC activity.

In the present invention, the term "antibody having a high CDC activity" refers to an antibody having a higher CDC activity than conventional anti-CD4 antibodies, when CDC activities of plural antibodies were simultaneously measured for CD4-expressing cells, using a human complement and a known CDC assay method [*Cancer Immunol. Immunother.*, 36, 373(1993)]. More preferred is an antibody having a higher CDC activity than conventional anti-CD4 antibodies, when a CDC activity of the antibody was measured in the same manner as above for a CD4-expressing cell which is naturally present in the human body or CD4-positive cancer cell line. More specifically, such an antibody is one exhibiting a higher CDC activity than a conventional anti-CD4 antibody 6G5 or OKT4, in the same experimental system.

The term "CDC activity" refers to an activity which leads to the cytotoxicity to a target cell by such a manner that an antibody bound to an antigen on the target cell activates a series of cascades (complement activation pathways) containing complement-related protein groups in blood. In addition, protein fragments generated by the activation of a complement can induce the migration and activation of immune cells.

Examples of the antibody of the present invention include a monoclonal antibody or an antibody fragment which binds to either D1 or D2 of the extracellular region of CD4, or D3 or D4 of the extracellular region of CD4 near a cell membrane.

Further, among the antibodies of the present invention, examples of an antibody which recognizes D1 or D2 domain include a monoclonal antibody in which a heavy chain constant region (hereinafter referred to as VH) of the antibody comprises the amino acid sequences of CDRs 1 to 3 represented by SEQ ID NOs:33 to 35, respectively, and a light chain constant region (hereinafter referred to as VL) of the antibody comprises the amino acid sequences of CDRs 1 to 3 represented by SEQ ID NOs:36 to 38, respectively, and the like. In addition, among specific antibodies of the present invention, examples of an antibody which recognizes D3 or D4 domain include a monoclonal antibody in which VH of the antibody comprises the amino acid sequences of CDRs 1 to 3 represented by SEQ ID NOs:51 to 53, respectively, and VL of the antibody comprises the amino acid sequences of CDRs 1 to 3 represented by SEQ ID NOs:54 to 56, respectively; a monoclonal antibody in which VH of the antibody comprises the amino acid sequences of CDRs 1 to 3 represented by SEQ ID NOs:27 to 29, respectively, and VL of the antibody comprises the amino acid sequences of CDRs 1 to 3 represented by SEQ ID NOs:30 to 32, respectively; a monoclonal antibody in which VH of the antibody comprises the amino acid sequences of CDRs 1 to 3 represented by SEQ ID NOs:39 to 41, respectively, and VL of the antibody comprises the amino acid sequences of CDRs 1 to 3 represented by SEQ ID NOs: 42 to 44, respectively; and a monoclonal antibody in which VH of the antibody comprises the amino acid sequences of CDRs 1 to 3 represented by SEQ ID NOs:45 to 47, respectively, and VL of the antibody comprises the amino acid sequences of CDRs 1 to 3 represented by SEQ ID NOs:48 to 50, respectively.

Moreover, specific examples of the monoclonal antibody of the present invention include a monoclonal antibody wherein VH of the antibody comprises the amino acid sequence represented by SEQ ID NO:16 and VL of the antibody comprises the amino acid sequence represented by SEQ ID NO:26; a monoclonal antibody wherein VH of the antibody comprises the amino acid sequence represented by SEQ ID NO:12 and VL of the antibody comprises the amino acid sequence represented by SEQ ID NO:22; a monoclonal antibody wherein VH of the antibody comprises the amino acid sequence represented by SEQ ID NO:13 and VL of the antibody comprises the amino acid sequence represented by SEQ ID NO:23; a monoclonal antibody wherein VH of the antibody comprises the amino acid sequence represented by SEQ ID NO:14 and VL of the antibody comprises the amino acid sequence represented by SEQ ID NO:24; a monoclonal antibody wherein VH of the antibody comprises the amino acid sequence represented by SEQ ID NO:15 and VL of the antibody comprises the amino acid sequence represented by SEQ ID NO:25; and the like.

In addition, examples of the monoclonal antibody of the present invention include a monoclonal antibody which competes with the above monoclonal antibody in the binding of the extracellular region of CD4, a monoclonal antibody which binds to the same epitope as an epitope in an extracellular region of CD4 to which the above monoclonal antibody binds.

Moreover, an antibody or the antibody fragment which binds to CD4 and has apoptosis-inducing activity.

The hybridoma can be prepared, for example, by preparing the above cell expressing CD4 as an antigen, inducing an antibody-producing cell having antigen specificity from an animal immunized with the antigen, and fusing the antigen-producing cell with a myeloma cell. The anti-CD4 monoclonal antibody can be obtained by culturing the hybridoma or administering the hybridoma cell into an animal to cause ascites tumor in the animal and separating and purifying the culture or the ascites.

The animal immunized with an antigen may be any animal, so long as a hybridoma can be prepared, and mouse, rat, hamster, chicken, rabbit or the like is suitably used. Also, the antibody of the present invention includes an antibody produced by a hybridoma obtained by fusion of the cell having antibody-producing activity can be obtained from such an animal, and immune in vitro with a myeloma cell.

In the present invention, the recombinant antibody includes an antibody produced by gene recombination, such as a human chimeric antibody, a humanized antibody (complementarity determining region (hereinafter referred to as CDR)-grafted antibody), a human antibody and an antibody fragment thereof. Among the recombinant antibodies, one having characters of a monoclonal antibody, low immunogenecity and prolonged half-life in blood is preferable as a therapeutic agent. Examples of the recombinant antibody include an antibody in which the above monoclonal antibody of the present invention is modified by gene recombination technology.

CH of the recombinant antibody of the resent invention is preferably of human origin and includes CH1 domain, CH2 domain and CH3 domain.

Fc region of the recombinant antibody of the present invention may include one or more amino acid modification, so long as it has binding activity to FcγR.

The human chimeric antibody is an antibody comprising a heavy chain variable region VH and a light chain variable region VL of an antibody of a non-human animal and CH and CL of a human antibody. Specifically, the human chimeric antibody of the present invention can be produced by obtaining cDNAs encoding VH and VL from a hybridoma which produces a monoclonal antibody which specifically recognizes CD4 and binds to the extracellular region, inserting each of them into an expression vector for animal cell comprising DNAs encoding CH and CL of human antibody to thereby construct a vector for expression of human chimeric antibody, and then introducing the vector into an animal cell to express the antibody.

As the CH of the human chimeric antibody, any CH can be used, so long as it belongs to human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of the human chimeric antibody, any CL can be used, so long as it belongs to the hIg class, and those belonging to κ class or λ class can be used.

Specific examples of the human chimeric antibody of the present invention include a human chimeric antibody wherein VH of the antibody comprises the amino acid sequence represented by SEQ ID NO:16 and VL of the antibody comprises the amino acid sequence represented by SEQ ID NO:26; a human chimeric antibody wherein VH of the antibody comprises the amino acid sequence represented by SEQ ID NO:12 and VL of the antibody comprises the amino acid sequence represented by SEQ ID NO:22; a human chimeric antibody wherein VH of the antibody comprises the amino acid sequence represented by SEQ ID NO:13 and VL of the antibody comprises the amino acid sequence represented by SEQ ID NO:23; a human chimeric antibody wherein VH of the antibody comprises the amino acid sequence represented by SEQ ID NO:14 and VL of the antibody comprises the amino acid sequence represented by SEQ ID NO:24; a human chimeric antibody wherein VH of the antibody comprises the amino acid sequence represented by SEQ ID NO:15 and VL of the antibody comprises the amino acid sequence represented by SEQ ID NO:25; and the like.

In addition, examples of the chimeric antibody of the present invention include a chimeric antibody which competes with the above chimeric antibody in the binding of the extracellular region of CD4 and a chimeric antibody which binds to the same epitope as an epitope in an extracellular region of CD4 to which the above chimeric antibody binds.

A humanized antibody is an antibody in which amino acid sequences of CDRs of VH and VL of an antibody derived from a non-human animal are grafted into appropriate positions of VH and VL of a human antibody. The humanized antibody of the present invention can be produced by constructing cDNAs encoding a V region in which the amino acid sequences of CDRs of VH and VL of an antibody derived from a non-human animal produced by a hybridoma which produces a monoclonal antibody which specifically recognizes CD4 and binds to the extracellular region are grafted into frame work region (hereinafter referred to as "FR") of VH and VL of any human antibody, inserting each of them into a vector for expression of animal cell comprising genes encoding CH and CL of a human antibody to thereby construct a vector for expression of humanized antibody, and introducing it into an animal cell to thereby express and produce the humanized antibody.

As the CH of the humanized antibody, any CH can be used, so long as it belongs to the hIg class, and those of the hIgG class are preferred and any one of the subclasses belonging to the hIgG class, such as hIgG1, hIgG2, hIgG3 and hIgG4 can be used. As the CL of the humanized antibody, any CL can be used, so long as it belongs to the hIg class, and those belonging to the κ class or λ class can be used.

Examples of the humanized antibody of the present invention include a humanized antibody wherein CDRs 1 to 3 of VH of the antibody comprise the amino acid sequences represented by SEQ ID NOs:51 to 53, respectively, and CDRs 1 to 3 of VL of the antibody comprise the amino acid sequences represented by SEQ ID NOs:54 to 56, respectively; a humanized antibody wherein CDRs 1 to 3 of VH of the antibody comprise the amino acid sequences represented by SEQ ID NOs:27 to 29, respectively, and CDRs 1 to 3 of VL of the antibody comprise the amino acid sequences represented by SEQ ID NOs:30 to 32, respectively; a humanized antibody wherein CDRs 1 to 3 of VH of the antibody comprise the amino acid sequences represented by SEQ ID NOs:33 to 35, respectively, and CDRs 1 to 3 of VL of the antibody comprise the amino acid sequences represented by SEQ ID NOs:36 to 38, respectively; a humanized antibody wherein CDRs 1 to 3 of VH of the antibody comprise the amino acid sequences represented by SEQ ID NOs:39 to 41, respectively, and CDRs 1 to 3 of VL of the antibody comprise the amino acid sequences represented by SEQ ID NOs:42 to 44, respectively; a humanized antibody wherein CDRs 1 to 3 of VH of the antibody comprise the amino acid sequences represented by SEQ ID NOs:45 to 47, respectively, and CDRs 1 to 3 of VL of the antibody comprise the amino acid sequences represented by SEQ ID NOs:48 to 50, respectively; and the like.

Moreover, specific examples of the humanized antibody of the present invention include the following humanized antibodies:

with regard to the amino acid sequence of VH of the antibody, a humanized antibody wherein VH of the antibody has an amino acid sequence in which Leu at position 18, Val at position 93, Ala at position 97 and Thr at position 114 in the amino acid sequence represented by SEQ ID NO:77 are substituted with other amino acid residues, preferably, a humanized antibody wherein VH of the antibody has an amino acid sequence in which Val at position 93, Ala at position 97 and Thr at position 114 in the amino acid sequence represented by SEQ ID NO:77 are substituted with other amino acid residues, preferably, a humanized antibody wherein VH of the antibody has an amino acid sequence in which Leu at position 18, Ala at position 97 and Thr at position 114 in the amino acid sequence represented by SEQ ID NO:77 are substituted with other amino acid residues, preferably, a humanized antibody having an amino acid sequence in which Ala at position 97 and Thr at position 114 are substituted with other amino acid residues, and the like.

The amino acid sequence of VH of the antibody obtained by the above amino acid modifications include an amino acid sequence in which at least one modification selected from among amino acid modifications for substituting Leu at position 18 with Met, Val at position 93 with Thr, Ala at position 97 with Thr, and Thr at position 114 with Ile is introduced in the amino acid sequence represented by SEQ ID NO:77.

A specific example of the amino acid sequence of VH in which four modifications are introduced include an amino acid sequence in which substitutions of Leu at position 18 with Met, Val at position 93 with Thr, Ala at position 97 with Thr, and Thr at position 114 with Ile are introduced in the amino acid sequence represented by SEQ ID NO:77.

Specific examples of the amino acid sequence of VH in which three modifications are introduced in the amino acid sequence represented by SEQ ID NO:77 include the following amino acid sequences:

an amino acid sequence in which substitutions of Val at position 93 with Thr, Ala at position 97 with Thr, and Thr at position 114 with Ile are introduced, an amino acid sequence in which substitutions of Leu at position 18 with Met, Ala at position 97 with Thr, and Thr at position 114 with Ile are introduced, an amino acid sequence in which substitutions of Leu at position 18 with Met, Val at position 93 with Thr, and Thr at position 114 with Ile are introduced, an amino acid sequence in which substitutions of Leu at position 18 with Met, Val at position 93 with Thr, and Ala at position 97 with Thr are introduced, and the like.

Specific examples of the amino acid sequence of VH in which two modifications are introduced in the amino acid sequence represented by SEQ ID NO:77 include the following amino acid sequences:

an amino acid sequence in which substitutions of Leu at position 18 with Met, and Val at position 93 with Thr are introduced, an amino acid sequence in which substitutions of Leu at position 18 with Met, and Ala at position 97 with Thr are introduced, an amino acid sequence in which substitutions of Leu at position 18 with Met, and Thr at position 114 with Ile are introduced, an amino acid sequence in which substitutions of Val at position 93 with Thr, and Ala at position 97 with Thr are introduced, an amino acid sequence in which substitutions of Val at position 93 with Thr, and Thr at position 114 with Ile are introduced, an amino acid sequence in which substitutions of Ala at position 97 with Thr, and Thr at position 114 with Ile are introduced, and the like.

Specific examples of the amino acid sequence of VH in which one modification is introduced in the amino acid sequence represented by SEQ ID NO:77 include the following amino acid sequences:

an amino acid sequence in which a substitution of Leu at position 18 with Met is introduced, an amino acid sequence in which a substitution of Val at position 93 with Thr is introduced, an amino acid sequence in which a substitution of Ala at position 97 with Thr is introduced, and an amino acid sequence in which a substitution of Thr at position 114 with Ile is introduced.

With regard to VL of the antibody, examples include an amino acid sequence in which Ala at position 13, Val at position 15, Val at position 19, Ala at position 47, Val at position 62, and Leu at position 82 in the amino acid sequence represented by SEQ ID NO:78 are substituted with other amino acid residues.

Preferred is an amino acid sequence in which Ala at position 13, Val at position 19, Val at position 62, and Leu at position 82 in the amino acid sequence represented by SEQ ID NO:78 are substituted with other amino acid residues.

The amino acid sequence of VL obtained by the above amino acid modifications include an amino acid sequence in which at least one modification selected from among amino acid modifications for substituting Ala at position 13 with Val, Val at position 15 with Leu, Val at position 19 with Ala, Ala at position 47 with Gln, Val at position 62 with Ile, and Leu at position 82 with Val is introduced in the amino acid sequence represented by SEQ ID NO:78.

Specific examples of the amino acid sequence of VL in which six modifications are introduced include an amino acid sequence in which substitutions of Ala at position 13 with Val, Val at position 15 with Leu, Val at position 19 with Ala, Ala at position 47 with Gln, Val at position 62 with Ile, and Leu at position 82 with Val are introduced in the amino acid sequence represented by SEQ ID NO:78, and the like.

Specific examples of the amino acid sequence of VL in which five modifications are introduced in the amino acid sequence represented by SEQ ID NO:78 include the following amino acid sequences:

an amino acid sequence in which substitutions of Ala at position 13 with Val, Val at position 15 with Leu, Val at position 19 with Ala, Ala at position 47 with Gln, and Val at position 62 with Ile are introduced, an amino acid sequence in which substitutions of Ala at position 13 with Val, Val at position 15 with Leu, Val at position 19 with Ala, Ala at position 47 with Gln, and Leu at position 82 with Val are introduced, an amino acid sequence in which substitutions of Ala at position 13 with Val, Val at position 15 with Leu, Val at position 19 with Ala, Val at position 62 with Ile, and Leu at position 82 with Val are introduced, an amino acid sequence in which substitutions of Ala at position 13 with Val, Val at position 15 with Leu, Ala at position 47 with Gln, Val at position 62 with Ile, and Leu at position 82 with Val are introduced, an amino acid sequence in which substitutions of Ala at position 13 with Val, Val at position 19 with Ala, Ala at position 47 with Gln, Val at position 62 with Ile, and Leu at position 82 with Val are introduced, an amino acid sequence in which substitutions of Val at position 15 with Leu, Val at position 19 with Ala, Ala at position 47 with Gln, Val at position 62 with Ile, and Leu at position 82 with Val are introduced, and the like.

Specific examples of the amino acid sequence of VL in which four modifications are introduced in the amino acid sequence represented by SEQ ID NO:78 include the following amino acid sequences:

an amino acid sequence in which substitutions of Ala at position 13 with Val, Val at position 15 with Leu, Val at position 19 with Ala, and Ala at position 47 with Gln are introduced, an amino acid sequence in which substitutions of Ala at position 13 with Val, Val at position 15 with Leu, Val at position 19 with Ala, and Val at position 62 with Ile are introduced, an amino acid sequence in which substitutions of Ala at position 13 with Val, Val at position 15 with Leu, Val at position 19 with Ala, and Leu at position 82 with Val are introduced, an amino acid sequence in which substitutions of Ala at position 13 with Val, Val at position 15 with Leu, Ala at position 47 with Gln, and Val at position 62 with Ile are introduced, an amino acid sequence in which substitutions of Ala at position 13 with Val, Val at position 15 with Leu, Ala at position 47 with Gln, and Leu at position 82 with Val are introduced, an amino acid sequence in which substitutions of Ala at position 13 with Val, Val at position 15 with Leu, Val at position 62 with Ile, and Leu at position 82 with Val are introduced, an amino acid sequence in which substitutions of Ala at position 13 with Val, Val at position 19 with Ala, Ala at position 47 with Gln, and Val at position 62 with Ile are introduced, an amino acid sequence in which substitutions of Ala at position 13 with Val, Val at position 19 with Ala, Ala at position 47 with Gln, and Leu at position 82 with Val are introduced, an amino acid sequence in which substitutions of Ala at position 13 with Val, Val at position 19 with Ala, Val at position 62 with Ile, and Leu at position 82 with Val are introduced, an amino acid sequence in which substitutions of Val at position 15 with Leu, Val at position 19 with Ala, Ala at position 47 with Gln, and Val at position 62 with Ile are introduced, an amino acid sequence in which substitutions of Val at position 15 with Leu, Val at position 19 with Ala, Ala at position 47 with Gln, and Leu at position 82 with Val are introduced, an amino acid sequence in which substitutions of Val at position 15 with Leu, Val at position 19 with Ala, Val at position 62 with Ile, and Leu at position 82 with Val are introduced, an amino acid sequence in which substitutions of Val at position 19 with Ala, Ala at position 47 with Gln, Val at position 62 with Ile, and Leu at position 82 with Val are introduced, and the like.

Specific examples of the amino acid sequence of VL in which three modifications are introduced in the amino acid sequence represented by SEQ ID NO:78 include the following amino acid sequences:

an amino acid sequence in which substitutions of Ala at position 13 with Val, Val at position 15 with Leu, and Val at position 19 with Ala are introduced, an amino acid sequence in which substitutions of Ala at position 13 with Val, Val at position 15 with Leu, and Ala at position 47 with Gln are introduced, an amino acid sequence in which substitutions of Ala at position 13 with Val, Val at position 15 with Leu, and Val at position 62 with Ile are introduced, an amino acid sequence in which substitutions of Ala at position 13 with Val, Val at position 15 with Leu, and Leu at position 82 with Val are introduced, an amino acid sequence in which substitutions of Ala at position 13 with Val, Val at position 19 with Ala, and Ala at position 47 with Gln are introduced, an amino acid sequence in which substitutions of Ala at position 13 with Val, Val at position 19 with Ala, and Val at position 62 with Ile are introduced, an amino acid sequence in which substitutions of Ala at position 13 with Val, Val at position 19 with Ala, and Leu at position 82 with Val are introduced, an amino acid sequence in which substitutions of Ala at position 13 with Val, Ala at position 47 with Gln, and Val at position 62 with Ile are introduced, an amino acid sequence in which substitutions of Ala at position 13 with Val, Ala at position 47 with Gln, and Leu at position 82 with Val are introduced, an amino acid sequence in which substitutions of Val at position 15 with Leu, Val at position 19 with Ala, and Ala at position 47 with Gln are introduced, an amino acid sequence in which substitutions of Val at position 15 with Leu, Val at position 19 with Ala, and Val at position 62 with Ile are introduced, an amino acid sequence in which substitutions of Val at position 15 with Leu, Val at position 19 with Ala, and Leu at position 82 with Val are introduced, an amino acid sequence in which substitutions of Val at position 15 with Leu, Ala at position 47 with Gln, and Val at position 62 with Ile are introduced, an amino acid sequence in which substitutions of Val at position 15 with Leu, Ala at position 47 with Gln, and Leu at position 82 with Val are introduced, an amino acid sequence in which substitutions of Val at position 19 with Ala, Ala at position 47 with Gln, and Val at position 62 with Ile are introduced, an amino acid sequence in which substitutions of Val at position 19 with Ala, Ala at position 47 with Gln, and Leu at position 82 with Val are introduced, an amino acid sequence in which substitutions of Ala at position 47 with Gln, Val at position 62 with Ile, and Leu at position 82 with Val are introduced, and the like.

Specific examples of the amino acid sequence of VL in which two modifications are introduced in the amino acid sequence represented by SEQ ID NO:78 include the following amino acid sequences:

an amino acid sequence in which substitutions of Ala at position 13 with Val, and Val at position 15 with Leu are introduced, an amino acid sequence in which substitutions of Ala at position 13 with Val, and Val at position 19 with Ala are introduced, an amino acid sequence in which substitutions of Ala at position 13 with Val, and Ala at position 47 with Gln are introduced, an amino acid sequence in which substitutions of Ala at position 13 with Val, and Val at position 62 with Ile are introduced, an amino acid sequence in which substitutions of Ala at position 13 with Val, and Leu at position 82 with Val are introduced, an amino acid sequence in which substitutions of Val at position 15 with Leu, and Val at position 19 with Ala are introduced, an amino acid sequence in which substitutions of Val at position 15 with Leu, and Ala at position 47 with Gln are introduced, an amino acid sequence in which substitutions of Val at position 15 with Leu, and Val at position 62 with Ile are introduced, an amino acid sequence in which substitutions of Val at position 15 with Leu, and Leu at position 82 with Val are introduced, an amino acid sequence in which substitutions of Val at position 19 with Ala, and Ala at position 47 with Gln are introduced, an amino acid sequence in which substitutions of Val at position 19 with Ala, and Val at position 62 with Ile are introduced, an amino acid sequence in which substitutions of Val at position 19 with Ala, and Leu at position 82 with Val are introduced, an amino acid sequence in which substitutions of Ala at position 47 with Gln, and Val at position 62 with Ile are introduced, an amino acid sequence in which substitutions of Ala at position 47 with Gln, and Leu at position 82 with Val are introduced, an amino acid sequence in which substitutions of Val at position 62 with Ile, and Leu at position 82 with Val are introduced, and the like.

Specific examples of the amino acid sequence of VL in which one modification is introduced in the amino acid sequence represented by SEQ ID NO:78 include the following amino acid sequences:

an amino acid sequence in which a substitution of Ala at position 13 with Val is introduced, an amino acid sequence in which a substitution of Val at position 15 with Leu is introduced, an amino acid sequence in which a substitution of Val at position 19 with Ala is introduced, an amino acid sequence in which a substitution of Ala at position 47 with Gln is introduced, an amino acid sequence in which a substitution of Val at position 62 with Ile is introduced, an amino acid sequence in which a substitution of Leu at position 82 with Val is introduced, and the like.

Specific example of the humanized antibody of the present invention includes a humanized antibody in which VH comprises the amino acid sequence represented by one selected from SEQ ID NOs:77, 96, 98 and 100, and/or VL comprises the amino acid sequence represented by one selected from SEQ ID NOs:78 and 102. Furthermore, specific example of the humanized antibody of the present invention specifically include a humanized antibody in which H chain of variable region comprises the amino acid sequence represented by SEQ ID No:77 and/or L chain of variable region comprises the amino acid sequence represented by SEQ ID No:78; a humanized antibody in which VH comprises the amino acid sequence represented by SEQ ID No:96 and/or VL comprises the amino acid sequence represented by SEQ ID No:78; a humanized antibody in which VH comprises the amino acid sequence represented by SEQ ID No:98 and/or VL comprises the amino acid sequence represented by SEQ ID No:78; a humanized antibody in which VH comprises the amino acid sequence represented by SEQ ID No:100 and/or VL comprises the amino acid sequence represented by SEQ ID No:78; a humanized antibody in which VH comprises the amino acid sequence represented by SEQ ID No:100 and/or VL comprises the amino acid sequence represented by SEQ ID No:102; and the like.

In addition, examples of the humanized antibody of the present invention include a humanized antibody which competes with the above humanized antibody in the binding of the extracellular region of CD4 and a humanized antibody which binds to the same epitope as an epitope in an extracellular region of CD4 to which the above humanized antibody binds.

A human antibody is originally an antibody naturally existing in the human body, and it also includes an antibody obtained from a human antibody phage library or a human antibody-producing transgenic animal, which is prepared based on the recent advanced techniques in genetic engineering, cell engineering and developmental engineering.

The antibody existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the supernatant of the culture.

The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques.

A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it. A human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the supernatant of the culture.

In the amino acid sequence constituting the above antibody or antibody fragment, a monoclonal antibody or antibody fragment thereof in which one or more amino acids are deleted, substituted, inserted or added, having activity similar to the above antibody or antibody fragment is also included in the monoclonal antibody or antibody fragment of the present invention.

The number of amino acids which are deleted, substituted, inserted and/or added is one or more, and is not specifically limited, but it is within the range where deletion, substitution or addition is possible by known methods such as the site-directed mutagenesis [*Molecular Cloning* 2nd Edition, Cold Spring Harbor Laboratory Press (1989), *Current protocols in Molecular Biology*, John Wiley & Sons (1987-1997), *Nucleic Acids Research*, 10, 6487 (1982), *Proc. Natl. Acad. Sci., USA*, 79, 6409 (1982), *Gene*, 34, 315 (1985), *Nucleic Acids Research*, 13, 4431 (1985), *Proc. Natl. Acad. Sci USA*, 82, 488 (1985)] or the like. For example, the number is 1 to dozens, preferably 1 to 20, more preferably 1 to 10, and most preferably 1 to 5.

The expression "one or more amino acids are deleted, substituted, inserted or added" in the amino acid sequence of the above antibody means the followings. That is, it means there is deletion, substitution, insertion or addition of one or plural amino acids at optional positions in the same sequence and one or plural amino acid sequences. Also, the deletion, substitution, insertion or addition may occur at the same time and the amino acid which is substituted, inserted or added may be either a natural type or a non-natural type. The natural type amino acid includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The antibody fragment of the present invention includes Fab, $F(ab')_2$, Fab', scFv, diabody, dsFv, a peptide comprising CDR and the like.

An Fab is an antibody fragment having a molecular weight of about 50,000 and having antigen binding activity, in which about a half of the N-terminal side of H chain and the entire L chain, among fragments obtained by treating an IgG antibody molecule with a protease, papain (cleaved at an amino acid residue at position 224 of the H chain), are bound together through a disulfide bond.

An $F(ab')_2$ is an antibody fragment having a molecular weight of about 100,000 and antigen binding activity and comprising two Fab regions which are bound in the hinge position obtained by digesting the lower part of two disulfide bonds in the hinge region of IgG, with an enzyme, pepsin. The $F(ab')_2$ of the present invention can be produced by treating a monoclonal antibody which specifically recognizes CD4 and binds to the extracellular region with a protease, pepsin. Also, the $F(ab')_2$ can be also produced by binding Fab' described below via a thioether bond or a disulfide bond.

An Fab' is an antibody fragment having a molecular weight of about 50,000 and antigen binding activity, which is obtained by cleaving a disulfide bond at the hinge region of the above $F(ab')_2$. The Fab' of the present invention can be produced by $F(ab')_2$ which specifically recognizes CD4 and binds to the extracellular region, with a reducing agent, such as dithiothreitol. Also, the Fab' can be produced by inserting DNA encoding Fab' fragment of the antibody into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (hereinafter referred to as "P") and is an antibody fragment having antigen binding activity. The scFv of the present invention can be produced by obtaining cDNAs encoding VH and VL of a monoclonal antibody which specifically recognizes CD4 and binds to the extracellular region, constructing DNA encoding scFv, inserting the DNA into an expression vector for prokaryote or an expression vector for eukaryote, and then introducing the expression vector into a prokaryote or eukaryote to express the scFv.

A diabody is an antibody fragment wherein scFv is dimerized, is an antibody fragment having divalent antigen binding activity. In the divalent antigen binding activity, two antigens may be the same or different. The diabody of the present invention can be produced by obtaining cDNAs encoding VH and VL of a monoclonal antibody which specifically recognizes CD4 and binds to the extracellular region, constructing DNA encoding scFv so that the length of the amino acid sequence of the peptide linker is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with a known methods [*Protein Engineering*, 7, 697 (1994)]. The dsFv of the present invention can be produced by obtaining cDNAs encoding VH and VL of a monoclonal antibody which specifically recognizes CD4 and binds to the extracellular region, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including one or more regions of CDRs of VH or VL. Peptide comprising plural CDRs can be bound directly or via an appropriate peptide linker. The peptide comprising CDR of the present invention can be produced by constructing DNA encoding CDRs of VH and VL of a monoclonal antibody which specifically recognizes CD4 and binds to the extracellular region, inserting the DNA into an expression vector for prokaryote or an expression vector for eukaryote, and then introducing the expression vector into a prokaryote or eukaryote to express the peptide. The peptide comprising CDR can also be produced by a chemical synthesis method such as Fmoc method or tBoc method.

The monoclonal antibody of the present invention includes an antibody conjugate in which a monoclonal antibody or an antibody fragment thereof which specifically recognizes a three-dimensional structure of an extracellular region of CD4 and binds to the extracellular region is chemically or genetically bound to a radioisotope, an agent having a low molecular weight, an agent having a high molecular weight, a protein, a therapeutic antibody or the like.

The antibody conjugate of the present invention can be produced by chemically conjugating a radioisotope, an agent having a low molecular weight, an agent having a high molecular weight, a protein, a therapeutic antibody or the like to the N-terminal side or C-terminal side of an H chain or an L chain of the monoclonal antibody or the antibody fragment thereof, an appropriate substituent or side chain of the antibody or the antibody fragment, a sugar chain in the antibody or the antibody fragment or the like, which specifically recognizes a three-dimensional structure of an extracellular region of CD4 and binds to the extracellular region in the present invention [*Antibody Engineering Handbook*, published by Chijin Shokan (1994)].

Also, the antibody conjugate can be genetically produced by linking a DNA encoding the monoclonal antibody or the antibody fragment thereof which specifically recognizes three-dimensional structure of an extracellular region of CD4 and binds to the extracellular region in the present invention to other DNA encoding a protein or a therapeutic antibody to be conjugated, inserting the DNA into a vector for expression, and introducing the expression vector into an appropriate host cell.

The radioisotope includes $^{131}$I, $^{125}$I, $^{90}$Y, $^{64}$Cu, $^{99}$Tc, $^{77}$Lu, $^{211}$At and the like. The radioisotope can directly be conjugated with the antibody by Chloramine-T method. Also, a substance chelating the radioisotope can be conjugated with the antibody. The chelating agent includes 1-isothiocyanatebenzyl-3-methyldiethylene-triaminepentaacetic acid (MX-DTPA) and the like.

The agent having a low molecular weight includes an antitumor agent such as an alkylating agent, a nitrosourea agent, a metabolism antagonist, an antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor [*Rinsho Syuyogaku* (Clinical Oncology), Gan to Kagaguryoho-Sha (1996)], a steroid agent such as hydrocortisone and prednisone, a nonsteroidal agent such as aspirin and indomethacin, immune-regulating agent such as aurothiomalate, penicillamine, immuno-suppressing agent such as cyclophosphamide and azathioprine, anti-inflammatory agent such as anti-histamine agent, for example, chlorpheniramine maleate and clemastine [*Ensho to Kouensho-Ryoho* (*Inflammation and Anti-inflammation Therapy*), Ishiyaku Shuppann (1982)] and the like. Examples of the antitumor agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), epirubicin, gemcitabine (Gemsal), daunorubicin, procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, iphosphamide, idarubicin, mesna, irinotecan (CPT-11), nogitecan, mitoxantrone, topotecan, leuprolide, megestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, FMS-like tyrosine kinase 3 (Flt3) inhibitor, vascular endothelial growth factor receptor (VEGFR) inhibitor, fibroblast growth factor receptor (FGFR) inhibitor, epidermal growth factor receptor (EGFR) inhibitor such as Iressa and Tarceva, radicicol, 17-allylamino-17-demethoxygeldanamycin, rapamycin, amsacrine, all-trans-retinoic acid, thalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestin substances, estrogen substances, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, voltezomib, allopurinol, calicheamicin, ibritumomab tiuxetan, Targretin, ozogamine, clarithromycin, leucovorin, ifosfamide, ketoconazole, aminoglutethimide, suramin, methotrexate, maytansinoid and derivatives thereof.

The method for conjugating the agent having low molecular weight with the antibody includes a method in which the agent and an amino group of the antibody are conjugated through glutaraldehyde, a method in which an amino group of the agent and a carboxyl group of the antibody are conjugated through water-soluble carbodiimide, and the like.

The agent having a high molecular weight includes polyethylene glycol (hereinafter referred to as "PEG"), albumin, dextran, polyoxyethylene, styrene-maleic acid copolymer, polyvinylpyrrolidone, pyran copolymer, hydroxypropyl-methacrylamide, and the like. By binding these compounds having a high molecular weight to an antibody or antibody fragment, the following effects are expected: (1) improvement of stability against various chemical, physical or biological factors, (2) remarkable prolongation of half life in blood, (3) disappearance of immunogenicity, suppression of antibody production, and the like [*Bioconjugate Drug,* Hirokawa Shoten (1993)]. For example, the method for binding PEG to an antibody includes a method in which an antibody is allowed to react with a PEG-modifying reagent [*Bioconjugate Drug,* Hirokawa Shoten (1993)]. The PEG-modifying reagent includes a modifying agent of ε-amino group of lysine (Japanese Published Unexamined Patent Application No. 178926/86), a modifying agent of a carboxyl group of aspartic acid and glutamic acid (Japanese Published Unexamined Patent Application No. 23587/81), a modifying agent of a guanidino group of arginine (Japanese Published Unexamined Patent Application No. 117920/90) and the like.

The immunostimulator may be any natural products known as immunoadjuvants. Examples of an agent enhancing immunogen include β(1→3)glucan (lentinan, schizophyllan), α-galactosylceramide and the like.

The protein includes a cytokine or a growth factor which activates a immunocompetent cell, such as NK cell, macrophage or neutrophil, a toxic protein, and the like.

Examples of the cytokine or the growth factor include interferon (hereinafter referred to as "INF")-α, INF-β, INF-γ, interleukin (hereinafter referred to as "IL")-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) and the like. The toxic protein includes ricin, diphtheria toxin, ONTAK and the like, and also includes a toxic protein wherein mutation is introduced into a protein in order to control the toxicity.

The therapeutic antibody includes an antibody against an antigen in which apoptosis is induced by binding of the antibody, an antibody against an antigen participating in formation of pathologic state of tumor, an antibody which regulates immunological function and an antibody relating to angiogenesis in the pathologic part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, epidermal growth factor receptor (EGFR) and the like.

The antigen for the antibody which regulates immunological function includes CD40, CD40 ligand, B7 family molecule (CD80, CD86, CD274, B7-DC, B7-H2, B7-H3, B7-H4), ligand of B7 family molecule (CD28, CTLA-4, ICOS, PD-1, BTLA), OX-40, OX-40 ligand, CD137, tumor necrosis factor (TNF) receptor family molecule (DR4, DR5, TNFR1, TNFR2), TNF-related apoptosis-inducing ligand receptor (TRAIL) family molecule, receptor family of TRAIL family molecule (TRAIL-R1, TRAIL-R2, TRAIL-R3, TRAIL-R4), receptor activator of nuclear factor kappa B ligand (RANK), RANK ligand, CD25, folic acid receptor 4, cytokine [IL-1α, IL-1β, IL-4, IL-5, IL-6, IL-10, IL-13, transforming growth factor (TGF) β, TNFα, etc.], receptors of these cytokines, chemokine (SLC, ELC, I-309, TARC, MDC, CTACK, etc.) and receptors of these chemokines.

The antigen for the antibody which inhibits angiogenesis in the pathologic part includes vascular endothelial growth factor (VEGF), angiopoietin, fibroblast growth factor (FGF), EGF, platelet-derived growth factor (PDGF), insulin-like growth factor (IGF), erythropoietin (EPO), TGFβ, IL-8, Ephilin, SDF-1, receptors thereof and the like.

A fusion antibody with a protein or therapeutic antibody can be produced by linking a cDNA encoding a monoclonal antibody or an antibody fragment to a cDNA encoding the protein, constructing a DNA encoding the fusion antibody, inserting the DNA into an expression vector for prokaryote or eukaryote, and then introducing the expression vector into a prokaryote or eukaryote to express the fusion antibody.

In the case where the above antibody conjugate is used for the detecting method, method for quantitative determination, detection reagent, reagent for quantitative determination or diagnostic agent in the present invention, examples of the agent to which a monoclonal antibody or an antibody fragment thereof of the present invention which specifically recognizes an extracellular region of CD4 and binds to the extracellular region is bound includes a label used in routine immunological detecting or measuring method. The label includes enzymes such as alkaline phosphatase, peroxidase and luciferase, luminescent materials such as acridinium ester and lophine, fluorescent materials such as fluorescein isothiocyanate (FITC) and tetramethyl rhodamine isothiocyanate (RITC), and the like.

In addition, the present invention relates to a therapeutic agent for a disease relating to a CD4-positive cell which comprises a monoclonal antibody which specifically recognizes an extracellular region of CD4 and also binds to the extracellular region, or an antibody fragment thereof as an active ingredient.

The CD4-positive cell-associated disease may be any disease so long as it is a disease relating to a cell that expresses CD4, and examples include cancer, autoimmune diseases, allergic diseases, and infections.

Examples of the CD4-positive cell include a CD4-positive T cell such as Th1 cell, Th2 cell, or Th17 cell, a regulatory T cell (referred to also as "regulatory T cell"), a γδT cell, and the like. Further, examples of a CD4-positive cell which relates to a disease include cancer, an inflammatory disease, i.e., autoimmune disease, or an allergic disease, based on the fact that CD4 is expressed in an abnormal cell responsible for such a disease.

The cancer includes blood cancer, breast cancer, uterine cancer, colorectal cancer, esophageal cancer, stomach cancer, ovarian cancer, lung cancer, renal cancer, rectal cancer, thyroid cancer, uterine cervix cancer, small intestinal cancer, prostate cancer and pancreatic cancer. Preferable examples of the cancer include blood cancer, esophageal cancer, stomach cancer, colorectal cancer, liver cancer and prostate cancer. Examples of blood cancer include Cutaneous T cell lymphoma (CTCL), peripheral T cell lymphoma (PTCL), Anaplastic large cell lymphoma (ALCL), other lymphoid leukemia, myeloid leukemia, multiple myeloma, Hodgkin's lymphoma and non-Hodgkin's lymphoma.

Examples of the autoimmune disease includes rheumatoid arthritis, psoriasis, Crohn's disease, ankylosing spondylitis, multiple sclerosis, type I diabetes, hepatitis, myocarditis, Sjogren's syndrome, rejection after transplantation and the like.

Examples of the allergic disease include acute or chronic reactive airway disease, bronchial asthma, atopic dermatitis, allergic rhinitis and the like.

Examples of the infectious disease include human immunodeficiency virus (HIV) infection and the like.

The therapeutic agent in the present invention includes a therapeutic agent comprising the above monoclonal antibody or an antibody fragment of the present invention as an active ingredient.

The therapeutic agent comprising the antibody or antibody fragment thereof, or conjugate thereof of the present invention may comprise only the antibody or antibody fragment thereof, or conjugate thereof as an active ingredient. It is generally preferred that the therapeutic agent is prepared as a pharmaceutical preparation produced by an appropriate method well known in the technical field of pharmaceutics, and by mixing it with one or more pharmaceutically acceptable carriers.

It is preferred to administer the therapeutic agent by the route that is most effective for the treatment. Examples include oral administration and parenteral administration, such as buccal, tracheal, rectal, subcutaneous, intramuscular or intravenous administration and intravenous administration is preferred.

The therapeutic agent may be in the form of spray, capsules, tablets, granules, powder, syrup, emulsion, suppository, injection, ointment, tape, and the like.

Although the dose or the frequency of administration varies depending on the objective therapeutic effect, administration method, treating period, age, body weight and the like, it is usually 10 µg/kg to 10 mg/kg per day and per adult.

Further, the present invention relates to a method for immunologically detecting or measuring CD4, an agent for immunologically detecting or measuring CD4, a method for immunologically detecting or measuring a cell expressing CD4, an agent for immunologically detecting or measuring a CD4-expressing cell, and an agent for diagnosing a disease relating to a CD4-positive cell, comprising a monoclonal antibody or an antibody fragment thereof which specifically recognizes an extracellular region of CD4 and binds to the extracellular region, as an active ingredient.

As a method for detection or determination of the amount of CD4 in the present invention, any known method may be included. For example, an immunological detecting or measuring method may be exemplified.

An immunological detecting or measuring method is a method in which an antibody amount or an antigen amount is detected or determined using a labeled antigen or antibody. Examples of the immunological detecting or measuring method are radioactive substance-labeled immunoantibody method (RIA), enzyme immunoassay (EIA or ELISA), fluorescent immunoassay (FIA), luminescent immunoassay, Western blotting method, physico-chemical means and the like.

The above disease relating to CD4 can be diagnosed by detecting or measuring a cell expressing CD4 by using the monoclinal antibody or antibody fragment of the present invention.

For the detection of the cell expressing CD4, known immunological detecting methods can be used, and an immunoprecipitation method, a fluorescent cell staining method, an immune tissue staining method and the like are preferably used. In addition, a fluorescent antibody staining method using FMAT 8100 HTS system (Applied Biosystem) and the like can be used.

In the present invention, the living body sample to be used for detecting or measuring CD4 is not particularly limited, so long as it has a possibility of containing the polypeptide, such as tissue cells, blood, blood plasma, serum, pancreatic fluid, urine, fecal matter, tissue fluid or culture fluid.

The diagnostic agent containing the monoclonal antibody or an antibody fragment thereof, or conjugate thereof may further contain a reagent for carrying out an antigen-antibody reaction or a reagent for detection of the reaction depending on the desired diagnostic method. The reagent for carrying out the antigen-antibody reaction includes a buffer, a salt, and the like. The reagent for detection includes a reagent generally used for the immunological detecting or measuring method, such as labeled secondary antibody which recognizes the monoclonal antibody, antibody fragment thereof or conjugates thereof and substrate corresponding to the labeling.

A process for producing the antibody of the present invention, a method for treating the disease and a method for diagnosing the disease are specifically described below.

1. Preparation Method of Monoclonal Antibody
(1) Preparation of Antigen

CD4 or a cell expressing CD4 as an antigen can be obtained by introducing an expression vector comprising cDNA encoding a full length of CD4 or a partial length thereof is introduced into *Escherichia coli,* yeast, an insect cell, an animal cell or the like. In addition, CD4 can be purified from various human tumor cell lines, human tissue and the like which express a large amount of CD4. The tumor cell line and the tissue can be allowed to use as antigens. Furthermore, a synthetic peptide having a partial sequence of the CD4 can be prepared by a chemical synthesis method such as Fmoc method or tBoc method and used as an antigen.

CD4 used in the present invention can be produced, for example, by expressing a DNA encoding CD4 in a host cell using a method described in *Molecular Cloning, A Laboratory Manual,* Second Edition, Cold Spring Harbor Laboratory Press (1989), *Current Protocols in Molecular Biology,* John Wiley & Sons (1987-1997) or the like according to the following method.

Firstly, a recombinant vector is prepared by inserting a full length cDNA comprising the region encoding CD4 into downstream of a promoter of an appropriate expression vector. At this time, if necessary, a DNA fragment having an appropriate length containing a region encoding the polypeptide based on the full length cDNA, and the DNA fragment may be used instead of the above full length cDNA. Next, a transformant producing CD4 can be obtained by introducing the recombinant vector into a host cell suitable for the expression vector.

The expression vector includes vectors which can replicate autonomously in the host cell to be used or vectors which can be integrated into a chromosome comprising an appropriate promoter at such a position that the DNA encoding the polypeptide can be transcribed.

The host cell may be any one, so long as it can express the objective gene. Examples include a microorganism which belongs to the genera *Escherichia,* such as *Escherichia coli,* yeast, an insect cell, an animal cell and the like.

When a prokaryote such as *Escherichia coli* is used as the host cell, it is preferred that the recombinant vector used in the present invention is autonomously replicable in the prokaryote and comprises a promoter, a ribosome binding sequence, the DNA comprising the portion encoding CD4 and a transcription termination sequence. The recombinant vector is not necessary to have a transcription termination sequence, but a transcription termination sequence is preferably set just below the structural gene. The recombinant vector may further comprise a gene regulating the promoter.

Also, the above recombinant vector is preferably a plasmid in which the space between Shine-Dalgarno sequence (also referred to as SD sequence), which is the ribosome binding sequence, and the initiation codon is adjusted to an appropriate distance (for example, 6 to 18 nucleotides).

Furthermore, the nucleotide sequence of the DNA encoding CD4 can be substituted with another base so as to be a suitable codon for expressing in a host cell, thereby improve the productivity of the objective CD4.

Any expression vector can be used, so long as it can function in the host cell to be used. Examples of the expression vector includes pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. Nos. 4,686,191, 4,939,094, 5,160,735), pSupex, pUB110, pTP5, pC194, pEG400 [*J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a promoter in which two Ptrp are linked in tandem, tac promoter, lacT7 promoter and letI promoter, can be used.

Examples of the host cell include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* DH5α and the like.

Any introduction method of the recombinant vector can be used, so long as it is a method for introducing DNA into the host cell, and examples include a method using a calcium ion [*Proc. Natl. Acad. Sci. USA*, 69, 2110 (1972), methods described in *Gene*, 17, 107 (1982) and *Molecular & General Genetics*, 168, 111 (1979)].

When an animal cell is used as the host cell, an expression vector can be used, so long as it can function in the animal cell. Examples include pcDNAI, pcDM8 (manufactured by Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840,(1987)], pcDNAI/Amp (manufactured by Invitrogen), pcDNA3.1 (manufactured by Invitrogen), pREP4 (manufactured by Invitrogen), pAGE103 [*J. Biochemistry*, 101, 1307 (1987)], pAGE210, pME18SFL3, pKANTEX93 (WO 97/10354) and the like.

Any promoter can be used, so long as it can function in an animal cell. Examples include a promoter of immediate early (IE) gene of cytomegalovirus (CMV), SV40 early promoter, a promoter of retrovirus, a metallothionein promoter, a heat shock promoter, SRα promoter, Molony murine leukemia virus promoter or enhancer, and the like. Also, the enhancer of the IE gene of human CMV can be used together with the promoter.

Examples of the host cell include human leukemia cell Namalwa cell, monkey COS cell, Chinese hamster ovary cell CHO cell (*Journal of Experimental Medicine*, 108, 945 (1958); *Proc. Natl. Acad. Sci. USA*, 60, 1275 (1968); *Genetics*, 55, 513 (1968); *Chromosoma*, 41, 129 (1973); *Methods in Cell Science*, 18, 115 (1996); *Radiation Research*, 148, 260 (1997); *Proc. Natl. Acad. Sci. USA*, 77, 4216 (1980); *Proc. Natl. Acad. Sci.*, 60, 1275 (1968); *Cell*, 6, 121 (1975); *Molecular Cell Genetics*, Appendix I, II (pp. 883-900)), CHO/DG44, CHO-K1 (ATCC CCL-61), DUkXB11 (ATCC CCL-9096), Pro-5 (ATCC CCL-1781), CHO-S (Life Technologies, Cat #11619), Pro-3 cell, rat myeloma YB2/3HL.P2.G11.16Ag.20 (also known as YB2/0), mouse myeloma cell NS0, mouse myeloma cell 5P2/0-Ag14, Syrian hamster cells BHK or HBT5637 (Japanese Published Unexamined Patent Application No. 000299/88) and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the like.

CD4 can be produced by culturing the transformant derived from a microorganism, an animal cell or the like having a recombinant vector comprising the DNA encoding CD4 in a medium to form and accumulate CD4 in the culture, and recovering it from the culture. The method for culturing the transformant in the medium is carried out according to the usual method used in culturing of hosts.

When CD4 is expressed in a cell derived from eukaryote, CD4 to which sugars or sugar chains bind can be obtained.

When a microorganism transformed with a recombinant vector containing an inducible promoter is cultured, an inducer can be added to the medium, if necessary. For example, isopropyl-β-D-thiogalactopyranoside or the like can be added to the medium when a microorganism transformed with a recombinant vector using lac promoter is cultured; or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)] and 199 medium [*Proceeding of the Society for the Biological Medicine*, 73, 1 (1950)], Iscoove's modified Dulbecco's medium (IMDM), the media to which fetal calf serum, etc. is added, and the like. The culturing is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Regarding the expression method of the gene encoding CD4, in addition to direct expression, secretory production, fusion protein expression and the like can be carried out according to the method described in *Molecular Cloning, A Laboratory Manual*, Second Edition, Cold Spring Harbor Laboratory Press (1989).

The process for producing CD4 includes a method of intracellular expression in a host cell, a method of extracellular secretion from a host cell, a method of producing on a host cell membrane outer envelope, and the like. The appropriate method can be selected by changing the host cell used and the structure of the CD4 produced.

When the CD4 is produced in a host cell or on a host cell membrane outer envelope, CD4 can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and WO 94/23021, and the like.

Also, the production amount of CD4 can be increased in accordance with the method described in Japanese Published Unexamined Patent Application No. 227075/90 utilizing a gene amplification system using a dihydrofolate reductase gene.

The resulting CD4 can be isolated and purified, for example, as follows.

When CD4 is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general enzyme isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When CD4 is expressed intracellularly by forming an inclusion body, the cells are recovered, disrupted and centrifuged in the same manner, and the inclusion body of CD4 are recovered as a precipitation fraction. The recovered inclusion body of the protein is solubilized with a protein denaturing agent. The protein is made into a normal three-dimensional structure by diluting or dialyzing the solubilized solution, and then a purified preparation of CD4 is obtained by the same isolation purification method as above.

When CD4 or the derivative such as a glycosylated product is secreted extracellularly, CD4 or the derivative such as a glycosylated product can be recovered from the culture supernatant. That is, the culture is treated by a method such as centrifugation in the same manner as above to obtain a culture supernatant, a purified preparation of CD4 can be obtained from the culture supernatant by the same isolation purification method as above.

Also, CD4 used in the present invention can be produced by a chemical synthesis method, such as Fmoc method or tBoc method. Also, it can be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(2) Immunization of Animal and Preparation of Antibody-Producing Cell for Fusion A mouse, rat or hamster 3 to 20 weeks old is immunized with the antigen prepared in the above (1), and antibody-producing cells are collected from the spleen, lymph node or peripheral blood of the animal. Also, when the increase of a sufficient titer in the above animal is recognized due to low immunogenicity, a CD4 knockout mouse may by used as an animal to be immunized.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies—A Laboratory Manual*, Cold Spring Harbor Laboratory (1988)] or the like. An animal showing a sufficient antibody titer in their sera against the antigen used for the immunization is used as the supply source of antibody-producing cells for fusion.

Three to seven days after final administration of the antigen, tissue containing the antibody-producing cells such as the spleen from the immunized animal is excised to collect the antibody-producing cells. When the spleen cells are used, the spleen is cut out and loosened, followed by centrifuged. Then, antibody-producing cells for fusion are obtained by removing erythrocytes.

(3) Preparation of Myeloma Cell

An established cell line obtained from mouse is used as myeloma cells. Examples include 8-azaguanine-resistant mouse (derived from BALB/c) myeloma cell line P3-X63Ag8-U1 (P3-U1) [*Current Topics in Microbiology and Immunology*, 18, 1 (1978)], P3-NS1/1-Ag41 (NS-1) [*European J. Immunology*, 6, 511 (1976)], SP2/0-Ag14 (SP-2) [*Nature*, 276, 269 (1978)], P3-X63-Ag8653 (653) [*J. Immunology*, 123, 1548 (1979)], P3-X63-Ag8 (X63) [*Nature*, 256, 495 (1975)] and the like.

The myeloma cells are subcultured in a normal medium [a medium in which glutamine, 2-mercaptoethanol, gentamicin, FBS and 8-azaguanine are added to RPMI1640 medium] and they are subcultured in the normal medium 3 or 4 days before cell fusion to ensure the cell number of $2 \times 10^7$ or more on the day for fusion.

(4) Cell Fusion and Preparation of Hybridoma for Producing Monoclonal Antibody

The antibody-producing cells for fusion obtained by the above (2) and myeloma cells obtained by the above (3) were sufficiently washed with a minimum essential medium (MEM) or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells: the myeloma cells=5 to 10:1, followed by centrifugation. Then, the supernatant is discarded. The precipitated cell group is sufficiently loosened. After loosening the precipitated cell, the mixture of polyethylene glycol-1000 (PEG-1000), MEM and dimethylsulfoxide is added to the cell under stirring at 37° C. In addition, 1 to 2 mL of MEM medium is added several times every one or two minutes, and MEM is added to give a total amount of 50 mL. After centrifugation, the supernatant is discarded. After the cells are gently loosen, the cells are gently suspended in HAT medium [a medium in which hypoxanthine, thymidine and aminopterin is added to the normal medium]. The suspension is cultured in a 5% $CO_2$ incubator for 7 to 14 days at 37° C.

After the culturing, a portion of the culture supernatant is sampled and a hybridoma which is reactive to an antigen containing CD4 and is not reactive to an antigen not containing CD4 is selected by binding assay as described below. Then, cloning is carried out twice by a limiting dilution method [Firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Purified Monoclonal Antibody

The hybridoma cells producing a monoclonal antibody obtained by the above (4) are administered by intraperitoneal injection into 8- to 10-week-old mice or nude mice treated with 0.5 mL of pristane (2,6,10,14-tetramethylpentadecane (pristane) is intraperitoneally administered, followed by feeding for 2 weeks). The hybridoma develops ascites tumor in 10 to 21 days. The ascitic fluid is collected from the mice, centrifuged to remove solids, subjected to salting out with 40 to 50% ammonium sulfate and then precipitated by caprylic acid, passed through a DEAE-Sepharose column, a protein A column or a gel filtration column to collect an IgG or IgM fraction as a purified monoclonal antibody.

Furthermore, a monoclonal antibody-producing hybridoma obtained by the above (4) is cultured in RPMI1640 medium containing FBS or the like and the supernatant is removed by centrifugation. The precipitated cells are suspended in Hybridoma SFM medium containing 5% DIGO GF21 and cultured for 3 to 7 days. The purified monoclonal antibody can be obtained by centrifusing the obtained cell suspension, followed by purifying the resulting supernatant with Protein A column or Protein G column to collect the IgG fractions.

The subclass of the antibody can be determined using a subclass typing kit by enzyme immunoassay. The amount of the protein can be determined by the Lowry method or from the absorbance at 280 nm.

(6) Selection of Monoclonal Antibody

Selection of monoclonal antibody is carried out by the following binding assay using an enzyme immunoassay method and kinetic analysis with Biacore.

(6-a) Binding Assay

As the antigen, a gene-introduced cell or a recombinant protein obtained by introducing an expression vector containing a cDNA encoding CD4 obtained in (1) into *Escherichia coli,* yeast, an insect cell, an animal cell or the like, or a purified polypeptide or partial peptide obtained from a human tissue is used. When the antigen is a partial peptide, a conjugate is prepared with a carrier protein such as BSA or KLH and is used.

After making these antigens into a solid layer by dispensing in a 96-well plate, a substance to be tested such as serum, a culture supernatant of a hybridoma or a purified monoclonal antibody is dispensed therein as the primary antibody and allowed to react. After thoroughly washing with PBS or PBS-Tween, an anti-immunoglobulin antibody labeled with biotin, an enzyme, a chemiluminescent material, a radiation compound or the like is dispensed therein as the secondary antibody and allowed to react. After thoroughly washing with PBS-Tween, the reaction is carried out in response to the label of the secondary antibody to select a monoclonal antibody which specifically reacts with the antigen.

The antibody which competes with the anti-CD4 monoclonal antibody of the present invention can be prepared by adding an antibody to be tested to the above-mentioned binding assay system and carrying out reaction. That is, a monoclonal antibody which competes with the thus obtained monoclonal antibody for its binding to the extracellular region of CD4 can be prepared by carrying out a screening of an antibody by which the binding of the monoclonal antibody is inhibited when the antibody to be tested is added.

Furthermore, an antibody which binds to an epitope which is the same as the epitope recognized by the monoclonal antibody which binds to the extracellular region of CD4 of the present invention can be obtained by identifying the epitope of the antibody obtained in the above binding assay, and preparing a partial synthetic peptide, a synthetic peptide mimicking the conformational structure of the epitope or the like, followed by immunization.

(6-b) Kinetic Analysis with Biacore

The kinetics between an antigen and a test substance is measured using Biacore T100 and then the obtained results are analyzed using analysis software accompanied with the apparatus. After anti-IgG mouse antibody is immobilized onto to the a CM 5 sensor chip by an amine coupling method, a test substance such as culture supernatant of a hybridoma, a purified antibody is allowed to flow, bind at an appropriate amount, and further flow an antigen at plural known concentrations, followed by measuring the binding and dissociation. Using the obtained data and the software accompanied with the apparatus, the kinetics analysis is carried out using the 1:1 binding model to obtain necessary parameters. Otherwise, after human CD4 is immobilized onto the sensor chip by an amino coupling method, a purified monoclonal antibody is allowed to flow at plural known concentrations followed by measuring the binding and dissociation. Using the obtained data and the software accompanied with the apparatus, the kinetics analysis is carried out using bivalent analyte model to obtain necessary parameters.

2. Preparation of Recombinant Antibody

As production examples of recombinant antibodies, processes for producing a human chimeric antibody and a humanized antibody are shown below.

(1) Construction of Vector for Expression of Recombinant Antibody

A vector for expression of recombinant antibody is an expression vector for animal cell into which DNAs encoding CH and CL of a human antibody have been inserted, and is constructed by cloning each of DNAs encoding CH and CL of a human antibody into an expression vector for animal cell.

The C region of a human antibody may be CH and CL of any human antibody. Examples include CH belonging to γ1 subclass, CL belonging to κ class, and the like. As the DNAs encoding CH and CL of a human antibody, the cDNA may be generally used and a chromosomal DNA comprising an exon and an intron can be also used. As the expression vector for animal cell, any expression vector can be used, so long as a gene encoding the C region of a human antibody can be inserted thereinto and expressed therein. Examples include pAGE107 [*Cytotechnol.,* 3, 133 (1990)], pAGE103 [*J. Biochem.,* 101, 1307 (1987)], pHSG274 [*Gene,* 27, 223 (1984)], pKCR [*Proc. Natl. Acad. Sci. USA,* 78, 1527 (1981)], pSG1bd2-4 [*Cytotechnol.,* 4, 173 (1990)], pSE1UK1Sed1-3 [*Cytotechnol.,* 13, 79 (1993)] and the like. Examples of a promoter and enhancer used for an expression vector for animal cell include an SV40 early promoter [*J. Biochem.,* 101, 1307 (1987)], a Moloney mouse leukemia virus LTR [*Biochem. Biophys. Res. Commun.,* 149, 960 (1987)], an immunoglobulin H chain promoter [*Cell,* 41, 479 (1985)] and enhancer [*Cell,* 33, 717 (1983)] and the like.

The vector for expression of recombinant antibody may be either of a type in which a gene encoding an antibody H chain and a gene encoding an antibody L chain exist on separate vectors or of a type in which both genes exist on the same vector (tandem type). In respect of easiness of construction of a vector for expression of recombinant antibody, easiness of introduction into animal cells, and balance between the expression amounts of antibody H and L chains in animal cells, a tandem type of the vector for expression of recombinant antibody is more preferred [*J. Immunol. Methods,* 167, 271 (1994)]. Examples of the tandem type of the vector for expression of recombinant antibody include pKANTEX93 (WO 97/10354), pEE18 [*Hybridoma*, 17, 559 (1998)], and the like.

(2) Obtaining of cDNA Encoding V Region of Antibody Derived from Non-Human Animal and Analysis of Amino Acid Sequence Obtaining of cDNAs encoding VH and VL of a non-human animal antibody and analysis of amino acid sequence are carried out as follows.

mRNA is extracted from hybridoma cells producing an antibody derived from a non-human animal to synthesize cDNA. The synthesized cDNA is cloned into a vector such as a phage or a plasmid, to prepare a cDNA library. Each of a recombinant phage or recombinant plasmid containing cDNA encoding VH or VL is isolated from the library using DNA encoding a part of the C region or V region of a mouse antibody as the probe. The full length of the nucleotide sequences of VH and VL of a mouse antibody derived from a non-human animal of interest on the recombinant phage or recombinant plasmid are determined, and the full length of the amino acid sequences of VH and VL are deduced from the nucleotide sequences, respectively.

Examples of the non-human animal for preparing a hybridoma cell which produces a non-human antibody include mouse, rat, hamster, rabbit or the like. Any animals can be used so long as a hybridoma cell can be produced therefrom.

Examples of the method for preparing total RNA from a hybridoma cell include a guanidine thiocyanate-cesium trifluoroacetate method [*Methods in Enzymol.*, 154, 3 (1987)], the use of a kit such as RNA easy kit (manufactured by Qiagen) and the like.

Examples of the method for preparing mRNA from total RNA include an oligo (dT) immobilized cellulose column method [*Molecular Cloning, A Laboratory Manual*, Second Edition, Cold Spring Harbor Laboratory Press (1989)], a method using a kit such as Oligo-dT30 <Super> mRNA Purification Kit (manufactured by Takara Bio) and the like. Also, examples of a kit for preparing mRNA from a hybridoma cell include Fast Track mRNA Isolation Kit (manufactured by Invitrogen), Quick Prep mRNA Purification Kit (manufactured by Pharmacia) and the like.

Examples of the method for synthesizing cDNA and preparing a cDNA library include known methods [*Molecular Cloning, A Laboratory Manual*, Cold Spring Harbor Lab. Press (1989); *Current Protocols in Molecular Biology*, Supplement 1, John Wiley & Sons (1987-1997)]; a method using a kit such as Super Script Plasmid System for cDNA Synthesis and Plasmid Cloning (manufactured by GIBCO BRL), ZAP-cDNA Kit (manufactured by Stratagene), etc.; and the like.

The vector into which the synthesized cDNA using mRNA extracted from a hybridoma cell as the template is inserted for preparing a cDNA library may be any vector, so long as the cDNA can be inserted. Examples include ZAP Express [*Strategies*, 5, 58 (1992)], pBluescript II SK(+) [*Nucleic Acids Research*, 17, 9494 (1989)], λzapII (manufactured by Stratagene), λgt10 and λgt11 [*DNA Cloning: A Practical Approach*, I, 49 (1985)], Lambda BlueMid (manufactured by Clontech), λExCell and pT7T3 18U (manufactured by Pharmacia), pcD2 [*Mol. Cell. Biol.*, 3, 280 (1983)], pUC18 [*Gene*, 33, 103 (1985)], and the like.

Any *Escherichia coli* for introducing the cDNA library constructed by a phage or plasmid vector may be used, so long as the cDNA library can be introduced, expressed and maintained. Examples include XL1-Blue MRF' [*Strategies*, 5, 81 (1992)], C600 [*Genetics*, 39, 440 (1954)], Y1088 and Y1090 [*Science*, 222: 778 (1983)], NM522 [*J. Mol. Biol.*, 166, 1 (1983)], K802 [*J. Mol. Biol.*, 16, 118 (1966)], JM105 [*Gene*, 38, 275 (1985)], and the like.

A colony hybridization or plaque hybridization method using an isotope- or fluorescence-labeled probe may be used for selecting cDNA clones encoding VH and VL of a non-human antibody or the like from the cDNA library [*Molecular Cloning, A Laboratory Manual*, Second Edition, Cold Spring Harbor Laboratory Press (1989)].

Also, the cDNAs encoding VH and VL can be prepared through polymerase chain reaction (hereinafter referred to as "PCR"; *Molecular Cloning, A Laboratory Manual*, Second Edition, Cold Spring Harbor Laboratory Press (1989); *Current Protocols in Molecular Biology*, Supplement 1, John Wiley & Sons (1987-1997)) by preparing primers and using cDNA prepared from mRNA or a cDNA library as the template.

The nucleotide sequence of the cDNA can be determined by digesting the cDNA selected with appropriate restriction enzymes and the like, cloning the fragments into a plasmid such as pBluescript SK(-) (manufactured by Stratagene), carrying out the reaction by a usually used nucleotide analyzing method. For example, a nucleotide analyze is carried out by using an automatic nucleotide sequence analyzer such as ABI PRISM3700 (manufactured by PE Biosystems) and A.L.F. DNA sequencer (manufactured by Pharmacia) after a reaction such as the dideoxy method [*Proc. Natl. Acad. Sci. USA*, 74, 5463 (1977)].

Whether the obtained cDNAs encode the full amino acid sequences of VL and VL of the antibody containing a secretory signal sequence can be confirmed by estimating the full length of the amino acid sequences of VH and VL from the determined nucleotide sequence and comparing them with the full length of the amino acid sequences of VH and VL of known antibodies [*Sequences of Proteins of Immunological Interest*, US Dept. Health and Human Services (1991)]. The length of the secretory signal sequence and N-terminal amino acid sequence can be deduced by comparing the full length of the amino acid sequences of VH and VL of the antibody comprising a secretory signal sequence with full length of the amino acid sequences of VH and VL of known antibodies [*Sequences of Proteins of Immunological Interest*, US Dept. Health and Human Services (1991)], and the subgroup to which they belong can also be known. Furthermore, the amino acid sequence of each of CDRs of VH and VL can be found by comparing the obtained amino acid sequences with amino acid sequences of VH and VL of known antibodies [*Sequences of Proteins of Immunological Interest*, US Dept. Health and Human Services (1991)].

Moreover, the novelty of the full length of the amino acid sequence of VH and VL can be examined by carrying out a homology search with sequences in any database, for example, SWISS-PROT, PIR-Protein or the like using the obtained full length of the amino acid sequences of VH and VL, for example, according to the BLAST method [*J. Mol. Biol.*, 215, 403 (1990)] or the like.

(3) Construction of Vector for Expression of Human Chimeric Antibody cDNA encoding each of VH and VL of antibody of non-human animal is cloned in the upstream of genes encoding CH or CL of human antibody of vector for expression of recombinant antibody mentioned in the above (1) to thereby construct a vector for expression of human chimeric antibody.

For example, in order to ligate cDNA comprising a nucleotide sequence of 3'-terminal of VH or VL of antibody of non-human animal and a nucleotide sequence of 5'-terminal of CH or CL of human antibody, each cDNA encoding VH and VL of antibody of non-human animal is prepared so as to encodes appropriate amino acids encoded by a nucleotide sequence of a linkage portion and designed to have an appropriate recognition sequence of a restriction enzyme. The obtained cDNAs encoding VH and VL of antibody are respectively cloned so that each of them is expressed in an appropriate form in the upstream of gene encoding CH or CL of human antibody of the vector for expression of humanized antibody mentioned in the above (1) to construct a vector for expression of human chimeric antibody.

In addition, cDNA encoding VH or VL of a non-human animal antibody is amplified by PCR using a synthetic DNA having a recognition sequence of an appropriate restriction enzyme at both ends and each of them is cloned to the vector for expression of recombinant antibody obtained in the above (1).

(4) Construction of cDNA Encoding V Region of Humanized Antibody cDNAs encoding VH or VL of a humanized antibody can be obtained as follows.

Amino acid sequences of framework region (hereinafter referred to as "FR") in VH or VL of a human antibody to which amino acid sequences of CDRs in VH or VL of an antibody derived from a non-human animal antibody are transplanted are respectively selected. Any amino acid sequences of FR of a human antibody can be used, so long as they are derived from human. Examples include amino acid sequences of FRs of human antibodies registered in database such as Protein Data Bank or the like, and amino acid sequences common to subgroups of FRs of human antibodies [*Sequences of Proteins of Immunological Interest*, US Dept. Health and Human Services (1991)], and the like. In order to inhibit the decrease in the binding activity of the antibody, amino acid sequences having high homology (at least 60% or more) with the amino acid sequence of FR in VH or VL of the original antibody is selected.

Then, amino acid sequences of CDRs of the original antibody are grafted to the selected amino acid sequence of FR in VH or VL of the human antibody, respectively, to design each amino acid sequence of VH or VL of a humanized antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed.

Based on the designed nucleotide sequences, several synthetic DNAs having a length of about 100 nucleotides are synthesized, and PCR is carried out using them. In this case, it is preferred that 6 synthetic DNAs per each of the H chain and the L chain are designed in view of the reaction efficiency of PCR and the lengths of DNAs which can be synthesized.

Furthermore, the cDNA encoding VH or VL of a humanized antibody can be easily cloned into the vector for expression of humanized antibody constructed in (1) by introducing the recognition sequence of an appropriate restriction enzyme to the 5' terminal of the synthetic DNAs existing on the both ends.

Otherwise, it can be carried out using a synthetic DNA as one DNA encoding each of the full-length H chain and the full-length L chain based on the designed DNA sequence.

After the PCR, an amplified product is cloned into a plasmid such as pBluescript SK(−) (manufactured by Stratagene) or the like, and the nucleotide sequence is determined according to a method similar to the method described in (2) to obtain a plasmid having a DNA sequence encoding the amino acid sequence of VH or VL of a desired humanized antibody.

(5) Modification of Amino Acid Sequence of V Region of Humanized Antibody

It is known that when a humanized antibody is produced by simply grafting only CDRs in VH and VL of an antibody derived from a non-human animal into FRs of VH and VL of a human antibody, its antigen binding activity is lower than that of the original antibody derived from a non-human animal [*BIO/TECHNOLOGY*, 9, 266 (1991)]. In humanized antibodies, among the amino acid sequences of FRs in VH and VL of a human antibody, an amino acid residue which directly relates to binding to an antigen, an amino acid residue which interacts with an amino acid residue in CDR, and an amino acid residue which maintains the three-dimensional structure of an antibody and indirectly relates to binding to an antigen are identified and modified to an amino acid residue which is found in the original non-humanized antibody to thereby increase the antigen binding activity which has been decreased.

In order to identify the amino acid residues relating to the antigen binding activity in FR, the three-dimensional structure of an antibody is constructed and analyzed by X-ray crystallography [*J. Mol. Biol.*, 112, 535 (1977)], computer-modeling [*Protein Engineering*, 7, 1501 (1994)] or the like. In addition, various attempts must be currently be necessary, for example, several modified antibodies of each antibody are produced and the correlation between each of the modified antibodies and its antibody binding activity is examined.

The modification of the amino acid sequence of FR in VH and VL of a human antibody can be accomplished using various synthetic DNA for modification according to PCR as described in (4). With regard to the amplified product obtained by the PCR, the nucleotide sequence is determined according to the method as described in (2) so that whether the objective modification has been carried out is confirmed.

(6) Construction of Vector for Expression of Humanized Antibody

A vector for expression of humanized antibody can be constructed by cloning each cDNA encoding VH or VL of a constructed recombinant antibody into upstream of each gene encoding CH or CL of the human antibody in the vector for expression of recombinant antibody as described in (1).

For example, when recognizing sequences of an appropriate restriction enzymes are introduced to the 5'-terminal of synthetic DNAs positioned at both ends among synthetic DNAs used in the construction of VH or VL of the humanized antibody in (4) and (5), cloning can be carried out so that they are expressed in an appropriate form in the upstream of each gene encoding CH or CL of the human antibody in the vector for expression of a humanized antibody as described in (1).

(7) Transient Expression of Recombinant Antibody

In order to efficiently evaluate the antigen binding activity of various humanized antibodies produced, the recombinant antibodies can be expressed transiently using the vector for expression of humanized antibody as described in (3) and (6) or the modified expression vector thereof.

Any cell can be used as a host cell, so long as the host cell can express a recombinant antibody. Generally, COS-7 cell (ATCC CRL1651) is used in view of its high expression amount [*Methods in Nucleic Acids Res.*, CRC Press, 283 (1991)].

Examples of the method for introducing the expression vector into COS-7 cell include a DEAE-dextran method [*Methods in Nucleic Acids Res.*, CRC Press, 283 (1991)], a lipofection method [*Proc. Natl. Acad. Sci. USA*, 84, 7413 (1987)], and the like.

After introduction of the expression vector, the expression amount and antigen binding activity of the recombinant antibody in the culture supernatant can be determined by the enzyme immunoassay [*Monoclonal Antibodies—Principles and practice*, Third edition, Academic Press (1996), *Antibodies—A Laboratory Manual*, Cold Spring Harbor Laboratory (1988), *Monoclonal Antibody Experiment Manual*, Kodansha Scientific (1987)] and the like.

(8) Obtaining Transformant Which Stably Expresses Recombinant Antibody and Preparation of Recombinant Antibody A transformant which stably expresses a recombinant antibody can be obtained by introducing the vector for expression of recombinant antibody described in (3) and (6) into an appropriate host cell.

Examples of the method for introducing the expression vector into a host cell include electroporation [Japanese Published Unexamined Patent Application No. 257891/90, *Cytotechnology*, 3, 133 (1990)] and the like.

As the host cell into which a vector for expression of a recombinant antibody is introduced, any cell can be used, so long as it is a host cell which can produce the recombinant antibody. Examples include CHO-K1 (ATCC CCL-61), DUkXB11 (ATCC CCL-9096), Pro-5 (ATCC CCL-1781), CHO-S (Life Technologies, Cat #11619), rat myeloma cell YB2/3HL.P2.G11.16Ag.20 (also referred to as YB2/0), mouse myeloma cell NS0, mouse myeloma cell SP2/0-Ag14 (ATCC No. CRL1581), mouse P3X63-Ag8.653 cell (ATCC No. CRL1580), CHO cell in which a dihydrofolate reductase gene (hereinafter referred to as "dhfr") is defective [*Proc. Natl. Acad. Sci. U.S.A.*, 77, 4216 (1980)], lection resistance-acquired Lec13 [*Somatic Cell and Molecular genetics*, 12, 55 (1986)], CHO cell in which α1,6-fucosyltransferase gene is defected (WO 2005/35586, WO 02/31140), rat YB2/3HL.P2.G11.16Ag.20 cell (ATCC No. CRL1662), and the like.

In addition, host cells in which activity of a protein such as an enzyme relating to synthesis of an intracellular sugar nucleotide, GDP-fucose, a protein such as an enzyme relating to the modification of a sugar chain in which 1-position of fucose is bound to 6-position of N-acetylglucosamine in the reducing end through α-bond in a complex type N-glycoside-linked sugar chain, or a protein relating to transport of an intracellular sugar nucleotide, GDP-fucose, to the Golgi body are introduced is decreased or deleted, preferably CHO cell in which α1,6-fucosyltransferase gene is defected as described in WO05/35586, WO02/31140 or the like, can also be used.

After introduction of the expression vector, transformants which express a recombinant antibody stably are selected by culturing in a medium for animal cell culture containing an agent such as G418 sulfate (hereinafter referred to as "G418") or the like (Japanese Published Unexamined Patent Application No. 257891/90).

Examples of the medium for animal cell culture include RPMI1640 medium (manufactured by Invitrogen), GIT medium (manufactured by Nihon Pharmaceutical), EX-CELL301 medium (manufactured by JRH), IMDM medium (manufactured by Invitrogen), Hybridoma-SFM medium (manufactured by Invitrogen), media obtained by adding various additives such as fetal calf serum (hereinafter referred to as "FCS") to these media, and the like. The recombinant antibody can be produced and accumulated in a culture supernatant by culturing the selected transformants in a medium. The expression amount and antigen binding activity of the recombinant antibody in the culture supernatant can be measured by ELISA or the like. Also, in the transformant, the expression amount of the recombinant antibody can be increased by using DHFR amplification system or the like according to the method disclosed in Japanese Published Unexamined Patent Application No. 257891/90.

The recombinant antibody can be purified from the culture supernatant of the transformant by using a protein A column [*Monoclonal Antibodies—Principles and practice*, Third edition, Academic Press (1996), *Antibodies—A Laboratory Manual*, Cold Spring Harbor Laboratory (1988)]. For example, the recombinant antibody can be purified by a combination of gel filtration, ion-exchange chromatography, ultrafiltration and the like.

The molecular weight of the H chain or the L chain of the purified recombinant antibody or the antibody molecule as a whole is determined by polyacrylamide gel electrophoresis (hereinafter referred to as "SDS-PAGE") [*Nature*, 227, 680 (1970)], Western blotting [*Monoclonal Antibodies—Principles and practice*, Third edition, Academic Press (1996), *Antibodies—A Laboratory Manual*, Cold Spring Harbor Laboratory (1988)], and the like.

3. Activity Evaluation of the Monoclonal Antibody or Antibody Fragment

The activity of the purified monoclonal antibody or antibody fragment of the present invention can be evaluated in the following manner.

The binding activity to CD4-expressing cell is evaluated by the binding assay described in the above 1-(6-a) and a surface plasmon resonance method using such as the Biacore system described in the above (6-b). Furthermore, it can be measured by fluorescent antibody technique [*Cancer Immunol. Immunother.*, 36, 373 (1993)], a surface plasmon resonance method using such as BIAcore system or the like. Furthermore, it can be measured by fluorescent antibody technique [*Cancer Immunol. Immunother.*, 36, 373 (1993)].

In addition, CDC activity or ADCC activity against an antigen positive cell line is evaluated by a known method [*Cancer Immunol. Immunother.*, 36, 373 (1993)].

4. Method of Controlling Effector Activity of Antibody

As a method for controlling an effector activity of the anti-CD4 monoclonal antibody of the present invention, a method for controlling an amount of fucose (hereinafter, referred to also as "core fucose") which is bound in α-1,6 linkage to N-acetylglucosamine (GlcNAc) present in a reducing end of a complex type N-linked sugar chain which is bound to asparagine (Asn) at position 297 of an Fc region of an antibody (WO2005/035586, WO2002/31140, and WO00/61739), a method for controlling an effector activity of a monoclonal antibody by modifying amino acid group(s) of an Fc region of the antibody, and the like are known. The effector activity of the anti-CD4 monoclonal antibody of the present invention can be controlled by using any of the methods.

The "effector activity" means an antibody-dependent activity which is induced via an Fc region of an antibody. As the effector activity, an antibody-dependent cellular cytotoxicity (ADCC activity), a complement-dependent cytotoxicity (CDC activity), an antibody-dependent phagocytosis (ADP activity) by phagocytic cells such as macrophages or dendritic cells, and the like are known.

By controlling a content of core fucose of a complex type N-linked sugar chain of Fc of an antibody, an effector activity of the antibody can be increased or decreased. According to a method for lowering a content of fucose which is bound to a complex type N-linked sugar chain bound to Fc of the antibody, an antibody to which fucose is not bound can be obtained by the expression of an antibody using a CHO cell which is deficient in a gene encoding α1,6-fucosyltransferase. The antibody to which fucose is not bound has a high ADCC activity. On the other hand, according to a method for increasing a content of fucose which is bound to a complex type N-linked sugar chain bound to Fc of an antibody, an antibody to which fucose is bound can be obtained by the expression of an antibody using a host cell into which a gene encoding α1,6-fucosyltransferase is introduced. The antibody to which fucose is bound has a lower ADCC activity than the antibody to which fucose is not bound.

Further, by modifying amino acid residue(s) in an Fc region of an antibody, the ADCC activity or CDC activity can be increased or decreased. The ADCC activity can be controlled by increasing or decreasing the binding activity to FcγR due to the modification(s) of amino acid residue(s) in an Fc region. In addition, the CDC activity can be controlled by increasing or decreasing the binding activity of complement due to the modification(s) of amino acid residue(s) in an Fc region. For example, the binding activity to an antibody can be increased by using the amino acid sequence of the Fc region described in US2007/0148165. Further, the ADCC activity or CDC activity can be increased or decreased by modifying the amino acid as described in U.S. Pat. Nos. 6,737,056, or 7,297,775 or WO2005/070963.

Furthermore, an antibody in which the effector activity is controlled can be obtained by combining the above method for controlling a sugar chain and the method for modifying amino acid(s) in an Fc region.

5. Method for Treating Disease Using the Anti-CD4 Monoclonal Antibody or Antibody Fragment of the Present Invention A monoclonal antibody which specifically recognizes a native three-dimensional structure of CD4 and binds to the extracellular region, or an antibody fragment thereof of the present invention can be used for treating a disease relating to CD4.

Examples of a route of administration include oral administration and parenteral administration, such as buccal, tracheal, rectal, subcutaneous, intramuscular or intravenous administration. In the case of an antibody or peptide formulation, intravenous administration is preferred. Examples of the dosage form includes sprays, capsules, tablets, powder, granules, syrups, emulsions, suppositories, injections, ointments, tapes and the like.

The pharmaceutical preparation suitable for oral administration includes emulsions, syrups, capsules, tablets, powders, granules and the like.

Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like.

Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like.

Injections can be prepared using a carrier such as a salt solution, a glucose solution or a mixture of both thereof.

Suppositories can be prepared using a carrier such as cacao butter, hydrogenated fat or carboxylic acid.

Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. It is possible to produce pharmaceutical preparations such as aerosols and dry powders.

In addition, the components exemplified as additives for oral preparations can also be added to the parenteral preparations.

5. Method for Diagnosing Disease Using the Anti-CD4 Monoclonal Antibody or Antibody Fragment of the Present Invention A disease relating to CD4 can be diagnosed by detecting or determining CD4 or a cell expressing CD4 using the monoclonal antibody or antibody fragment of the present invention.

A diagnosis of cancer, one of the diseases relating to CD4, can be carried out by, for example, the detection or measurement of CD4 as follows.

The diagnosis of cancer can be carried out by detecting CD4 expressing on the cell in a patient's body by an immunological method such as a flow cytometer.

An immunological method is a method in which an antibody amount or an antigen amount is detected or determined using a labeled antigen or antibody. Examples of the immunological method include radioactive substance-labeled immunoantibody method, enzyme immunoassay, fluorescent immunoassay, luminescent immunoassay, Western blotting method, physico-chemical means and the like.

Examples of the radioactive substance-labeled immunoantibody method include a method, in which the antibody or antibody fragment of the present invention is allowed to react with an antigen, a cell expressing an antigen or the like, then anti-immunoglobulin antibody subjected to a radioactive labeling or a binding fragment thereof is allowed to react therewith, followed by determination using a scintillation counter or the like.

Examples of the enzyme immunoassay include a method, in which the antibody or antibody fragment of the present invention is allowed to react with an antigen, a cell expressing an antigen or the like, then an anti-immunoglobulin antibody or an binding fragment thereof subjected to antibody labeling is allowed to react therewith and the colored pigment is measured by a spectrophotometer, and, for example, sandwich ELISA may be used. As a label used in the enzyme immunoassay, any known enzyme label (*Enzyme Immunoassay*, published by Igaku Shoin, 1987) can be used as described already. Examples include alkaline phosphatase labeling, peroxidase labeling, luciferase labeling, biotin labeling and the like.

Sandwich ELISA is a method in which an antibody is bound to a solid phase, antigen to be detected or measured is trapped and another antibody is allowed to react with the trapped antigen. In the ELISA, two kinds of antibody which recognizes the antigen to be detected or measured or the antibody fragment thereof in which antigen recognizing site is different are prepared and the first antibody or antibody fragments is previously adsorbed on a plate (such as a 96-well plate) and the second antibody or antibody fragment is labeled with a fluorescent substance such as FITC, an enzyme such as peroxidase, or biotin. The plate to which the above antibody is adsorbed is allowed to react with the cell separated from living body or disrupted cell suspension thereof, tissue or disintegrated solution thereof, cultured cells, serum, pleural effusion, ascites, eye solution or the like, then allowed to react with a labeled monoclonal antibody or an antibody fragment and a detection reaction corresponding to the labeled substance is carried out. The antigen concentration in the sample to be tested can be calculated from a calibration curve prepared by a stepwise dilution of antigen of known concentration. As antibody used for sandwich ELISA, any of polyclonal antibody and monoclonal antibody may be used or antibody fragments such as Fab, Fab' and F(ab)$_2$ may be used. As a combination of 2 kinds of antibodies used in sandwich ELISA, a combination of monoclonal antibodies or antibody fragments recognizing different epitopes may be used or a combination of polyclonal antibody with monoclonal antibody or antibody fragments may be used.

A fluorescent immunoassay includes a method described in the literatures [*Monoclonal Antibodies—Principles and practice,* Third Edition, Academic Press (1996); *Manual for Monoclonal Antibody Experiments,* Kodansha Scientific (1987)] and the like. As a label for the fluorescent immunoassay, any of known fluorescent labels [*Fluorescent Immunoassay,* by Akira Kawao, Soft Science, (1983)] may be used as described already. Examples of the label include FITC, RITC and the like.

The luminescent immunoassay can be carried out using the methods described in the literature [*Bioluminescence and Chemical Luminescence, Rinsho Kensa,* 42, Hirokawa Shoten (1998)] and the like. As a label used for luminescent immunoassay, any of known luminescent labels can be included. Examples include acridinium ester, lophine or the like may be used.

Western blotting is a method in which an antigen or a cell expressing an antigen is fractionated by SDS-polyacrylamide gel electrophoresis [*Antibodies—A Laboratory Manual* (Cold Spring Harbor Laboratory, 1988)], the gel is blotted onto PVDF membrane or nitrocellulose membrane, the membrane is allowed to react with antigen-recognizing antibody or antibody fragment, further allowed to react with an anti-mouse IgG antibody or antibody fragment which is labeled with a fluorescent substance such as FITC, an enzyme label such as peroxidase, a biotin labeling, or the like, and the label is visualized to confirm the reaction. An example thereof is described below. Cells or tissues in which a polypeptide having the amino acid sequence represented by SEQ ID NO:2 is expressed are dissolved in a solution and, under reducing conditions, 0.1 to 30 μg as a protein amount per lane is electrophoresed by an SDS-PAGE method. The electrophoresed protein is transferred to a PVDF membrane and allowed to react with PBS containing 1 to 10% of BSA (hereinafter referred to as "BSA-PBS") at room temperature for 30 minutes for blocking. Here, the monoclonal antibody of the present invention is allowed to react therewith, washed with PBS containing 0.05 to 0.1% Tween 20 (hereinafter referred to as "Tween-PBS") and allowed to react with goat anti-mouse IgG labeled with peroxidase at room temperature for 2 hours. It is washed with Tween-PBS and a band to which the monoclonal antibody is bound is detected using ECL Western Blotting Detection Reagents (manufactured by Amersham) or the like to thereby detect a polypeptide having the amino acid sequence represented by SEQ ID NO:2. As an antibody used for the detection in Western blotting, an antibody which can be bound to a polypeptide having no three-dimensional structure of a natural type is used.

The physicochemical method is specifically carried out by reacting CD4 as the antigen with the antibody or antibody fragment of the present invention to form an aggregate, and detecting this aggregate. Other examples of the physicochemical methods include a capillary method, a one-dimensional immunodiffusion method, an immunoturbidimetry, a latex immunoturbidimetry [*Handbook of Clinical Test Methods,* Kanehara Shuppan, (1988)] and the like. For example, in a latex immunodiffusion method, a carrier such as polystyrene latex having a particle size of about of 0.1 to 1 μm sensitized with antibody or antigen may be used and when an antigen-antibody reaction is carried out using the corresponding antigen or antibody, scattered light in the reaction solution increases while transmitted light decreases. When such a change is detected as absorbance or integral sphere turbidity, it is now possible to measure antigen concentration, etc. in the sample to be tested.

For the detection of the cell expressing CD4, known immunological detection methods can be used, and an immunoprecipitation method, a immuno cell staining method, an immune tissue staining method, a fluorescent antibody staining method and the like are preferably used.

An immunoprecipitation method is a method in which a cell expressing CD4 is allowed to react with the monoclonal antibody or antibody fragment of the present invention and then a carrier having specific binding ability to immunoglobulin such as protein G-Sepharose is added so that an antigen-antibody complex is precipitated. Also, the following method can be carried out.

The above-described antibody or antibody fragment of the present invention is solid-phased on a 96-well plate for ELISA and then blocked with BSA-PBS. When the antibody is in a non-purified state such as a culture supernatant of hybridoma cell, anti-mouse immunoglobulin or rat immunoglobulin or protein A or Protein G or the like is previously adsorbed on a 96-well plate for ELISA and blocked with BSA-PBS and a culture supernatant of hybridoma cell is dispensed thereto for binding. After BSA-PBS is discarded and the residue is sufficiently washed with PBS, reaction is carried out with a dissolved solution of cells or tissues expressing CD4. An immune precipitate is extracted from the well-washed plate with a sample buffer for SDS-PAGE and detected by the above-described Western blotting.

An immune cell staining method or an immune tissue staining method are a method where cells or tissues in which antigen is expressed are treated, if necessary, with a surfactant, methanol or the like to make an antibody easily permeate to the cells or tissues, then the monoclonal antibody of the present invention is allowed to react therewith, then further allowed to react with an anti-immunoglobulin antibody or binding fragment thereof subjected to fluorescent labeling such as FITC, enzyme label such as peroxidase or biotin labeling and the label is visualized and observed under a microscope. In addition, cells of tissues can be detected by an immunofluorescent staining method where cells are allowed to react with a fluorescence-labeled antibody and analyzed by a flow cytometer [*Monoclonal Antibodies—Principles and practice,* Third Edition, Academic Press (1996), *Manual for Experiments of Monoclonal Antibodies,* Kodansha Scientific (1987)] in which cells are allowed to react with a fluorescence-labeled antibody and analyzed by a flow cytometer. Particularly, the monoclonal antibody or antibody fragment of the present invention which binds to an extracellular region of the CD4 can detect a cell expressing the polypeptide maintaining a natural type three-dimensional structure.

In addition, in the case of using FMAT8100HTS system (manufactured by Applied Biosystems) and the like among fluorescent antibody staining methods, the antigen quantity or antibody quantity can be measured without separating the formed antibody-antigen complex and the free antibody or antigen which is not concerned in the formation of the antibody-antigen complex.

The present invention is described below by Examples; however, the present invention is not limited to the following Examples.

EXAMPLE 1

Construction of CD4 Transfectant (1) Construction of CD4 Expression Vector

A vector into which a human CD4 nucleotide sequence was inserted was constructed as follows, from a vector (Clone No. 5226427, hereinafter referred to as "pCMV-CD4", manufactured by Open Biosystems) where a human CD4 gene was inserted into a vector pCMV-SPORT6.

The CD4 gene fragment was amplified using pCMV-CD4 as a template and primers comprising the nucleotide sequences represented by SEQ ID NOs:79 and 80, in accordance with a conventional PCR method. The PCR product was purified by a PCR Purification Kit (manufactured by Qiagen), and then treated with restriction enzymes EcoRI and SpeI. Similarly, a vector pBluescript II sk(−) (manufactured by Stratagene) (hereinafter, referred to as "pBS") was treated with restriction enzymes EcoRI and SpeI. The resulting two fragments were ligated using a Ligation high (manufactured by Toyobo) in accordance with the instructions attached thereto. An *Escherichia coli* DH5α strain (manufactured by Toyobo) was transformed with the obtained recombinant plasmid DNA solution. A plasmid DNA was prepared from the clone of the transformant and was confirmed by treatment with restriction enzymes, and a plasmid pBS/CD4 into which a CD4 gene was inserted was obtained. The resulting pBS/CD4 into which a CD4 gene was inserted, and an expression vector pKANTEX93 (WO97/10354) for an animal cell were treated with restriction enzymes EcoRI and SpeI. The reaction liquid was fractionated by agarose gel electrophoresis, thereby recovering an EcoRI-SpeI fragment of CD4 and an EcoRI-SpeI fragment of pKANTEX93, respectively. These two fragments were ligated using a Ligation high (manufactured by Toyobo) in accordance with the instructions attached thereto. An *Escherichia coli* DH5α strain (manufactured by Toyobo) was transformed with the resulting recombinant plasmid DNA solution. A plasmid DNA was prepared from the clone of the transformant and was confirmed by the treatment with restriction enzymes, and a plasmid pKANTEX/CD4 into which a CD4 gene was inserted was obtained. The plasmid obtained was allowed to react using a BigDye Terminator Cycle Sequencing FS Ready Reaction Kit (manufactured by PE Biosystems) in accordance with the instructions attached thereto, and then its nucleotide sequence was analyzed by a sequencer of the same company, ABI PRISM3700. As a result, a vector pKANTEX/CD4 into which a cDNA encoding human CD4 was cloned was obtained. FIG. 1 illustrates a schematic diagram for the construction of the vector.

(2) Construction of CD4-Expressing CHO/DG44 Cell

In accordance with electroporation [Cytotechnology, 3, 133 (1990)], the CD4 expression vector pKANTEX/CD4 constructed in Section (1) into a CHO/DG44 cell [*Somatic Cell and Molecular Genetics*, 12, 555 (1986)] was introduced in the following manner. The cells used herein are those subcultured in a medium where 1×HT supplement (manufactured by Invitrogen) was added to IMDM (manufactured by Invitrogen) supplemented with 10% fetal bovine serum (manufactured by Life Technologies) and gentamicin (50 μg/mL, manufactured by Nacalai Tesque) (hereinafter, referred to as "A3 medium"). CHO/DG44 cells were suspended in a buffer containing potassium chloride (137 nmol/L), sodium chloride (2.7 nmol/L), disodium hydrogen phosphate (8.1 mmol/L), sodium dihydrogen phosphate (1.5 nmol/L) and magnesium chloride (4 mmol/L) (hereinafter, referred to as "K-PBS") to give a cell concentration of $8 \times 10^6$ cells/mL, and the resulting cell suspension (200 μL, $1.6 \times 10^6$ cells in terms of cell count) was mixed with the expression plasmid pKANTEX/CD4 (8 μg). The mixture was transferred into a cuvette (interelectrode distance: 2 mm), followed by gene transfer using a GenePulser II (manufactured by Bio-Rad) at a pulse voltage of 0.35 kV and an electric capacity of 250 μF. After the cuvette was allowed to stand on ice, the cell suspension in the cuvette was suspended in a cell culture vessel containing A3 medium and cultured in a 5% $CO_2$ incubator at 37° C. Thereafter, the cells were cultured in a medium containing G418 (manufactured by Invitrogen, 0.5 mg/mL), and then a transformed cell line resistant to G418 was obtained. In addition, a clone showing a high expression level of CD4 was selected by adding methotrexate to the medium and increasing the concentration in a stepwise manner. In this manner, a CD4-expressing CHO cell line (hereinafter, referred to as "CHO/CD4 cell" or "CD4 transfectant") was obtained.

EXAMPLE 2

Construction of CD4-Fc (1) Construction of CD4-Fc Expression Vector

Figure 2:
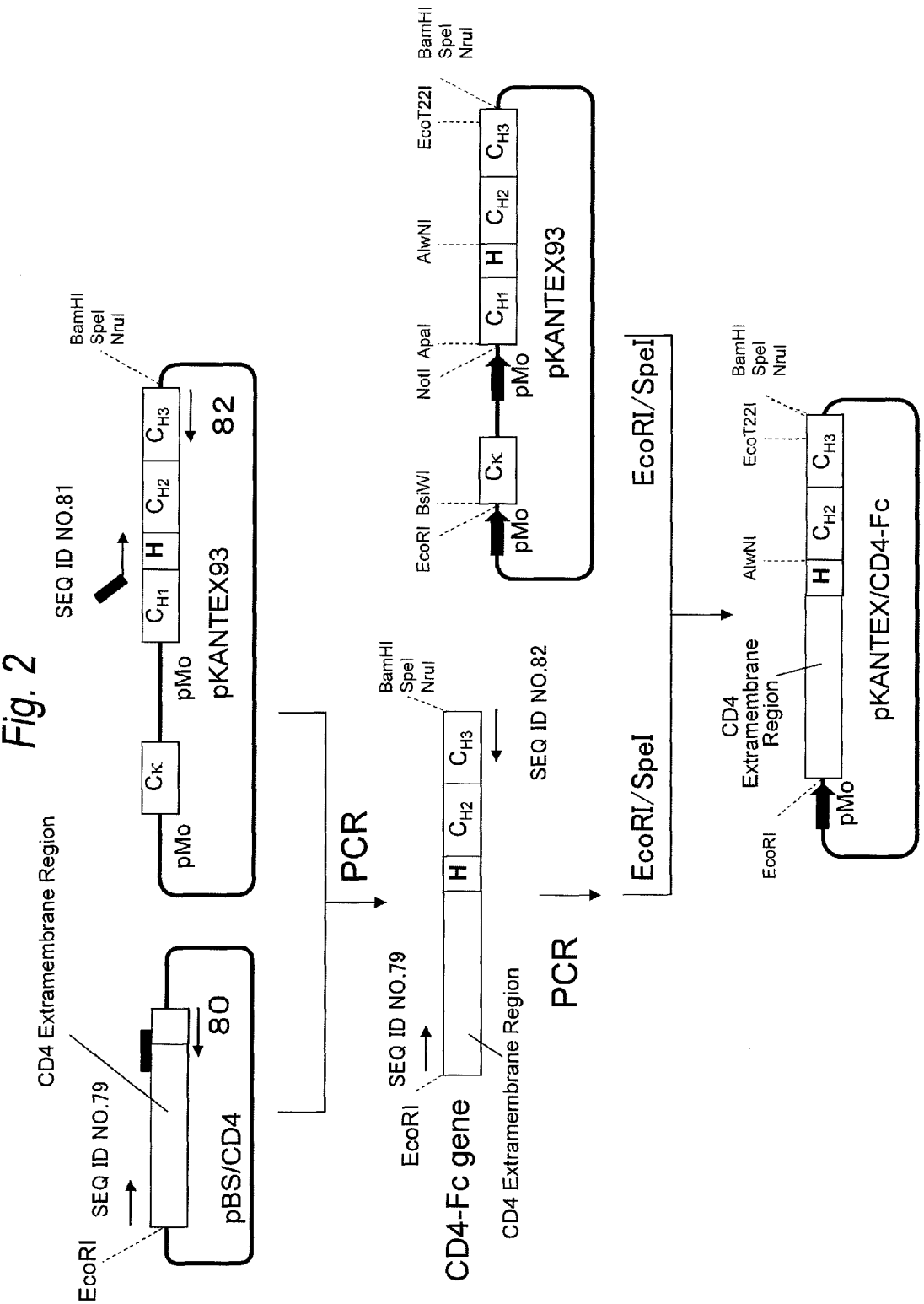
FIG. 2 shows a construction process of a CD4-Fc expression vector.

The vector pBS/CD4 constructed in Example 1(1), into which a human CD4 gene was inserted, and a vector pKANTEX93 were mixed for use as a template. PCR was carried out using the mixture as a template, and four synthetic oligo nucleotides represented by SEQ ID NOs:79, 80, 81, and 82 as primers. According to this reaction, a nucleotide sequence in which a gene encoding an extracellular region of a CD4 protein was ligated with a gene of the Fc region was synthesized (hereinafter, referred to as "CD4-Fc gene"). The resulting PCR product was fractionated by agarose gel electrophoresis, and a desired CD4-Fc gene (about 2 kbp) was cleaved and purified. PCR was carried out again using the purified product as a template, and two primers represented by SEQ ID NOs:79 and 82, so that the CD4-Fc gene was amplified. The resulting PCR product was fractionated by agarose gel electrophoresis, and a desired gene CD4-Fc (about 2 kbp) was cleaved and treated with restriction enzymes EcoRI and SpeI, thereby obtaining an EcoRI-SpeI fragment of the CD4-Fc gene. Similarly, the vector pKANTEX93 was treated with restriction enzymes EcoRI and SpeI. The resulting two fragments were ligated using a Ligation High (manufactured by Toyobo). An *Escherichia coli* DH5α strain (manufactured by Toyobo) was transformed with the obtained recombinant plasmid DNA solution. A plasmid DNA was prepared from the clone of the transformant and was confirmed by treatment with restriction enzymes, and a plasmid pKANTEX/CD4-Fc into which the CD4-Fc gene was inserted was obtained. The plasmid obtained was reacted using a BigDye Terminator Cycle Sequencing FS Ready Reaction Kit (manufactured by PE Biosystems) in accordance with the instructions attached thereto, and then the nucleotide sequence was analyzed by a sequencer of the same company, ABI PRISM3700. As a result, a vector pKANTEX/CD4-Fc into which a cDNA encoding CD4-Fc was cloned was obtained. FIG. 2 illustrates a schematic diagram for the construction of the vector.

(2) Expression of CD4-Fc

Using the pKANTEX/CD4-Fc constructed in Section (1), a CHO cell expressing CD4-Fc (hereinafter, referred to as "CHO/CD4-Fc") was obtained by a conventional method [Antibody Engineering, A Practical Guide, W.H. Freeman and Company (1992)].

(3) Purification of Soluble CD4-Fc

After culturing the CHO/CD4-Fc constructed in Section (2) under the same culture conditions as in Example 1(2), the cell suspension was recovered and centrifuged at 3000 rpm and 4° C. for 20 minutes to recover the culture supernatant, and then the culture supernatant was filtration-sterilized using a 0.22-μm pore size Millex GV filter (manufactured by Millipore). The CD4-Fc protein was purified from the resulting culture supernatant, using a Protein A High-capacity resin (manufactured by Millipore) column in accordance with the instructions attached thereto.

EXAMPLE 3

Preparation of Anti-CD4 Monoclonal Antibody
(1) Preparation of Immunogen
In order to obtain an anti-CD4 monoclonal antibody, a lyophilized product of recombinant human CD4 (catalogue number: 514-CD/CF, manufactured by R&D Systems) dissolved in a Dulbecco's phosphate buffer (phosphate buffered saline: PBS), or a human CD4-Fc fusion protein (hereinafter, referred to as "CD4-Fc") prepared in Example 2(3) was used as an immunogen.

(2) Immunization of Animal and Preparation of Antibody-Producing Cell
Into SD rats (manufactured by Japan SLC) was administered 20 μg of the recombinant human CD4 or the CD4-Fc prepared in Example 2(3), together with 2 mg of an aluminum hydroxide adjuvant (*Antibodies—A Laboratory Manual*, Cold Spring Harbor Laboratory, p 99, 1988) and $1 \times 10^9$ cells of a pertussis vaccine (manufactured by Chiba Serum Institute). Two weeks after the administration, 20 μg of the CD4 and 2 mg of an aluminum hydroxide adjuvant alone were administered to the rats once a week, four times in total. Blood was partially collected from the fundus oculi vein of the rats, and the serum antibody titer was confirmed by CD4 binding ELISA. The spleen was extracted from a rat which showed a sufficient antibody titer three days after the final immunization. The spleen was minced into small pieces in Minimum Essential Medium (MEM, manufactured by Nissui Pharmaceutical Co., Ltd.), ground and centrifuged (1200 rpm, 5 minutes). Tris-ammonium chloride buffer (pH 7.6) was added to treat the resulting precipitation fraction for 1 minute at 37° C., whereby red blood cells were removed. The resulting precipitation fraction (cell fraction) was washed three times with MEM, and used in the cell fusion.

(3) CD4 Binding ELISA
For the assay a 96-well ELISA plate (manufactured by Greiner) was used. For this purpose, 2 μg/mL of the recombinant human CD4 prepared in Example 1(1) was dispensed at a concentration of 50 μL/well to the plate, and allowed to stand at 4° C. overnight for adsorption. After the plate was washed with PBS, 100 μL/well of 1% bovine serum albumin (BSA)-PBS (hereinafter, referred to as "BSA-PBS") was added to the plate, and the plate was then allowed to stand at room temperature for 1 hour such that the remaining active groups were blocked. Then, BSA-PBS was discarded, and 50 μL/well of an appropriate dilution of the immunized rat serum as a primary antibody was dispensed to the plate, and the plate was then allowed to stand for 2 hours. The plate was washed with 0.05% polyoxyethylene (20) sorbitan monolaurate [(the equivalent of ICI trade name Tween 20, manufactured by Wako Pure Chemical)]/PBS (hereinafter referred to as "Tween-PBS"), and 50 μL/well of a peroxidase-labeled goat anti-rat IgG (H+L chain) antibody (manufactured by Zymed) as a secondary antibody was added to the plate, and the plate was then allowed to stand at room temperature for 1 hour. The plate was washed with Tween-PBS, and color-developed by adding 50 μL/well of a 2,2-azinobis(3-ethylbenzothiazole-6-sulfonic acid)ammonium (ABTS) substrate solution [1 mmoL/L ABTS, 0.1 moL/L citrate buffer (pH 4.2), 0.1% $H_2O_2$]. The reaction was stopped by adding 50 μL/well of a 5% sodium lauryl sulfate (SDS) solution, and an absorbance (OD415 nm) was then measured using a plate reader Emax (Molecular Devices).

(4) Preparation of Mouse Myeloma Cell
The 8-azaguanine-resistant mouse myeloma cell line P3X63Ag8U.1 (P3-U1, purchased from ATCC) was cultured in RPMI 1640 medium (manufactured by Invitrogen) supplemented with 10% of fetal bovine serum to ensure the cell count of $2 \times 10^7$ or more necessary for cell fusion, and was provided as parent cells in the cell fusion.

(5) Measurement of Culture Supernatant by FMAT Method
The CD4 transfectants prepared in Example 1 or CHO/DG44 cells as a negative control were seeded onto a 96-well FMAT plate (manufactured by Applied Biosystems) at a cell density of $1 \times 10^4$ cells/50 μL/well, followed by overnight culture in a 5% CO2 incubator at 37° C. To the plate, 10 μL/well of the culture supernatant of the hybridoma was added and then 50 μL/well of an ALEXA 647-labeled goat anti-rat IgG (H+L) antibody (manufactured by Invitrogen) diluted with BSA-PBS was immediately added thereto, followed by allowing to stand at room temperature under shading for 3 hours. Thereafter, a wavelength of 650 to 685 nm which was excited with a 633 nm He/Ne laser was measured by an 8200 Cellular Detection System (manufactured by Applied Biosystems). Hereinafter, this measurement method is referred to as FMAT method.

(6) Construction of Hybridoma
Mouse spleen cells obtained in Section Example 3(2) and myeloma cells obtained in Example 3(4) were mixed at a ratio of 10:1 and centrifuged at 1,200 rpm for 5 minutes. The cell group of the resulting precipitation fraction was well loosened. A mixture of 1 g of polyethylene glycol-1000 (PEG-1000), 1 mL of Minimum Essential Medium (hereinafter, referred to as "MEM") and 0.35 mL of dimethyl sulfoxide (DMSO) was added thereto at 0.5 mL/$1 \times 10^8$ mouse spleen cells and at 37° C. under stirring, and 1 mL of MEM was added several times to the suspension every 1 minute. Then, MEM was added to give a total volume of 50 mL. The cell suspension was centrifuged (900 rpm, 5 minutes), and cells of the resulting precipitation fraction were slowly loosened and then slowly suspended in 100 mL of HAT medium [HAT Media Supplement (manufactured by Invitrogen) was added to RPMI 1640 medium supplemented with 10% fetal bovine serum]. The suspension was dispensed into a 96-well culture plate at 200 μL/well and cultured in a 5% $CO_2$ incubator at 37° C. for 10 to 14 days. After the culture, the culture supernatant was measured according to the FMAT method described in Example 3(5), and a well which was reactive to the CHO/CD4 prepared in Example 1 and was not reactive to the CHO/DG44 cell was selected. Then, the selected cells producing a CD4-specific antibody were subjected to cloning by a limiting dilution method twice to establish hybridomas KM4065, KM4066, KM4067, KM4068 and KM4069 which produce anti-CD4 rat monoclonal antibodies.

EXAMPLE 4

Activity Evaluation for Anti-CD4 Rat Monoclonal Antibody
(1) Reactivity of Anti-CD4 Rat Monoclonal Antibody for Human CD4-Positive Cell Line by FCM
Cells were blocked by adding 1 mg/mL of human IgG (manufactured by Sigma) to 1 to $5 \times 10^5$ cells of the human T cell lymphoma cell line HPB-ALL. Anti-CD4 rat monoclonal antibodies KM4065 to KM4069 and an anti-CD4 mouse antibody OKT4 (manufactured by BioLegend) were appropriately diluted with BSA-PBS and added thereto to give a total volume of 50 µL. These cell suspensions were allowed to react on ice for 60 minutes, and the cells were washed two times with BSA-PBS. To the cells, 50 µL of Alexa-488-labeled anti-rat IgG (H+L) goat antibody (manufactured by Invitrogen) diluted with BSA-PBS was added, followed by reaction on ice for 40 minutes. The cells were washed once with BSA-PBS and suspended in BSA-PBS, and the fluorescence intensity was measured by a flow cytometer (manufactured by Beckman Coulter).

Figure 3:
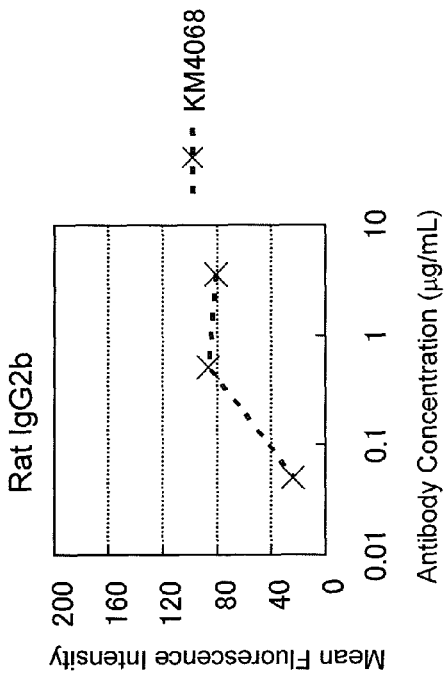
FIGS. 3(A) to 3(D) show the reactivity of an anti-CD4 rat monoclonal antibody and an anti-CD4 mouse antibody OKT4 for the human T cell lymphoma cell line HPB-ALL in the FCM analysis. The graph is divided into (A) to (D) according to the subclass of antibodies. The abscissa represents a concentration of each of the antibodies, and the ordinate represents the mean fluorescence intensity, MFI value.
Figure 3:
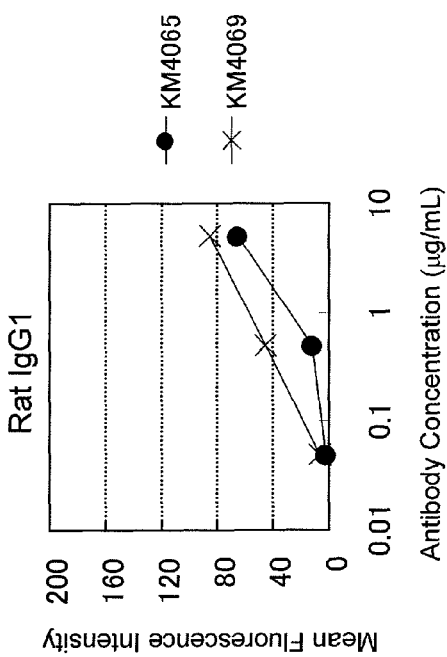
Figure 3:
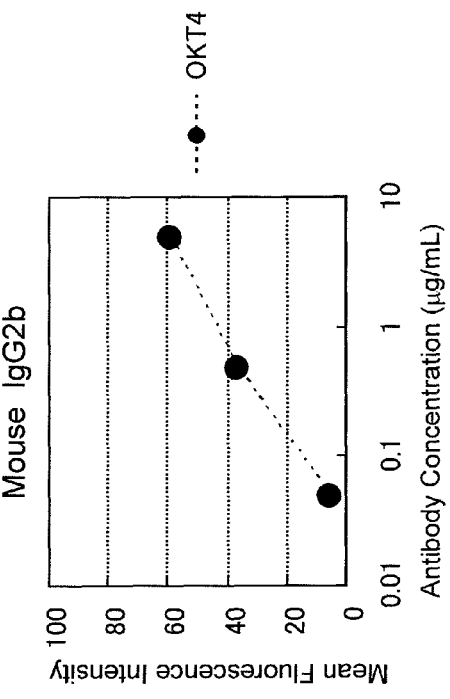
Figure 3:
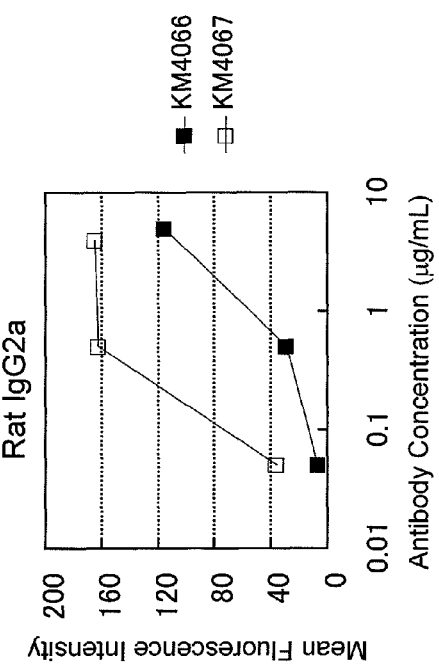

FIG. 3 shows the mean fluorescence intensity (MFI value) when the monoclonal antibody was reacted at a concentration of 5, 0.5, and 0.05 µg/mL. It was demonstrated that all of the anti-CD4 rat monoclonal antibodies KM4065 to KM4069, and the anti-CD4 mouse antibody OKT4 bind to the CD4-positive cell line in an antibody concentration-dependent manner.

(2) Binding Activity of Anti-CD4 Rat Monoclonal Antibody to Recombinant Human CD4 by Biacore In order to kinetically analyze the binding activity of anti-CD4 rat monoclonal antibodies KM4065 to KM4069 and commercially available anti-human CD4 mouse antibody for recombinant human CD4, the binding activity was measured by surface plasmon resonance method (SPR). All of the following manipulations were carried out using the Biacore T100 (manufactured by GE Healthcare Bio-Sciences). The anti-mouse IgG antibody was immobilized on a CM5 sensor chip (manufactured by GE Healthcare Bio-Sciences) by an amine coupling method using a Mouse Antibody Capture Kit (manufactured by GE Healthcare Bio-Sciences) in accordance with the protocols attached thereto. Anti-CD4 rat monoclonal antibodies KM4065 to KM4069, Leu-3a (BD Biosciences), OKT4 (BioLegend) and 13B8.2 (Beckman Coulter) were added to be captured on the anti-mouse IgG antibody-immobilized chip to give 100 RU (resonance unit), respectively. Thereafter, the recombinant human CD4 (manufactured by R&D) diluted from 2500 ng/mL in five steps was allowed to run at a flow rate of 30 µL/min onto the chip, and the sensorgram corresponding to each concentration was obtained. The analysis was carried out in the 1:1 binding model using an analysis software attached to the apparatus, thereby calculating an association rate constant ka and a dissociation rate constant kd of individual antibodies for the human CD4.

As a result, an association rate constant (hereinafter, referred to as "ka"), a dissociation rate constant (hereinafter, referred to as "kd") and a dissociation constant $K_D$ (kd/ka) of individual antibodies thus obtained are given in Table 2.

As shown in Table 2, the anti-CD4 rat monoclonal antibodies KM4065 and KM4066 exhibited a higher affinity than the conventional antibody.

TABLE 2

| Antibody | ka (1/Ms) | kd (1/s) | $K_D$ (M) |
|---|---|---|---|
| KM4065 | 3.57E+05 | 1.52E−06 | 4.26E−12 |
| KM4066 | 1.34E+06 | 1.18E−04 | 8.82E−11 |
| KM4067 | 8.75E+05 | 4.73E−04 | 5.41E−10 |
| KM4068 | 1.85E+06 | 2.04E−03 | 1.10E−09 |
| KM4069 | 1.21E+06 | 5.84E−04 | 4.82E−10 |
| Leu-3a* | 1.10E+06 | 1.29E−04 | 1.17E−10 |
| OKT4** | 1.05E+06 | 3.06E−03 | 2.90E−09 |
| 13B8.2*** | 4.44E+05 | 1.56E−04 | 3.52E−10 |

*manufactured by BD Bioscience,
**manufactured by Biolegend,
***manufactured by Beckman Coulter (3) Evaluation of Complement-Dependent Cellular Cytotoxicity (CDC Activity) of Anti-CD4 Rat Monoclonal Antibody on CD4 Transfectant The CDC activity of the anti-CD4 rat monoclonal antibodies KM4066 to KM4068 and the anti-CD4 mouse antibody OKT4 on the CD4 transfectant constructed in Example 1 was measured using a culture supernatant of the rat hybridoma, according to the following procedure.

The CD4 transfectant was washed with PBS, washed with RPMI 1640 medium (manufactured by Wako Pure Chemical) containing 10% fetal bovine serum (FBS), and prepared to give an optimum concentration in the same medium, which was then used as a target cell suspension. The target cell suspension was dispensed into a 96-well flat-bottom plate (manufactured by Sumitomo Bakelite) at $5 \times 10^4$ cells/well. In addition, an anti-CD4 chimeric antibody solution prepared to give an appropriate concentration and a human complement (manufactured by Sigma) at a final concentration of 25% were added thereto to give a total volume of 100 µL/well. In addition, a reaction well not containing the antibody (0% cellular cytotoxicity well) as a negative control, and a reaction well not containing the cell (100% cellular cytotoxicity well) as a positive control were respectively prepared. The reaction was carried out in a 5% $CO_2$ incubator at 37° C. for 3 hours. After the reaction was complete, 10 µL/well of a WST-1 reagent (manufactured by Roche Diagnostics) was added to the reaction wells, followed by reaction at 37° C. for 3 hours. An absorbance at 450 nm (OD450) for each well was measured using a plate reader Emax (manufactured by Molecular Devices). From the absorbance of each well, the CDC activity (cellular cytotoxicity [%]) was calculated according to the following formula.

CDC activity (cellular cytotoxicity [%])=100×{1−(absorbance of reaction well−absorbance of 100% lysis well)/(absorbance of 0% lysis well−absorbance of 100% lysis well)}  (Formula)

Figure 4:
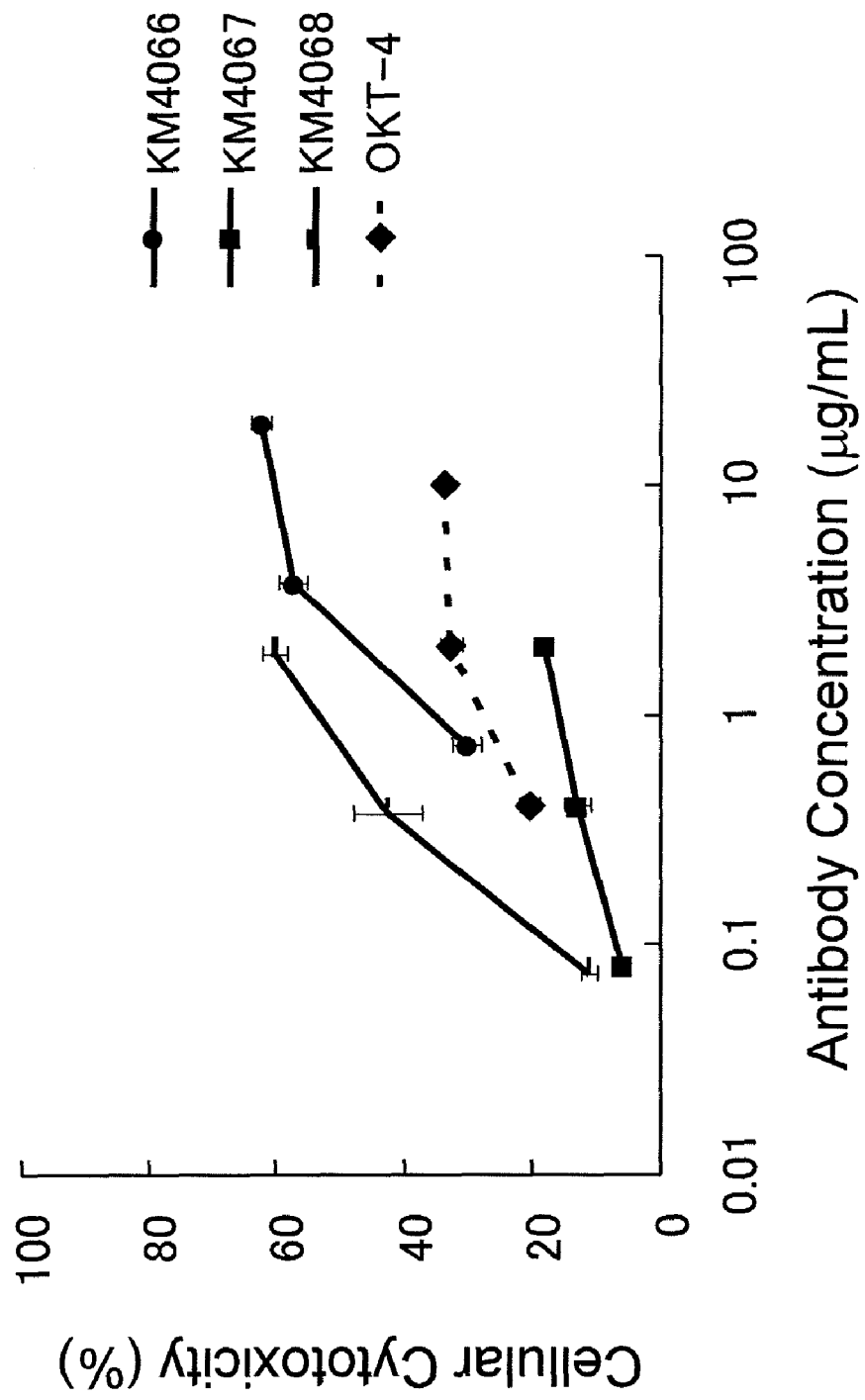
FIG. 4 shows a complement-dependent cellular cytotoxicity (CDC activity) of an anti-CD4 rat monoclonal antibody and an anti-CD4 mouse monoclonal antibody OKT4 on a CD4-expressing transfectant. The ordinate represents a cellular cytotoxicity rate (%), and the abscissa represents an antibody concentration of an anti-CD4 monoclonal antibody. ● represents an anti-CD4 rat monoclonal antibody KM4066, ■ represents an anti-CD4 rat monoclonal antibody KM4067, – represents an anti-CD4 rat monoclonal antibody KM4068, and ♦ represents an anti-CD4 mouse monoclonal antibody OKT4.

The measurement results are shown in FIG. 4. As shown in FIG. 4, the conventional anti-CD4 mouse antibody OKT4 had a CDC activity, and similarly all the clones of the anti-CD4 rat monoclonal antibodies KM4066 to KM4068 obtained in the present invention also exhibited a CDC activity.

EXAMPLE 5

Isolation and Analysis of cDNA Encoding Variable Region of Anti-CD4 Monoclonal Antibody (1) Preparation of mRNA from Anti-CD4 Monoclonal Antibody-Producing Hybridoma Cell From $5 \times 10^7$ to $1 \times 10^8$ cells of the respective hybridomas KM4065 to KM4069 obtained in Example 3, mRNA of the respective anti-CD4 rat monoclonal antibodies was prepared using RNAeasy Mini kit (manufactured by Qiagen) and Oligotex™-dT30 <Super> mRNA Purification Kit (manufactured by Takara) in accordance with the instructions attached thereto.

(2) Gene Cloning of H Chain and L Chain Variable Regions of Anti-CD4 Monoclonal Antibody Using a SMART RACE cDNA Amplification Kit (manufactured by Clontech) in accordance with the instructions attached thereto, a cDNA was obtained from 0.5 µg of mRNA of the monoclonal antibody obtained in Example 5(1). cDNA fragments of heavy chain variable regions (hereinafter referred to as "VH") of the respective antibodies were amplified by carrying out PCR using the thus obtained cDNA as a template, and using a universal primer Amix attached to the kit and one selected from a rat IgG1-specific primer (SEQ ID NO:3), a rat IgG2a-specific primer (SEQ ID NO:4), and an IgG2b-specific primer (SEQ ID NO:5). Also, cDNA fragments of light chain variable regions (hereinafter, referred to as "VL") of the respective antibodies were amplified by carrying out PCR using a rat Ig(κ)-specific primer (SEQ ID NO:6) instead of the respective subclass-specific primers of the antibody. PCR for any antibody subclass was carried out by heating at 94° C. for 5 minutes; 5 cycles each consisting of reaction at 94° C. for 15 seconds and reaction at 72° C. for 3 minutes; 5 cycles each consisting of reaction at 94° C. for 15 seconds, reaction at 70° C. for 30 seconds, and reaction at 72° C. for 3 minutes; and 30 cycles each consisting of reaction at 94° C. for 15 seconds, reaction at 68° C. for 30 seconds, and reaction at 72° C. for 3 minutes, followed by reaction at 72° C. for 10 minutes. The PCR was carried out using the PTC-200 DNA Engine (manufactured by Bio-Rad).

Figure 5:
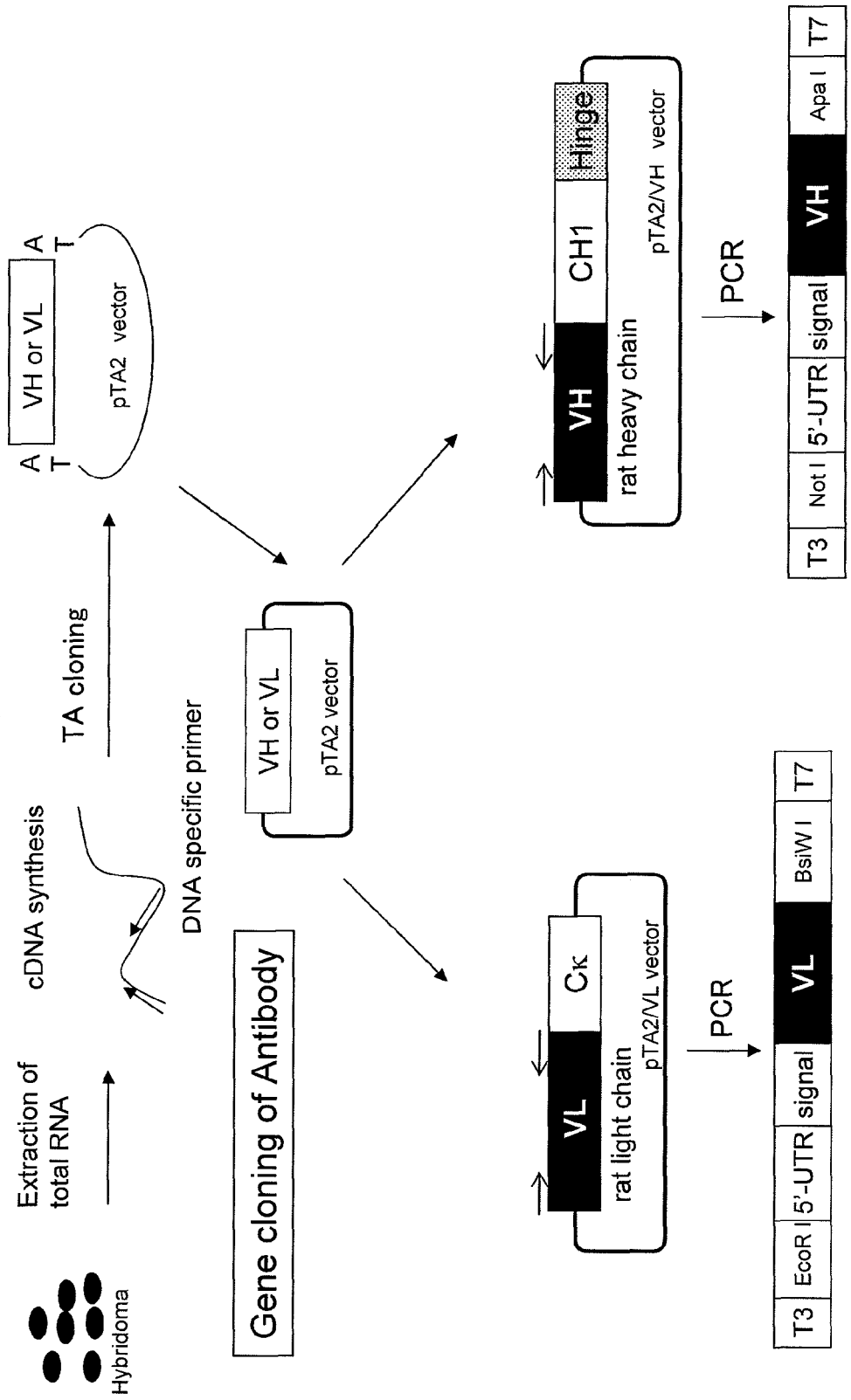
FIG. 5 shows a cloning process of an anti-CD4 rat monoclonal antibody.

Next, in order to determine the nucleotide sequence by cloning, the obtained PCR product was separated by agarose gel electrophoresis, and each of a VH gene fragment and a VL gene fragment was extracted using a Gel Extraction Kit (manufactured by Qiagen). Then, deoxyadenine (dA) was added to the extracted fragment, using a Target Clone Plus (manufactured by Toyobo) in accordance with the instructions attached thereto, and VH or VL of each antibody was incorporated into a pTA2 vector. An *Escherichia coli* DH5α strain was transformed with the obtained vector in accordance with the instructions attached to a Competent Quick (manufactured by Toyobo). A plasmid was extracted from the resulting transformant using an automated plasmid isolation system (manufactured by Kurabo). The extracted plasmid was allowed to react using a Big Dye Terminator Cycle Sequencing FS Ready Reaction Kit (manufactured by PE Biosystems) in accordance with the instructions attached thereto and then the nucleotide sequence of the cloned PCR product was analyzed using a sequencer of the same company, ABI PRISM3700. As a result, a plasmid containing a full-length VH cDNA, and a plasmid containing a VL cDNA were obtained, in which an ATG sequence presumed to be an initiation codon was present at the 5' terminal of cDNA. A scheme of cloning is shown in FIG. 5.

(3) Analysis of Nucleotide Sequence of Anti-CD4 Monoclonal Antibody Variable Region Complete nucleotide sequences of VH of the anti-CD4 rat monoclonal antibodies KM4065 to KM4069 comprised in the plasmid obtained in Example 5(2) are represented by SEQ ID NOs:7 to 11, respectively, complete amino acid sequences of VH including a signal sequence deduced from these nucleotide sequences are represented by SEQ ID NOs:12 to 16, respectively, complete nucleotide sequences of VL are represented by SEQ ID NOs:17 to 21, respectively, and complete amino acid sequence of VL including a signal sequence deduced from these nucleotide sequences are represented by SEQ ID NOs:22 to 26, respectively. From the comparison of the obtained analysis results with the sequence data [*SEQUENCES of Proteins of Immunological Interest*, US Dept. Health and Human Services (1991)] of known rat antibodies, it has become clear that each of the isolated cDNAs is a full-length cDNA encoding a variable region (hereinafter, referred to as "V region") of anti-CD4 rat monoclonal antibodies KM4065 to KM4069 containing a secretory signal sequence; in the H chain of KM4065, the amino acid sequence from positions 1 to 19 in the amino acid sequence represented by SEQ ID NO:12 is the secretory signal sequence; in the L chain of KM4065, the amino acid sequence from positions 1 to 20 in the amino acid sequence represented by SEQ ID NO:22 is the secretory signal sequence; in the H chain of KM4066, the amino acid sequence from positions 1 to 19 in the amino acid sequence represented by SEQ ID NO:13 is the secretory signal sequence; in the L chain of KM4066, the amino acid sequence from positions 1 to 19 in the amino acid sequence represented by SEQ ID NO:23 is the secretory signal sequence; in the H chain of KM4067, the amino acid sequence from positions 1 to 18 in the amino acid sequence represented by SEQ ID NO:14 is the secretory signal sequence; in the L chain of KM4067, the amino acid sequence from positions 1 to 20 in the amino acid sequence represented by SEQ ID NO:24 is the secretory signal sequence; in the H chain of KM4068, the amino acid sequence from positions 1 to 19 in the amino acid sequence represented by SEQ ID NO:15 is the secretory signal sequence; in the L chain of KM4068, the amino acid sequence from positions 1 to 20 in the amino acid sequence represented by SEQ ID NO:25 is the secretory signal sequence; in the H chain of KM4069, the amino acid sequence from positions 1 to 19 in the amino acid sequence represented by SEQ ID NO:16 is the secretory signal sequence; and, in the L chain of KM4069, the amino acid sequence from positions 1 to 20 in the amino acid sequence represented by SEQ ID NO:26 is the secretory signal sequence.

Then, the novelty of amino acid sequences of VH and VL of anti-CD4 rat monoclonal antibodies KM4065 to KM4069 was investigated. Using a GCG Package (version 9.1, manufactured by Genetics Computer Group) as a sequence analysis system, the amino acid sequence database of conventional proteins was retrieved by BLASTP method [Nucleic Acids Res., 25, 3389 (1997)]. As a result, completely coinciding amino acid sequences were not found for both of the VH and VL, so that it was confirmed that the VH and VL of the anti-CD4 rat monoclonal antibodies KM4065 to KM4069 have novel amino acid sequences.

Further, CDRs of VH and VL of respective monoclonal antibodies were identified by comparing them with the amino acid sequences of known antibodies. Amino acid sequences of CDR1, CDR2 and CDR3 of VH of the anti-CD4 rat monoclonal antibody KM4065 were represented by SEQ ID NOs: 27, 28 and 29, respectively, and amino acid sequences of CDR1, CDR2 and CDR3 of VL thereof are represented by SEQ ID NOs:30, 31 and 32, respectively. Amino acid sequences of CDR1, CDR2 and CDR3 of VH of the anti-CD4 rat monoclonal antibody KM4066 were represented by SEQ ID NOs:33, 34 and 35, respectively, and amino acid sequences of CDR1, CDR2 and CDR3 of VL thereof were represented by SEQ ID NOs:36, 37 and 38, respectively. Amino acid sequences of CDR1, CDR2 and CDR3 of VH of the anti-CD4 rat monoclonal antibody KM4067 were represented by SEQ ID NOs:39, 40 and 41, respectively, and amino acid sequences of CDR1, CDR2 and CDR3 of VL thereof are represented by SEQ ID NOs:42, 43 and 44, respectively. Amino acid sequences of CDR1, CDR2 and CDR3 of VH of the anti-CD4 rat monoclonal antibody KM4068 were represented by SEQ ID NOs:45, 46 and 47, respectively, and amino acid sequences of CDR1, CDR2 and CDR3 of VL thereof were represented by SEQ ID NOs:48, 49 and 50, respectively. Amino acid sequences of CDR1, CDR2 and CDR3 of VH of the anti-CD4 rat monoclonal antibody KM4069 were represented by SEQ ID NOs:51, 52 and 53, respectively, and amino acid sequences of CDR1, CDR2 and CDR3 of VL thereof were represented by SEQ ID NOs:54, 55 and 56, respectively.

EXAMPLE 6

Figure 6:
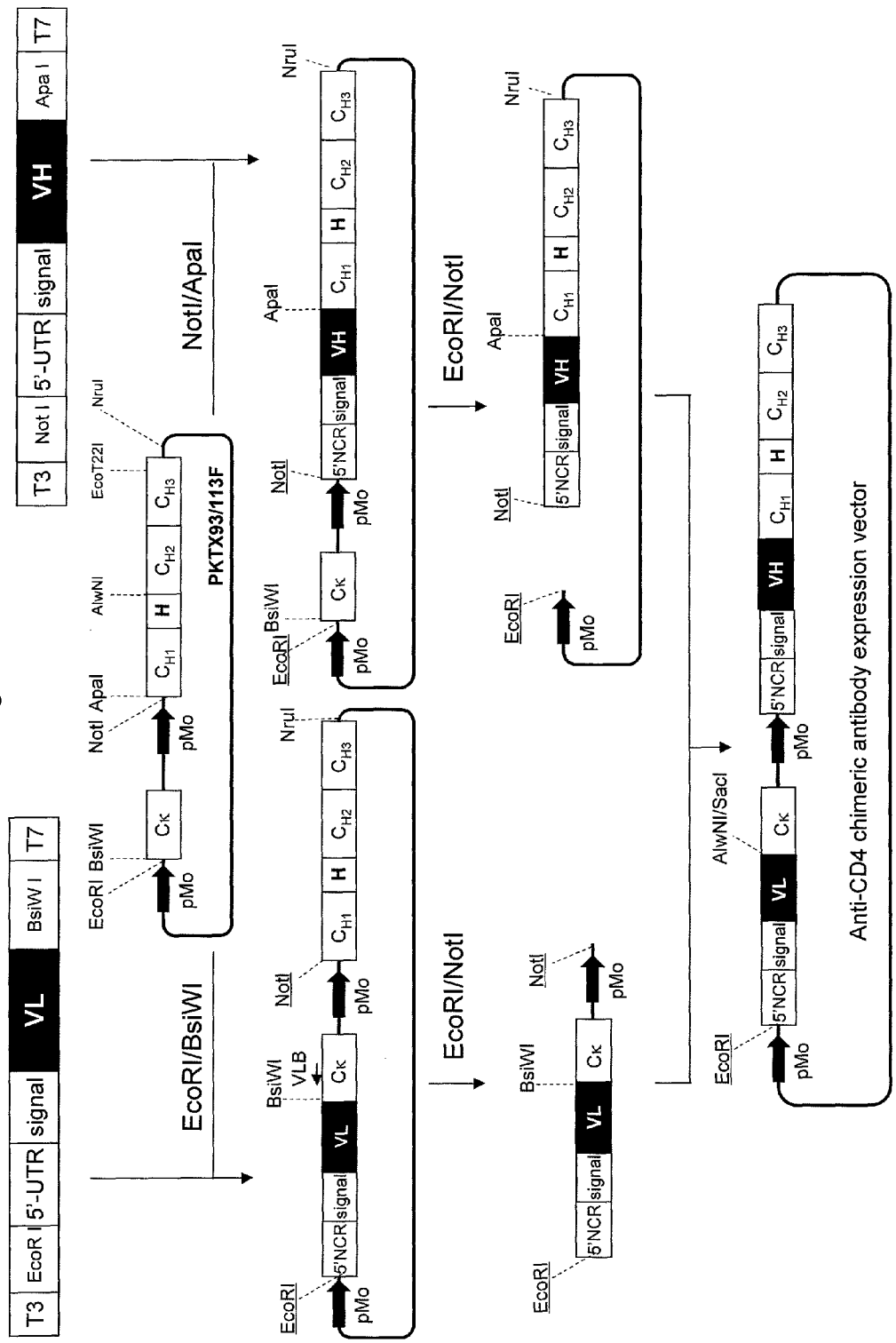
FIG. 6 shows a construction process of an anti-CD4 chimeric antibody expression vector.

Preparation of Anti-CD4 Chimeric Antibody (1) Construction of Anti-CD4 Chimeric Antibody Expression Vector The chimeric antibody prepared in the present invention is a chimeric antibody in which a heavy chain constant region (hereinafter, referred to as "113F type") having a high CDC activity and comprising an amino acid sequence in which a part of an Fc region of a human IgG1 antibody is substituted with Fc of a human IgG3 antibody disclosed in US2007/0148165, and a light chain constant region of human κ were respectively ligated to variable regions of heavy and light chains of the anti-CD4 rat monoclonal antibody obtained in Example 5(2). For this purpose, using a high-CDC type chimeric antibody expression vector PKTX93/113F (described in US2007/0148165) comprising a variable region of an anti-CD20 antibody, and a pTA2 vector comprising VH or VL of each monoclonal antibody obtained in Example 5(2), an anti-CD4 chimeric antibody expression vector was constructed in accordance with the following procedure (FIGS. 5 and 6).

A reaction solution (50 μL) containing 100 ng of the TA2 vector containing VH or VL of each monoclonal antibody as a template, 5 μL of 10×KOD Plus buffer, 5 μL of 2 mmol/L dNTPs, 2 μL of 25 mmol/L magnesium chloride, 2.5 μL of DMSO, 1 μL of KOD Plus polymerase (manufactured by Toyobo), and 1 μL of each of 10 μmol/L primers specific to VH and VL of each anti-CD4 rat monoclonal antibody was prepared. Using the thus prepared solution, PCR was carried out as follows: heating at 94° C. for 2 minutes, followed by 30 cycles each consisting of reaction at 94° C. for 15 seconds, reaction at 60.6° C. for 30 seconds, and reaction at 68° C. for 1 minute. Primers of VH of KM4065 are represented by SEQ ID NOs:57 and 58, and primers of VL thereof are represented by SEQ ID NOs:59 and 60; primers of VH of KM4066 are represented by SEQ ID NOs:61 and 62, and primers of VL thereof are represented by SEQ ID NOs:63 and 64; primers of VH of KM4067 are represented by SEQ ID NOs: 65 and 66, and primers of VL thereof are represented by SEQ ID NOs:67 and 68; primers of VH of KM4068 are represented by SEQ ID NOs:69 and 70, and primers of VL thereof are represented by SEQ ID NOs:71 and 72; and primers of VH of KM4069 are represented by SEQ ID NOs:73 and 74, and primers of VL thereof are represented by SEQ ID NOs:75 and 76.

Each PCR product was purified using a PCR Purification Kit (manufactured by Qiagen). The obtained VH of each antibody was treated with restriction enzymes ApaI (manufactured by New England Biolabs) and NotI (manufactured by New England Biolabs), thereby obtaining a NotI-ApaI fragment of VH. In addition, VL of each antibody was treated with restriction enzymes BsiWI (manufactured by New England Biolabs) and EcoRI (manufactured by New England Biolabs), thereby obtaining an EcoRI-BsiWI fragment of VL. Furthermore, the high-CDC type chimeric antibody expression vector PKTX93/113F was also subjected to treatments with restriction enzymes NotI and ApaI, or EcoRI and BsiWI. As with the procedure described in Example 1(1), a vector into which a cDNA encoding VH of anti-CD4 rat monoclonal antibodies KM4065 to KM4069 was cloned, and a vector into which a cDNA encoding VL of each of anti-CD4 monoclonal rat antibodies KM4065 to KM4069 was cloned were obtained. Restriction enzymes EcoRI and NotI were added to treat the obtained PKTX93/113F vector into which VH or VL of each antibody was incorporated, thereby obtaining an NotI-EcoRI fragment of the PKTX93/113F vector into which an EcoRI-NotI fragment of VL and VH were incorporated. As with the procedure described in Example 1(1), an anti-CD4 chimeric antibody expression vector was obtained into which each of cDNAs encoding VH and VL of each of anti-CD4 rat monoclonal antibodies KM4065 to KM4069 was cloned. A scheme for the construction of the vector is shown in FIG. 6. In addition, anti-CD4 chimeric antibodies prepared from the anti-CD4 rat monoclonal antibodies KM4065 to KM4069 are defined as anti-CD4 chimeric antibodies KM4045 to KM4049, respectively (Table 3).

TABLE 3

| Rat monoclonal antibody | Chimeric antibody |
|---|---|
| KM4065 | KM4045 |
| KM4066 | KM4046 |
| KM4067 | KM4047 |
| KM4068 | KM4048 |
| KM4069 | KM4049 |

(2) Expression of Anti-CD4 Chimeric Antibody Using Animal Cells

Using the anti-CD4 chimeric antibody expression vector obtained in Example 6(1), the anti-CD4 chimeric antibody in an animal cell was expressed by a conventional method [Antibody Engineering, A Practical Guide, W.H. Freeman and Company (1992)] to obtain transformants KM4045 to KM4049 which produce anti-CD4 chimeric antibodies. As an animal cell for expressing the desired antibody, a CHO/DG44 cell line in which a gene of α1,6-fucosyltransferase (FUT8) was double-knockout (hereinafter, referred to as "FUT8 knockout CHO cell") was used. It is known that fucose is not added to a core structure of a complex type N-glycoside-linked sugar chain of the antibody expressed in this host cell (WO2002/31140).

(3) Obtaining of Purified Chimeric Antibody

After culturing each of the transformants KM4045 to KM4049 obtained in Section (2) by a conventional culturing method, cell suspensions were recovered and centrifuged at 3000 rpm and 4° C. for 20 minutes to recover the culture supernatants. Then, the culture supernatants were filtration-sterilized using a 0.22-μm pore size Millex GV filter (manufactured by Millipore). The anti-CD4 chimeric antibodies KM4045 to KM4049 were purified from the obtained culture supernatants, using a Protein A High-capacity resin (manufactured by Millipore) column in accordance with the instructions attached thereto.

(4) Preparation of IgG1 Type Antibody and 113F Type Antibody of Anti-CD4 Human Antibody 6G5

In order to compare the activity of the anti-CD4 monoclonal antibody of the present invention, two antibodies (hereinafter, referred to as "6G5-1" and "6G5-113F") comprising a variable region of the conventional anti-CD4 human antibody 6G5 and a conventional human IgG Fc region or a high-CDC activity 113F type Fc region were prepared.

Figure 7:
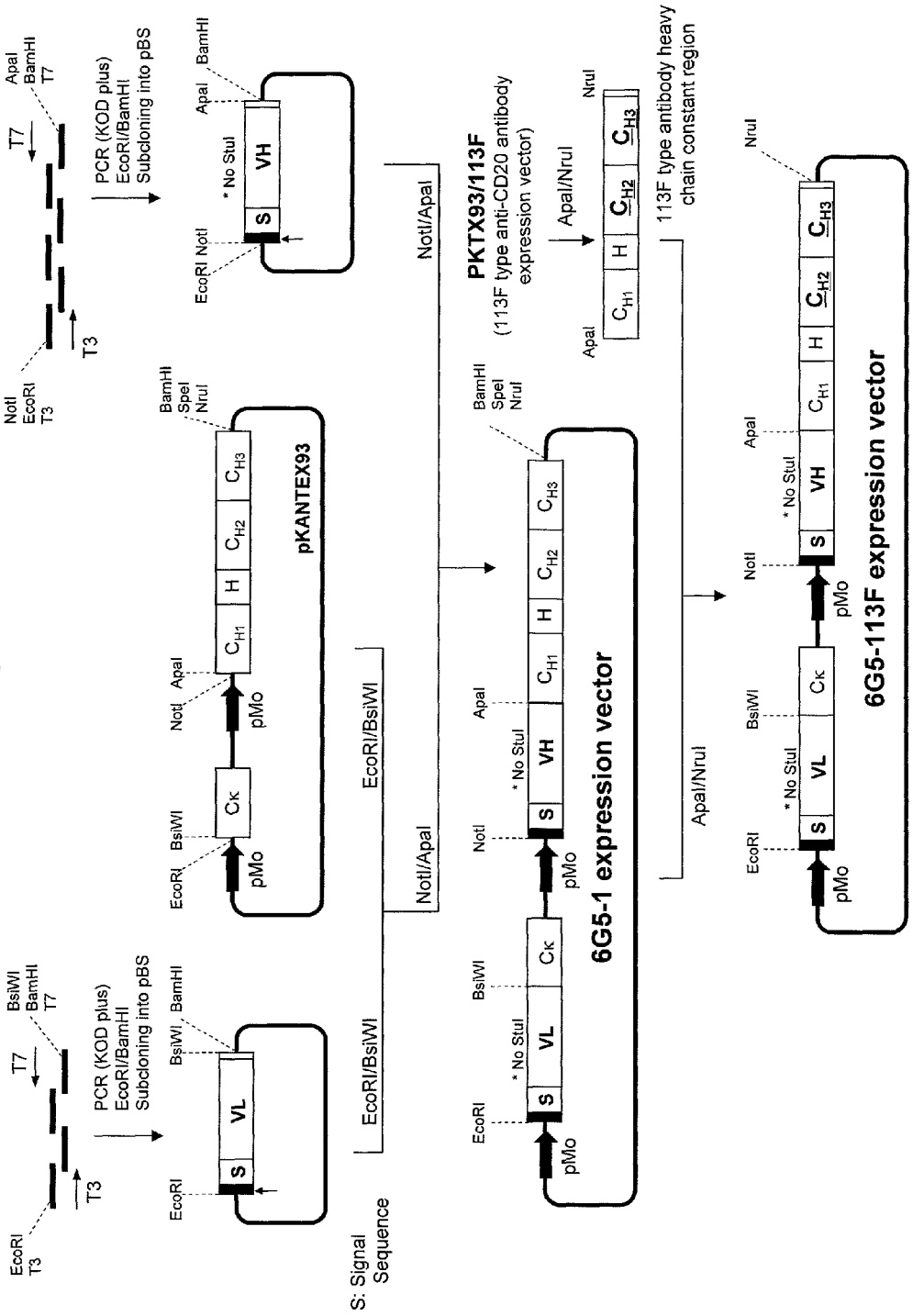
FIG. 7 shows a construction process of expression vectors of anti-CD4 human antibodies 6G5-1 and 6G5-113F.

A gene encoding VH and VL of the anti-CD4 human antibody 6G5 was constructed by carrying out PCR using the synthetic oligo DNAs represented by SEQ ID NOs:89 to 92, the synthetic oligo DNAs represented by SEQ ID NOs:83 to 88, and a T3 primer and a T7 primer positioned at both ends of the variable region, based on the sequence information disclosed in US20060183195. The PCR-amplified VH or VL gene fragment of the 6G5 antibody was ligated into a pBluescript II sk(−) vector (manufactured by Stratagene) for subcloning. Subsequently, as with the procedure in Example 1 or Example 6(2), a 6G5.1-1 expression vector and a 6G5.1-113F expression vector were constructed (FIG. 7). The constructed 6G5.1-1 expression vector was expressed in both the CHO/DG44 cell and the FUT8 knockout CHO cell (WO2002/

31140), and the 6G5.1-113F expression vector was expressed in the FUT8 knockout CHO cell. Introduction of the expression vector, obtaining of the expression cell strain, cell culture, and purification of antibodies were carried out in the same manner as in Example 6(2) and (3). As a result, a 6G5-1 antibody (hereinafter, referred to as "6G5-1") in which fucose is bound to N-acetylglucosamine in the reducing end in a complex type N-glycoside-linked sugar chain of the antibody through α-1,6 bond, a 6G5-1 antibody (hereinafter, referred to as "6G5-P") to which fucose is not bound thereto, and a 6G5-113F antibody (hereinafter, referred to as "6G5-113F") in which fucose is not bound to a complex type N-glycoside-linked sugar chain of the Fc region of the antibody were obtained.

(5) Determination of Fucose Content in Anti-CD4 Chimeric Antibody

In accordance with the method described in WO2002/31140, a ratio of a sugar chain in which 1-position of fucose is not bound to 6-position of N-acetylglucosamine in the reducing end in the complex type N-glycoside-linked sugar chain of the Fc region of each anti-CD4 chimeric antibody and 6G5-1 antibody through α-bond to the entire was examined. The results are shown in Table 4.

From these results, it was demonstrated that fucose was not added to the chimeric antibody prepared in Example 6(3).

TABLE 4

| Fucose content in anti-CD4 chimeric antibody | |
|---|---|
| KM4045 | 0% |
| KM4046 | 0% |
| KM4047 | 0% |
| KM4048 | 0% |
| KM4049 | 0% |
| 6G5-1 | 100% |

EXAMPLE 7

Evaluation of Activity of Anti-CD4 Chimeric Antibody

In the following sections (1) to (4), the activity evaluation was carried out for the anti-CD4 chimeric antibodies KM4045 to KM4049 obtained in Example 6 and 6G5-1, 6G5-P and 6G5-113F prepared in Example 6(5).

Figure 8:
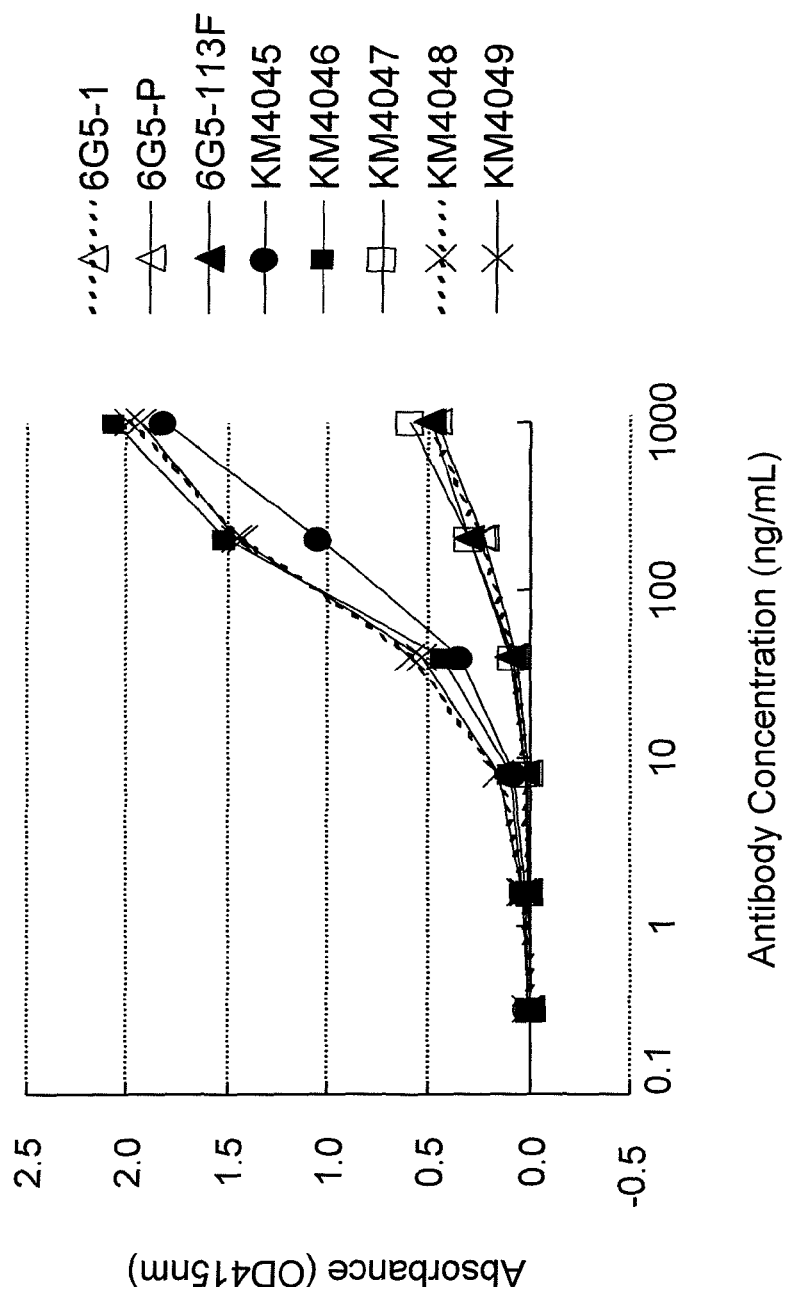
FIG. 8 shows the reactivity of various anti-CD4 antibodies in the binding ELISA. The abscissa represents a concentration of each of the antibodies, and the ordinate represents a binding activity of each of the antibodies. The reactivity of each antibody against recombinant human CD4 is shown. Δ in the broken line represents a monoclonal antibody 6G5-1, Δ in the solid line represents an anti-CD4 human antibody 6G5-P, ▲ represents an anti-CD4 human antibody 6G5-113F, ● represents an anti-CD4 chimeric antibody KM4045, ■ represents an anti-CD4 chimeric antibody KM4046, □ represents an anti-CD4 chimeric antibody KM4047, × in the broken line represents an anti-CD4 chimeric antibody KM4048, and × in the solid line represents an anti-CD4 chimeric antibody KM4049.

(1) Evaluation of Binding Activity of Anti-CD4 Chimeric Antibody to Recombinant Human CD4 by Binding ELISA The binding ELISA was carried out as in the same procedure as described in Example 2(3). As the primary antibody, the anti-CD4 chimeric antibodies KM4045 to KM4049 obtained in Example 6, and 6G5-1, 6G5-P and 6G5-113F, which were serially 5-fold diluted from 1 µg/mL, were used. The results are shown in FIG. 8.

As a result, all of the anti-CD4 chimeric antibodies KM4045 to KM4049, 6G5-1, 6G5-P and 6G5-113F were found to bind to the recombinant human CD4. In addition, the anti-CD4 chimeric antibodies KM4045, KM4046, KM4048 and KM4049 were found to bind to the recombinant CD4 more strongly than 6G5-1, 6G5-P and 6G5-113F.

(2) Biacore-Based Evaluation of Binding Activity of Anti-CD4 Chimeric Antibody to Recombinant Human CD4

In order to kinetically analyze the binding activity of anti-CD4 chimeric antibodies KM4045 to KM4049, 6G5-1 and 6G5-P to recombinant human CD4, the binding activity was measured by surface plasmon resonance method (SPR). All of the following manipulations were carried out using a Biacore T100 (manufactured by GE Healthcare Bio-Sciences). The anti-human IgG antibody was immobilized on a CM5 sensor chip (manufactured by GE Healthcare Bio-Sciences) by an amine coupling method using a Human Antibody Capture Kit (manufactured by GE Healthcare Bio-Sciences) in accordance with the protocols attached thereto. An assay sample (anti-CD4 chimeric antibodies KM4045 to KM4049) was added to be captured on the anti-human IgG antibody-immobilized chip to give 100 RU (resonance unit). Thereafter, the recombinant human CD4 (manufactured by R&D) diluted from 2500 ng/mL in five steps was allowed to run at a flow rate of 30 µL/min onto the chip, and the sensorgram corresponding to each concentration was obtained. The analysis was carried out in the 1:1 binding model using an analysis software attached to the apparatus, Biacore T100 Evaluation software (manufactured by Biacore), thereby calculating an association rate constant ka and a dissociation rate constant kd of respective antibodies for human CD4.

As a result, an association rate constant ka, a dissociation rate constant kd, and a dissociation constant $K_D$ (kd/ka) of individual antibodies thus obtained are given in Table 5.

As shown in Table 5, all of the chimeric antibodies KM4045 to KM4049 exhibited a higher affinity than that of the conventional anti-CD4 human antibody 6G5-1.

TABLE 5

| Antibody | ka (1/Ms) | kd (1/s) | $K_D$ (M) |
|---|---|---|---|
| KM4045 | 3.60E+05 | 2.97E−08* | 8.24E−14 |
| KM4046 | 8.34E+05 | 5.12E−05 | 6.14E−11 |
| KM4047 | 1.33E+06 | 4.88E−04 | 3.69E−10 |
| KM4048 | 5.85E+06 | 3.81E−03 | 6.51E−10 |
| KM4049 | 5.77E+06 | 1.16E−03 | 2.00E−10 |
| 6G5-1 | 5.95E+05 | 8.72E−04 | 1.46E−09 |

*KM4045 exhibited slow dissociation and a value which exceeds a measurable limit of a dissociation rate constant kd ($1 \times 10^{-5}$) indicated by the maker in this system.

(3) Evaluation of Antibody-Dependent Cellular Cytotoxicity (ADCC Activity) of Anti-CD4 Chimeric Antibody on Human Blood Cancer Cell Lines The ADCC activity of the anti-CD4 chimeric antibodies KM4045 to KM4049, 6G5-1, 6G5-P, and 6G5-113F on the human T cell lymphoma cell lines was measured in the following manner.

(3)-1 Preparation of Target Cell Suspension

Human T cell lymphoma cell lines HPB-ALL and HUT78, and T cell lymphoblastic lymphoma cell line SUP-T1 were washed with PBS, washed with a phenol red-free RPMI1640 medium (manufactured by Invitrogen, hereinafter referred to as "ADCC medium") containing 5% dialyzed fetal bovine serum (dFBS, manufactured by Invitrogen) (hereinafter, referred to as "ADCC medium"), and then suspended in the same medium to give an optimum concentration and used as a target cell suspension.

(3)-2 Preparation of Effector Cell Suspension

From healthy human peripheral blood, peripheral blood mononuclear cells (PBMCs) were isolated in the following manner. From healthy volunteers, 50 mL of healthy human peripheral blood was collected using a syringe to which 0.5 mL of heparin sodium (manufactured by Shimizu Pharmaceutical) was added. To the collected peripheral blood was added an equal volume of physiological saline (manufactured by Otsuka Pharmaceutical) to dilute, followed by thoroughly stirring. Then, 4.7 mL of Lymphoprep (manufactured by Axis-Shield) was dispensed into each of 15 mL tubes (manufactured by Greiner). The diluted peripheral blood (10 mL) was gently layered on the Lymphoprep. Next, the mononuclear cell layer was separated by the condition of centrifugation at 2000 rpm, break off, and room temperature for 20 minutes. The thus obtained mononuclear cell fraction was washed twice with an ADCC medium, and then suspended in the same medium to give an optimum cell count and used as an effector cell suspension.

(3)-3 Measurement of ADCC Activity

The ADCC activity was measured by the following procedure, using a CytoTox96 Non-Radioactive Cytotoxicity Assay (manufactured by Promega) in accordance with the instructions attached thereto.

Figure 9:
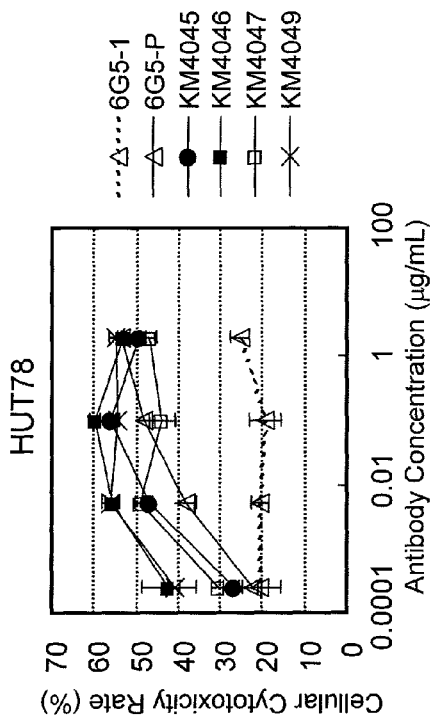
FIGS. 9(A) to 9(D) show an antibody-dependent cellular cytotoxicity (ADCC activity) of various anti-CD4 antibodies on various human T cell lines. The ordinate represents a cellular cytotoxicity rate (%), and the abscissa represents an antibody concentration of each antibody. Δ in the broken line represents a monoclonal antibody 6G5-1, Δ in the solid line represents a monoclonal antibody 6G5-P, ▲ represents a chimeric antibody 6G5-113F, ● represents a chimeric antibody KM4045, ■ represents a chimeric antibody KM4046, □ represents a chimeric antibody KM4047, × in the broken line represents a chimeric antibody KM4048, and × in the solid line represents a chimeric antibody KM4049.
Figure 9:
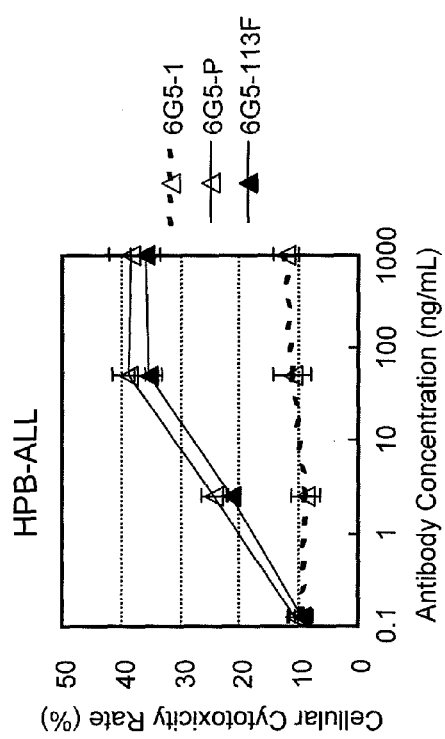
Figure 9:
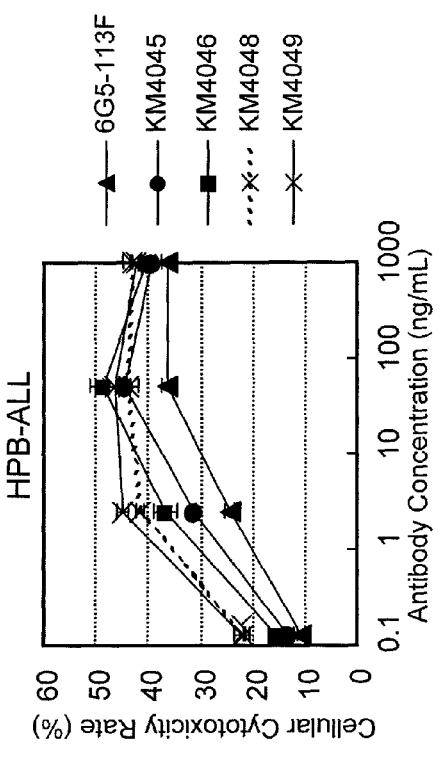
Figure 9:
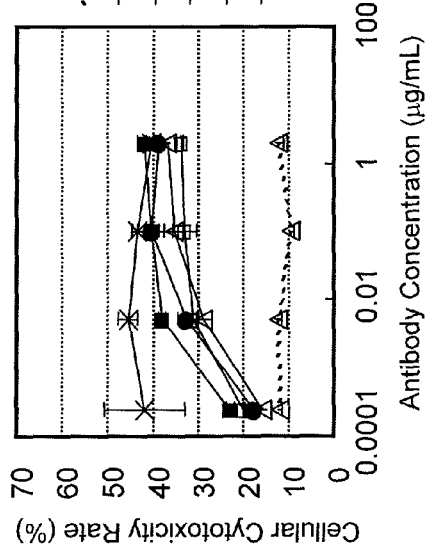

An antibody solution (50 µL/well), in which each antibody was serially 20-fold diluted from 2 µg/mL or 1 µg/mL, was dispensed into a 96-well U bottom plate (manufactured by Falcon). Next, $2.5 \times 10^4$ cells/50 µL/well of the target cell suspension prepared in Section (3)-1 were dispensed thereto. Finally, $2 \times 10^5$ cells/50 µL/well of the effector cell suspension prepared in Section (3)-2 were dispensed thereto to give a total volume of 150 µL, followed by reaction at 37° C. for 4 hours. Therefore, the experiment was carried out at a 8:1 ratio of effector cell (E):target cell (T). The ADCC activity was calculated by the following formula. The results are shown in FIG. 9.

ADCC activity (%)={([absorbance of sample]−[absorbance of target cell spontaneous release]−[absorbance of effector cell spontaneous release])/([absorbance of target cell total release]−[absorbance of target cell spontaneous release])}×100   (Formula)

As a result, the conventional anti-CD4 human antibody 6G5-1 exhibited no ADCC activity on the human T cell lymphoma cell line HPB-ALL, whereas 6G5-P and 6G5-113F, to which a core fucose was not bound to the complex N-glycoside-linked sugar chain of the Fc region of the antibody, exhibited high ADCC activity. On the other hand, the ADCC activity of 6G5-P and 6G5-113F exhibited almost the same activity (FIG. 9A). These results are consistent with the results disclosed in U.S. Pat. No. 7,214,775 and Cancer Res 2008; 68: (10): 3863-72.

In addition, all of the anti-CD4 chimeric antibodies KM4045, KM4046, KM4047, KM4048 and KM4049 of the present invention exhibited a high ADCC activity equal to or higher than 6G5-P, on the human T cell lymphoma cell lines HUT78 and the human T cell lymphoblastic lymphoma cell line SUP-T1 (FIGS. 9B and C). Further, all of the anti-CD4 chimeric antibodies KM4045, KM4046, KM4048 and KM4049 exhibited a higher ADCC activity than 6G5-113F, on the human T cell lymphoma cell line HPB-ALL (FIG. 9D).

From these results, it was demonstrated that all of the anti-CD4 chimeric antibodies KM4045, KM4046, KM4047, KM4048 and KM4049 of the present invention exhibited high ADCC activity equal to or higher than the conventional anti-CD4 human antibody.

(4) Evaluation of Complement-Dependent Cellular Cytotoxicity (CDC Activity) of Anti-CD4 Chimeric Antibody on CD4 Transfectant and Human T Cell Lymphoma Cell Line The CDC activity of anti-CD4 chimeric antibodies KM4045 to KM4049 on the CD4 transfectant constructed in Example 1 and the human T cell lymphoma cell line HPB-ALL was measured in the same manner as in Example 4(3).

As a result, the conventional anti-CD4 human antibody 6G5-1 and the conventional anti-CD4 human antibody 6G5-113F having a 113F type Fc with a partial domain-exchange of Fc of IgG1 into Fc of IgG3 exhibited no CDC activity on the CD4 transfectant, whereas all of the anti-CD4 chimeric antibodies KM4045, KM4046, KM4047, KM4048 and KM4049 of the present invention exhibited a CDC activity (FIG. 10A). On the other hand, all the conventional anti-CD4 human antibody 6G5-113F having a 113F type Fc with a partial domain-exchange of Fc of IgG1 into Fc of IgG3, the conventional anti-CD4 mouse antibody OKT4, and the anti-CD4 chimeric antibodies KM4045 and KM4046 of the present invention exhibited no CDC activity on the human T cell lymphoma cell line HPB-ALL, and only the anti-CD4 chimeric antibody KM4049 of the present invention exhibited a CDC activity on the human T cell lymphoma cell line (FIG. 10B).

EXAMPLE 8

Preparation of Humanized Antibody (1) Design of Amino Acid Sequences of VH and VL of Anti-CD4 Humanized Antibody An amino acid sequence of VH of an anti-CD4 humanized antibody was designed in the following manner. Firstly, in order to graft the amino acid sequences of CDR1 to CDR3 of an anti-CD4 rat monoclonal antibody KM4065VH represented by SEQ ID NOs:27 to 29, respectively, the amino acid sequence of FR of VH of a human antibody was selected. Using a GCG Package (manufactured by Genetics Computer Group) as a sequence analysis system, a human antibody having a high homology with the anti-CD4 rat monoclonal antibody KM4065 was retrieved by the BLASTP method [*Nucleic Acids Res.*, 25, 3389 (1997)], based on the amino acid database of conventional proteins. When the homology score was compared with the homology of an actual amino acid sequence, SWISSPROT database accession no. AAC18328, Autoreactivity and immunoglobulin VH gene expression in aging humans (hereinafter, referred to as "AAC 18328") exhibited a homology of 84.2%. Since it was a human antibody which had the highest homology, the amino acid sequence of FR of this antibody was selected. With regard to the FR amino acid sequence of AAC 18328, it exhibited a deletion of one amino acid residue (the first residue) at the N-terminal of a secretory antibody reported by Kabat et al. [*Sequences of Proteins of Immunological Interest*, US Dept. Health and Human Services (1991)]. For the residue at the first position, Glu was selected which is an amino acid residue exhibited by the anti-CD4 rat monoclonal antibody KM4065. In addition, with regard to Val at the $11^{th}$ position, Val was substituted with Leu which is an amino acid residue appearing at a high frequency in the sequence of the human antibody and being exhibited in the anti-CD4 rat monoclonal antibody KM4065. Since these amino acid residues are found at a high frequency in any human antibody sequence [*Sequence of Proteins of Immunological Interest*, US Dept. Health and Human Service (1991)], they are not construed as being deviated from the human antibody sequence.

The amino acid sequences of CDRs of VH of the anti-CD4 rat monoclonal antibody KM4065 represented by SEQ ID NOs:27 to 29 were grafted into an appropriate position of the thus determined amino acid sequence of FR of the human antibody. In this manner, the amino acid sequence HV0 of VH of an anti-CD4 humanized antibody represented by SEQ ID NO:77 was designed.

Next, an amino acid sequence of VL of an anti-CD4 humanized antibody was designed in the following manner.

An amino acid sequence of FR of VL of a human antibody for grafting the amino acid sequences of CDR1 to CDR3 of an anti-CD4 rat monoclonal antibody KM4065VL represented by SEQ ID NOs:30 to 32, respectively, was selected. Kabat et al. have classified VL of conventionally known various human antibodies into four subgroups (HSG I to IV) based on the homology of their amino acid sequences and reported on the consensus sequences for each of the subgroups [*Sequences of Proteins of Immunological Interest*, US Dept. Health and Human Services (1991)]. Accordingly, the homology was examined between the amino acid sequence of FR of consensus sequences of subgroups I to IV of VL of the human antibody and the amino acid sequence of FR of VL of the anti-CD4 rat antibody KM4065.

As a result of retrieving the homology, the amino acid sequence of FR of KM4065VL had a high homology of 72.2% with HSGI. Based on these results, the amino acid sequence of CDR of VL of the anti-CD4 rat monoclonal antibody KM4065 was grafted into an appropriate position of an amino acid sequence of FR of the consensus sequence of subgroup I of VL of the human antibody. However, since Leu at position 24 and Leu at position 128 in the amino acid sequence of VL of the anti-CD4 rat monoclonal antibody KM4065 represented by SEQ ID NO:22 are not the amino acid residues having the highest use frequency in the region which corresponds to the amino acid sequence of the human antibody FR cited by Kabat et al., but are amino acid residues which are used at a relatively high frequency, the above-mentioned amino acid residues which are recognized in the amino acid sequence of the anti-CD4 rat monoclonal antibody KM4065 were used. In this manner, the amino acid sequence LV0 of VL of an anti-CD4 humanized antibody represented by SEQ ID NO:78 was designed.

The amino acid sequence HV0 of VH and the amino acid sequence LV0 of VL of the anti-CD4 humanized antibody designed in the above are sequences in which the CDR amino acid sequence of the anti-CD4 rat monoclonal antibody KM4065 alone was grafted into the selected human antibody FR amino acid sequence, but in general, when a humanized antibody is prepared, its binding activity is frequently lowered in the case of merely a simple grafting of a CDR amino acid sequence of a mouse antibody to a human antibody FR. For these reasons, in order to avoid decreasing of the binding activity, modifications of the amino acid residues considered to have an influence on the binding activity, among the FR amino acid residues which are different between human antibodies and mouse antibodies, are carried out together with the grafting of the CDR amino acid sequences. Thus, also in this example, the amino acid residues of FR considered to have an influence on the binding activity were identified in the following manner.

Firstly, a three-dimensional structure of an antibody V region (HV0LV0) consisting of the amino acid sequence HV0 of VH and the amino acid sequence LV0 of VL of the anti-CD4 humanized antibody designed in the above was constructed using a computer modeling technique. Preparation of the three dimensional structure coordinates was carried out using a software AbM (manufactured by Oxford Molecular) in accordance with instructions attached thereto, and display of the three-dimensional structure was carried out using a software Pro-Explore (manufactured by Oxford Molecular) or ViewerLite (manufactured by Accelrys) in accordance with instructions attached thereto. In addition, a computer model of the three-dimensional structure of the V region of the anti-CD4 rat monoclonal antibody KM4065 was also constructed in the same manner. Further, by similarly constructing a three-dimensional structure model consisting of an amino acid sequence in which the amino acid residues in the FR amino acid sequences of VH and VL of HV0LV0, which are different from those of the anti-CD4 rat antibody KM4065, were selected and modified into the amino acid residues of the anti-CD4 rat monoclonal antibody KM4065, three-dimensional structures of the V regions of the anti-CD4 rat monoclonal antibody KM4065, HV0LV0 and modified product were compared, whereby the amino acid residues predicted to have an influence on the binding activity of the antibody were identified.

As a result, as the amino acid residues among amino acid residues of FR of HV0LV0, which are considered to change a three-dimensional structure of the antigen binding region and therefore have an influence on the binding activity of the antibody, Leu at position 18, Val at position 93, Ala at position 97, and Thr at position 114 in the HV0 sequence, and Ala at position 13, Val at position 15, Val at position 19, Ala at position 47, Val at position 62, and Leu at position 82 in the LV0 sequence were respectively selected. By modifying at least one or more amino acid sequences of these selected amino acid residues into the amino acid residues which are present at the same positions of the amino acid sequence of the anti-CD4 rat monoclonal antibody KM4065, VH and VL of a humanized antibody having various modifications were designed. Specifically, regarding the antibody VH, at least one modification was introduced among the amino acid modifications for substituting Leu at position 18 with Met, Val at position 93 with Thr, Ala at position 97 with Thr, and Thr at position 114 with Ile in the amino acid sequence represented by SEQ ID NO:77. Further, regarding the antibody VL, at least one modification was introduced among the amino acid modifications for substituting Ala at position 13 with Val, Val at position 15 with Leu, Val at position 19 with Ala, Ala at position 47 with Gln, Val at position 62 with Ile, and Leu at position 82 with Val in the amino acid sequence represented by SEQ ID NO:78.

By designing amino acid sequences of variable regions of HV2LV0, HV3LV0, HV4LV0, and HV4LV6 with modifications of at least one of amino acid residues present in FR of HV0LV0, amino acid sequences of H chain variable regions HV2, HV3 and HV4, and L chain variable region LV6 are represented by SEQ ID NOs:96, 98, 100 and 102, respectively.

(2) Preparation and Evaluation of Anti-CD4 Humanized Antibody

A DNA encoding the amino acid sequence of the variable region of the anti-CD4 humanized antibody was constructed in mammalian cells using a codon which is used at a high frequency, when amino acid modification(s) are carried out using a codon which is used as a DNA encoding the amino acid sequence of VH or VL of the anti-CD4 rat monoclonal antibody KM4065. DNA sequences encoding the amino acid sequence of HV0 and LV0 of the anti-CD4 humanized antibody were represented by SEQ ID NOs:93 and 94, respectively, whereas DNA sequences encoding the amino acid sequences of variable regions HV2, HV3, HV4, and LV6 in which amino acid modification(s) were introduced were represented by SEQ ID NOs:95, 97, 99 and 101, respectively. Each DNA sequence was constructed by the complete synthesis. As in the same procedure described in Example 6, the complete synthesis DNA encoding each variable region was inserted into the humanized antibody expression vector pKANTEX93 to construct an anti-CD4 humanized antibody expression vector. The constructed anti-CD4 humanized antibody expression vector was introduced into an animal cell to express a humanized antibody, thereby preparing anti-CD4 humanized antibodies HV0LV0, HV2LV0, HV3LV0, HV4LV0 and HV4LV6.

When the binding activity of the obtained anti-CD4 humanized antibodies was measured using a Biacore T100, all of the prepared anti-CD4 humanized antibodies HV2LV0, HV3LV0, HV4LV0 and HV4LV6 exhibited a binding activity equal to or ½ or higher than that of the anti-CD4 chimeric antibody KM4045. Therefore, an anti-CD4 humanized antibody having a high binding activity was prepared.

EXAMPLE 9

Evaluation of Binding Activity of Humanized Antibody

The binding activity evaluation was carried out for the anti-CD4 humanized antibodies HV0LV0, HV2LV0, HV3LV0, HV4LV0 and HV4LV6 prepared according to the method described in Example 8.

(1) Biacore-Based Evaluation of Binding Activity of Anti-CD4 Humanized Antibody to Recombinant Human CD4

The measurement of a binding activity was carried out according to the method described in Example 7(2). The association rate constant ka, the dissociation rate constant kd and the dissociation constant $K_D$ (kd/ka) of respective antibodies thus obtained are shown in Table 6.

As a result, the humanized antibodies HV0LV0, HV2LV0, HV3LV0, HV4LV0, and HV4LV6 maintained a very strong binding activity of $1\times10^{-10}$M or higher. This is a binding activity equivalent to that of the chimeric antibody KM4045. And the binding activity is higher than that of 6G5-1.

TABLE 6

| Antibody | ka (1/Ms) | kd (1/s) | $K_D$ (M) |
| --- | --- | --- | --- |
| KM4045 | 5.41E+05 | <1E-05* | <1.84E-11* |
| HV0LV0 | 1.47E+06 | 2.86E-05 | 1.95E-11 |
| HV2LV0 | 1.14E+06 | <1E-05* | <8.77E-12* |
| HV3LV0 | 1.33E+06 | <1E-05* | <7.52E-12* |
| HV4LV0 | 7.91E+05 | <1E-05* | <1.26E-11* |
| LV4LV6 | 4.03E+05 | <1E-05* | <2.48E-11* |
| 6G5-1 | 5.34E+05 | 8.24E-04 | 1.54E-09 |

*Since KM4045, HV2LV0, HV3LV0, HV4LV0, and HV4LV6 exhibited slow dissociation, the value exceeds a measurable limit of a dissociation rate constant kd ($1 \times 10^{-5}$) indicated by the maker in this system.

(2) Evaluation of Binding Activity to CD4-Positive T Cell Lymphoma Cell Line Using Flow Cytometer Reactivity of various anti-CD4 antibodies to cells was evaluated. Chimeric antibody KM4045, humanized antibodies HV0LV0, HV2LV0, HV3LV0, HV4LV0 and HV4LV6, and human antibodies 6G5-1 and 6G5-P were used as the antibodies for evaluation.

Figure 11:
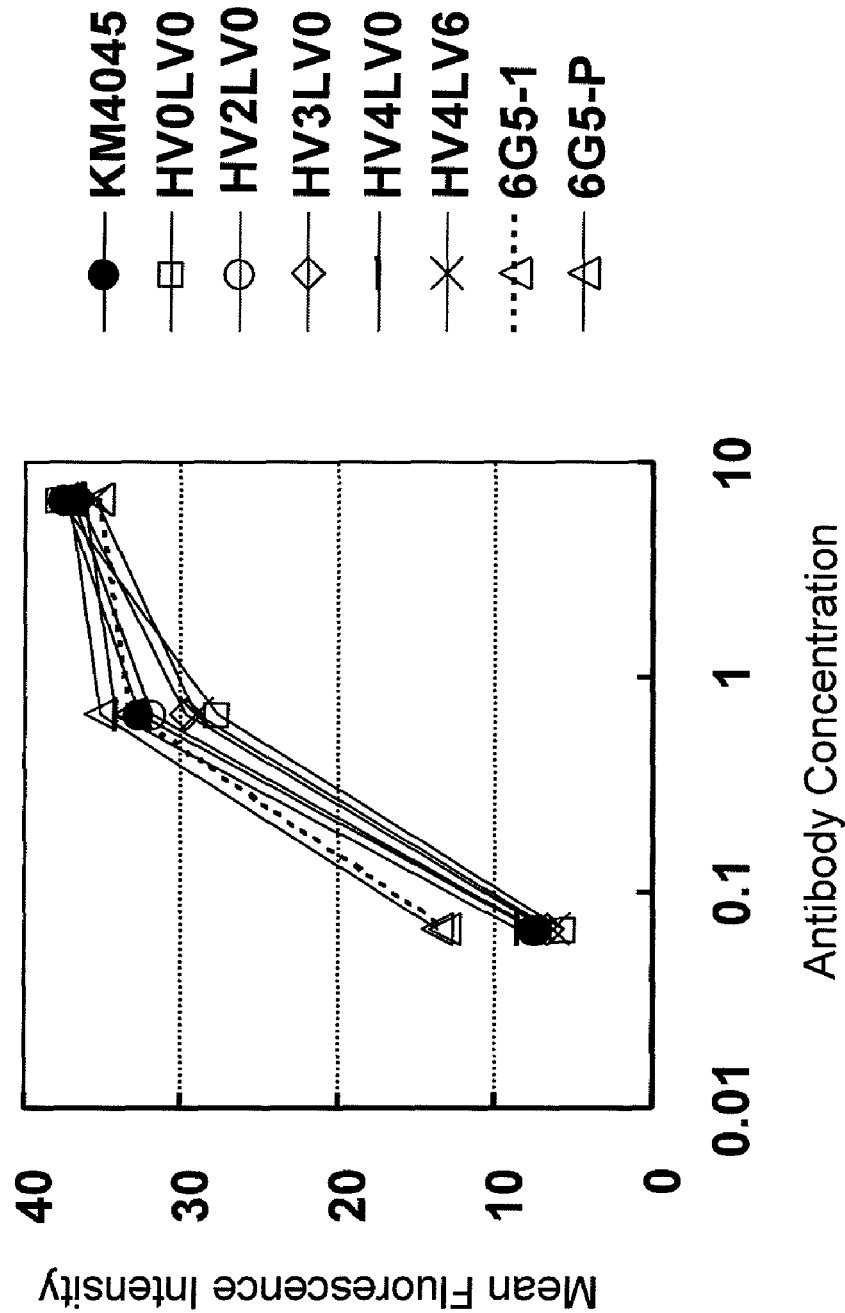
FIG. 11 shows the reactivity of various anti-CD4 antibodies for a CD4-positive T cell lymphoma cell line HPB-ALL in the use of a flow cytometer. The abscissa represents an antibody concentration (μg/mL), and the ordinate represents a mean fluorescence intensity, MFI value. ● represents a chimeric antibody KM4045, □ represents a humanized antibody HV0LV0, ○ represents a humanized antibody HV2LV0, ◇ represents a humanized antibody HV3LV0, – represents a humanized antibody HV4LV0, × represents a humanized antibody HV4LV6, Δ in the broken line represents a human antibody 6G5-1, and Δ in the solid line represents a human antibody 6G5-P.

In order to inhibit non-specific binding of a test antibody, a human IgG (manufactured by Sigma) at a final concentration of 1 mg/mL was added to 1 to $5\times10^5$ cells of the human T cell lymphoma cell line HPB-ALL. In addition, various anti-CD4 antibodies were appropriately diluted with BSA-PBS and added thereto to give a total volume of 50 μL. The resulting cell suspension was reacted on ice for 90 minutes, and washed two times with BSA-PBS. To the cells, 50 μL of an FITC-labeled anti-human IgG Fc antibody (manufactured by Acris) diluted with BSA-PBS was added, followed by reaction on ice for 90 minutes. The cells were washed once with BSA-PBS and then suspended in BSA-PBS. The fluorescence intensity was measured by a flow cytometer (manufactured by Beckman Coulter). FIG. 11 shows the mean fluorescence intensity (MFI value) when the antibody was reacted at a concentration of 6.7, 0.67 and 0.067 μg/mL. All of the anti-CD4 humanized antibodies bound to the CD4-positive cell line in an antibody concentration-dependent manner. Each of the binding degrees was equivalent to that of the chimeric antibody KM4045.

EXAMPLE 10

Evaluation of in Vitro Medicinal Efficacy of Humanized Antibody HV2LV0

The anti-CD4 humanized antibody HV2LV0 prepared in Example 8 is hereinafter referred to as KM8045. The antibody-dependent cellular cytotoxicity (ADCC activity) of the anti-CD4 humanized antibody on a human blood cancer cell line was evaluated according to the method described in Example 7(3). The target cell employed three types of cells, i.e., human T cell lymphoma cell lines HPB-ALL, HUT78, and CCRF-CEM. In addition, the antibody employed the humanized antibody KM8045, the chimeric antibody KM4045, and the human antibodies 6G5-1 and 6G5-P.

Figure 12:
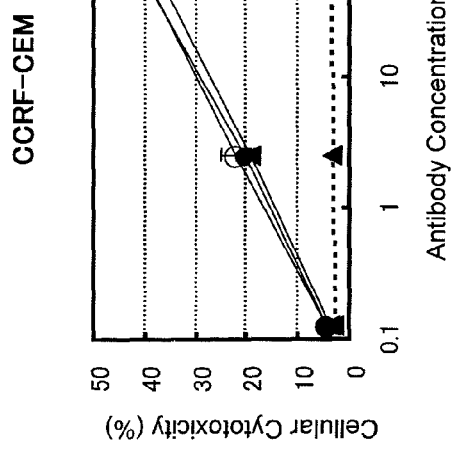
FIGS. 12(A) to 12(C) show an antibody-dependent cellular cytotoxicity (ADCC activity) of various anti-CD4 antibodies on various human T cell lymphoma lines. The ordinate represents a cellular cytotoxicity rate (%), and the abscissa represents an antibody concentration (ng/mL). ● represents a chimeric antibody KM4045, ○ represents a humanized antibody KM8045, ▲ in the broken line represents a human antibody 6G5-1, and ▲ in the solid line represents a human antibody 6G5-P.
Figure 12A:
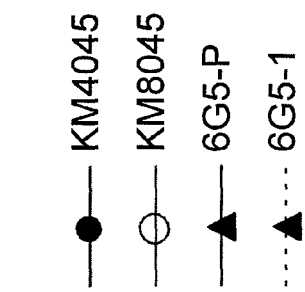
Figure 12A:
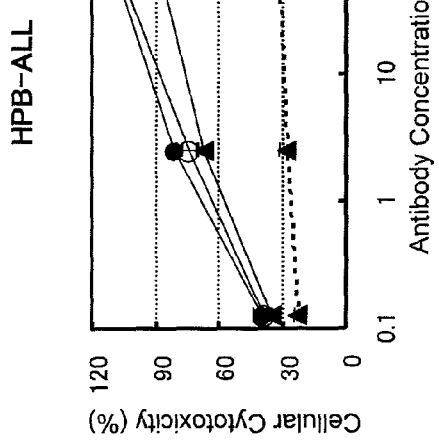
Figure 12:
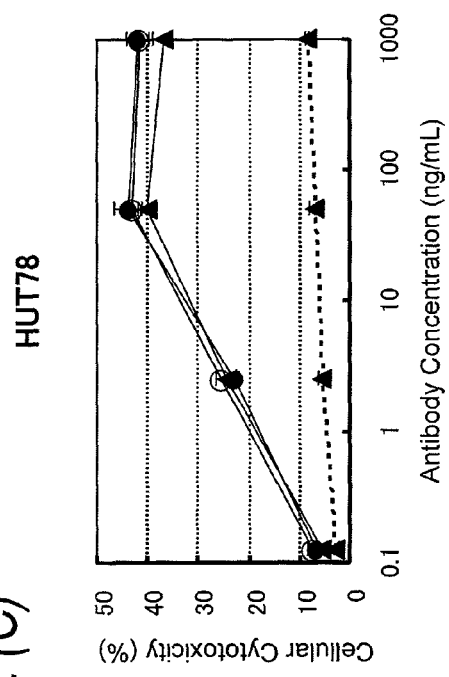

As a result, the humanized antibody KM8045 exhibited on any cell line, a high ADCC activity equivalent to that of the chimeric antibody KM4045, and also exhibited an ADCC activity equal to or higher than that of 6G5-P. 6G5-1 exhibited only a weak ADCC activity on HPB-ALL and HUT78, and exhibited no ADCC activity on CCRF-CEM (FIG. 12).

EXAMPLE 11

Evaluation of in Vivo Medicinal Efficacy of Humanized Antibody KM8045

(1) Mouse Early Stage Cancer Model Using Human T Cell Lymphoma Cell Line HH as Target The in vitro-cultured human T cell lymphoma cell line HH was suspended at a density of $1\times10^8$ cells/mL in RPMI1640 medium (Gibco BRL). Into the right abdominal of SCID mice (male, 8 weeks old, purchased from CLEA Japan), 100 μL ($1\times10^7$ cells/mouse) of the suspension was subcutaneously transplanted. The anti-CD4 humanized antibody KM8045 or anti-CD4 human antibody 6G5-P was diluted to give 1 μg/100 μL/head and intravenously administered to the mice on Days 0, 3, and 5, three times in total. A negative control group was given PBS alone. The day of tumor transplantation was taken as Day 0, and the diameter of tumor mass was measured day by day using vernier calipers. The tumor volume was calculated according to the following formula.

$$\text{tumor volume} = \text{breadth} \times \text{breadth} \times \text{length} \times 0.5$$

Figure 13:
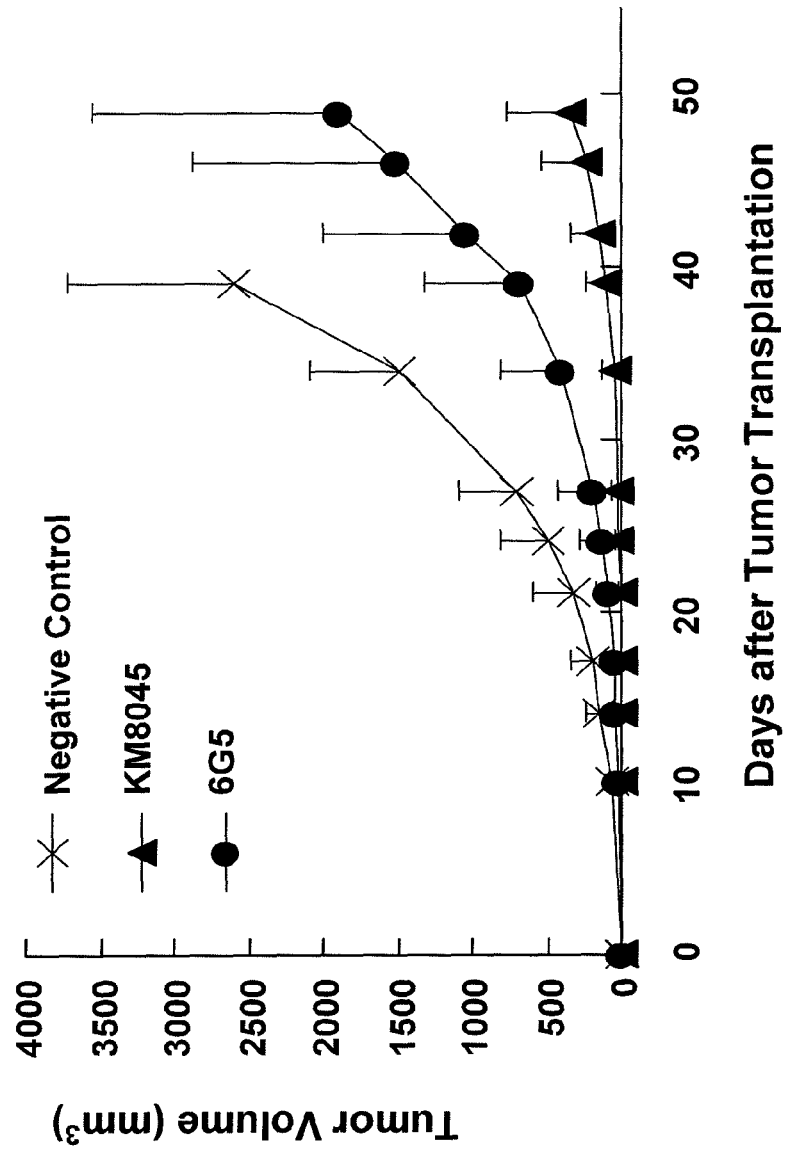
FIG. 13 shows anti-tumor effect (early stage cancer model) of each antibody on the human T cell lymphoma cell line HH which had been transplanted into a SCID mouse. The abscissa represents the number of days after tumor transplantation, and the ordinate represents a tumor volume. × represents a negative control group, ▲ represents a KM8045-administered group, and ● represents a 6G5-P-administered group. The bar represents a standard deviation.

Changes over days in a mean value of the tumor volume of each group are shown in FIG. 13. As shown in FIG. 13, the 6G5-P-administered group exhibited only weak anti-tumor effects as compared to the negative control group, whereas the KM8045-administered group exhibited significant anti-tumor effects.

From these results, it was demonstrated that the anti-CD4 humanized antibody KM8045 has higher anti-tumor effects than 6G5-P, on the mouse early stage cancer model in which an HH cell is used as a target.

(2) Mouse Metastasis Model Using CD4-Expressing EL4 as Target

CD4/EL4 constructed in Example 1(3) was cultured in vitro and suspended at a density of $1\times10^6$ cells/mL in RPMI1640 medium (Gibco BRL). Into the tail vein of C57BL/6 mice (male, 8 weeks old, purchased from CLEA Japan) was transplanted 100 μL/head ($1\times10^5$ cells/head) of the cell suspension. The day of tumor transplantation was defined as Day 0, and on Day 1. Each of anti-CD4 humanized antibody KM8045, and anti-CD4 human antibodies 6G5-P and 6G5-1 was prepared to be 0.2 μg/100 μL/head and 2 μg/100 μL/head, and then intravenously administered at a dose of 100 μL/head to the mice. The negative control group was given PBS alone, or an isotype control antibody. On Day 14, a body weight of all the mice was measured, and the mice were sacrificed by bleeding under ether anesthesia, followed by cervical dislocation. Thereafter, the liver and the kidney were collected and weighed. Then, a ratio of the liver weight and the kidney weight relative to the body weight of individual mice (hereinafter, referred to as "liver weight ratio" and "kidney weight ratio") was calculated as a percentage.

Figure 14A:
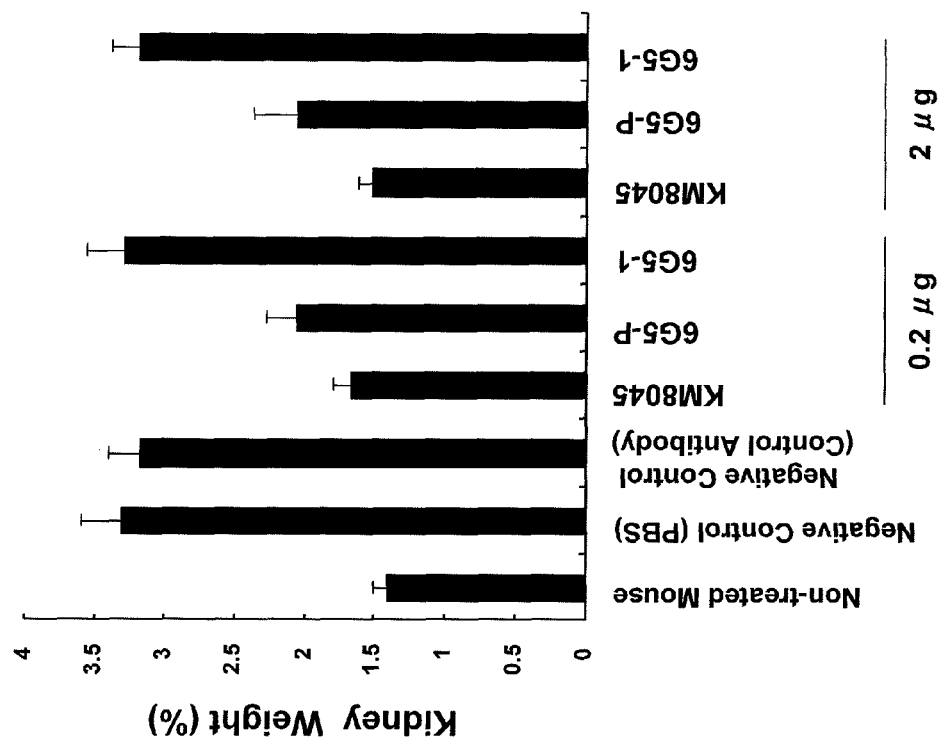
FIGS. 14(A) and 14(B) show anti-tumor effects (metastasis model) of individual antibodies on CD4/EL4 cells which had been transplanted into a C57BL/6 mouse.
Figure 14B:
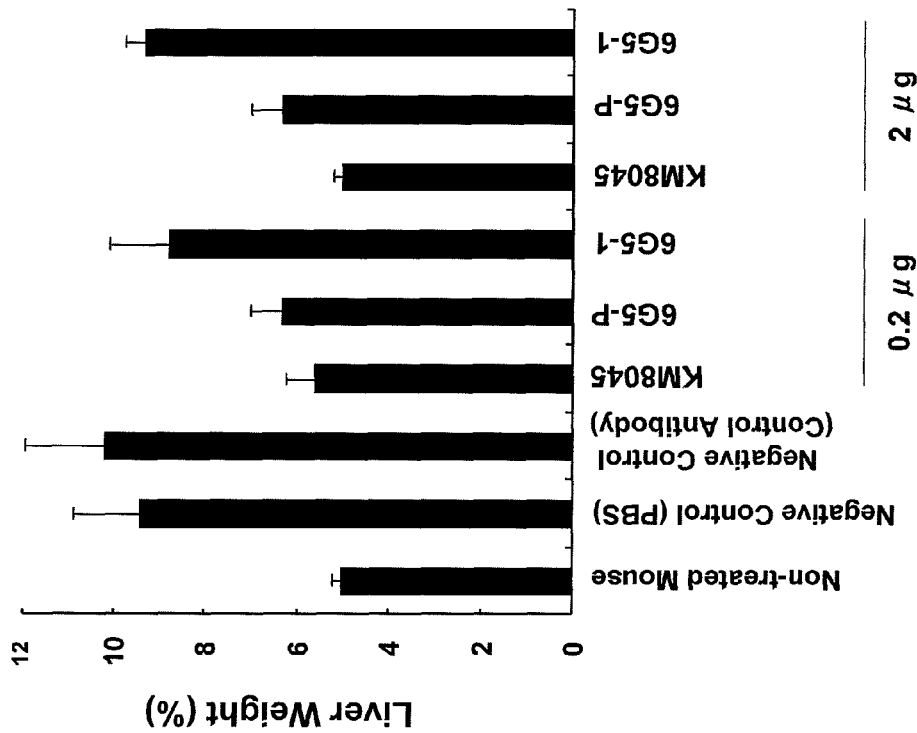

The evaluation of anti-tumor effects was carried out by comparing the liver and kidney weight ratio of each group which was increased due to the metastasis of tumor cells, with the liver and kidney weight ratio measured at the same time (mean value of three mice) of healthy mice which tumor had not been transplantated. The liver weight ratio and the kidney weight ratio of each group are shown in FIGS. 14A and 14B, respectively. As shown in FIGS. 14A and 14B, the 6G5-1-administered group exhibited no anti-tumor effects relative to the negative control group, whereas the 6G5-P-administered group and the KM8045-administered group exhibited anti-tumor effects. Further, more potent anti-tumor effects were recognized in the KM8045-administered group than in the 6G5-P-administered group.

From these results, it was demonstrated that KM8045 has higher anti-tumor effects than 6G5-1 and 6G5-P, on the mouse metastasis model when CD4/EL4 is used as a target.

(3) Mouse Progressive Cancer Model Using Human T Cell Lymphoma Cell Line HH as Target As with Example 11(3), the in vitro-cultured HH cell line was suspended at a density of $1\times10^8$ cells/mL in RPMI1640 medium (Gibco BRL). Into the right abdominal of SCID mice (male, 8 weeks old, purchased from CLEA Japan), 100 µL/head ($1\times10^7$ cells/head) of the suspension was subcutaneously transplanted. On Day 6 at which a tumor volume became an average of 60 mm$^3$, mice were grouped. The anti-CD4 humanized antibody KM8045 was diluted with PBS to give a dose of 20, 100, and 200 µg/100 µL/head, and intravenously administered to the mice twice a week, six times in total. The negative control group was administered PBS alone. The day of tumor transplantation was defined as Day 0, and the diameter of tumor mass was measured day by day using vernier calipers. The tumor volume was calculated according to the following formula.

Tumor Volume=Breadth×Breadth×Length×0.5

Figure 15:
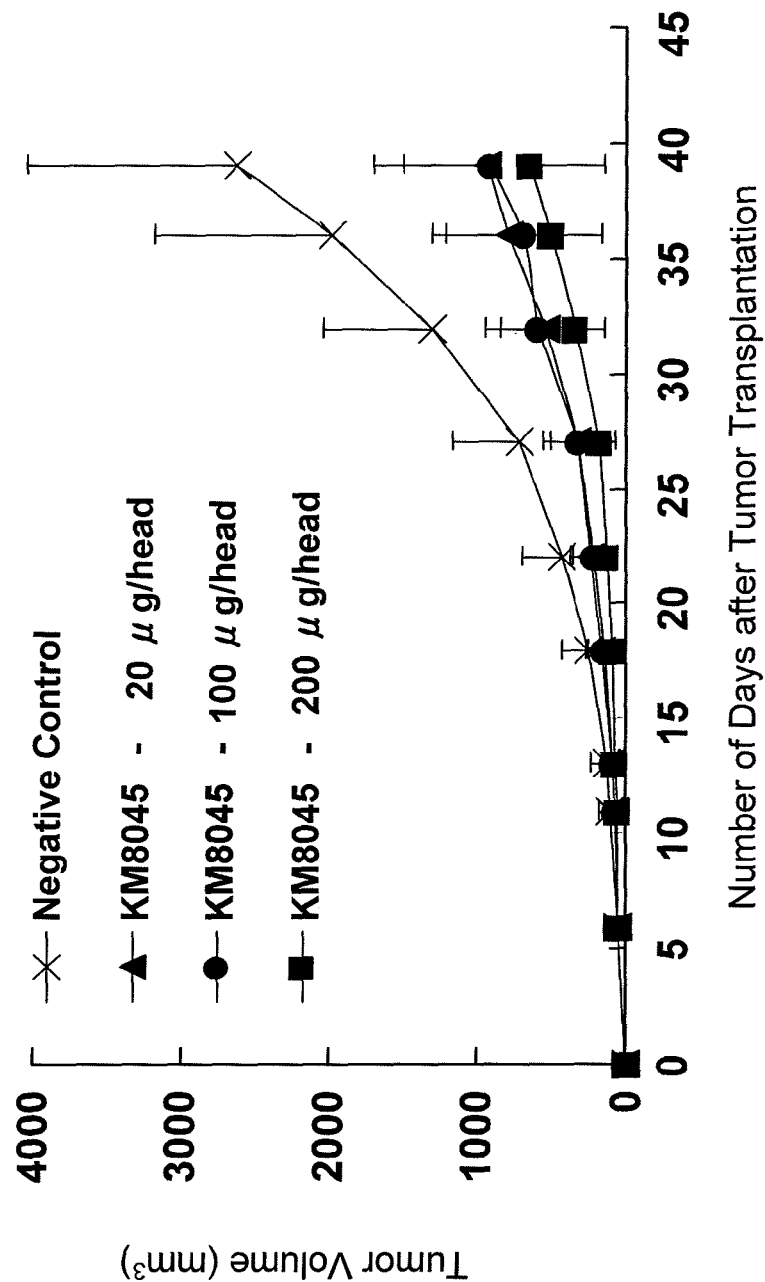
FIG. 15 shows anti-tumor effects (progressive cancer model) of each antibody on an HH cell line which had been transplanted into a SCID mouse. The abscissa represents the number of days after tumor transplantation, and the ordinate represents a tumor volume. × represents a negative control group, ▲ represents a group to which 20 μg/head of KM8045 was administered, ● represents a group to which 100 μg/head of KM8045 was administered, and ■ represents a group to which 200 μg/head of KM8045 was administered. The bar represents a standard deviation.

Changes over days in a mean value of the tumor volume of each group are shown in FIG. 15. As shown in FIG. 15, the KM8045-administered group exhibited anti-tumor effects. From the observation, that anti-tumor effect in the 200 µg/head group is higher than that in 20 µg/head and 100 µg/head groups, dose-dependent anti-tumor effects were confirmed.

From these results, it was demonstrated that the anti-CD4 humanized antibody KM8045 also had anti-tumor effects on the progressive cancer model in which an HH cell was used as a target.

While the invention has been described in detail and with reference to specific embodiments thereof, it will be apparent to one skill in the art that various changes and modifications can be made therein without departing from the spirit and scope thereof.

This application is based on Japanese application No. 2008-331904, filed on Dec. 26, 2008, and U.S. provisional application No. 61/141,393, filed on Dec. 30, 2008, the entire contents of which are incorporated hereinto by reference. All references cited herein are incorporated in their entirety.

What is claimed is:

1. A monoclonal antibody or antibody fragment thereof, wherein
said monoclonal antibody competes for binding to an extracellular region of CD4 with, and/or blinds to the same epitope in an extracellular regions of CD4 as, a reference antibody,
wherein said reference antibody comprises a heavy chain (H chain) and a light chain (L chain),
wherein complementarity determining regions (CDRs) 1 to 3 of said H chain comprise the amino acid sequences of SEQ ID NOs:51 to 53, respectively, and wherein CDRs 1 to 3 of said L chain comprise the amino acid sequences of SEQ ID NOs:54 to 56, respectively.

2. A monoclonal antibody or antibody fragment thereof, wherein
said monoclonal antibody competes for binding to an extracellular region of CD4 with, and/or binds to the same epitope in an extracellular region of CD4 as, a reference antibody,
wherein said reference antibody comprises a heavy chain (H chain) and a light chain (L chain),
wherein CDRs 1 to 3 of said H chain comprise the amino acid sequences of SEQ ID NOs:27 to 29, respectively, and wherein CDRs 1 to 3 of said L chain comprise the amino acid sequences of SEQ ID NOs:30 to 32, respectively.

3. A monoclonal antibody or antibody fragment thereof selected from the group consisting of (a) and (b):
(a) a monoclonal antibody or antibody fragment thereof comprising an H chain variable region (VH) and an L chain variable region (VL), wherein said VH and VL comprise the amino acid sequences of SEQ ID NOs:16 and 26, respectively, or wherein said VH and VL comprise the amino acid sequences of SEQ ID NOs:12 and 22, respectively; and
(b) a monoclonal antibody or antibody fragment thereof comprising a heavy chain (H chain) and a light chain (L chain), selected from the group consisting of (i) and (ii):
a monoclonal antibody or antibody fragment thereof in which CDRs 1 to 3 of said H chain comprise the amino acid sequences of SEQ ID NOs:51 to 53, respectively, and CDRs 1 to 3 of said L chain comprise the amino acid sequences of SEQ ID NOs:54 to 56, respectively, and;
(ii) a monoclonal antibody or antibody fragment thereof in which CDRs 1 to 3 of said H chain comprise the amino acid sequences of SEQ ID NOs:27 to 29, respectively, and CDRs 1 to 3 of said L chain comprise the amino acid sequences of SEQ ID NOs:30 to 32, respectively.

4. A monoclonal antibody or antibody fragment thereof, wherein said monoclonal antibody or antibody fragment thereof comprises an H chain variable region (VH) and an L chain variable region (VL), and wherein said monoclonal antibody or antibody fragment thereof is selected from the group consisting of (a)-(e):
(a) a humanized antibody in which said VH and VL comprise the amino acid sequences of SEQ ID NOs:77 and 78, respectively;
(b) a humanized antibody in which said VH and VL comprise the amino acid sequences of SEQ ID NOs:96 and 78, respectively;
(c) a humanized antibody in which said VH and VL comprise the amino acid sequences of SEQ ID NOs:98 and 78, respectively;
(d) a humanized antibody in which said VH and VL comprise the amino acid sequences of SEQ ID NOs:100 and 78, respectively; and
(e) a humanized antibody in which said VH and VL comprise the amino acid sequences of SEQ ID NOs:100 and 102, respectively.

5. The monoclonal antibody or antibody fragment thereof according to any one of claims 1, 2, 3, and 4, wherein the dissociation constant ($K_D$) for the antibody-antigen interaction of said monoclonal antibody or antibody fragment thereof is less than $1 \times 10^{-9}$ M, and wherein said monoclonal antibody or antibody fragment thereof exhibits high antibody-dependent cellular cytotoxicity (ADCC).

6. The monoclonal antibody or antibody fragment thereof according to claim 5, wherein said monoclonal or antibody fragment thereof exhibits high complement-dependent cellular cytotoxicity (CDC activity).

7. The monoclonal antibody or antibody fragment thereof according to claim 6, wherein said monoclonal antibody or antibody fragment exhibits CDC activity against a human cancer cell line expressing human CD4.

8. The monoclonal antibody or antibody fragment thereof according to any one of claims 1, 2, 3 and 4, wherein the monoclonal antibody is a recombinant antibody.

9. The monoclonal antibody or antibody fragment thereof according to claim 8, wherein the recombinant antibody is a recombinant antibody selected from the group consisting of a human chimeric antibody, a humanized antibody and a human antibody.

10. The monoclonal antibody or antibody fragment thereof according to any one of claims 1, 2, 3 and 4, wherein said antibody fragment is selected from the group consisting of a Fab, a Fab', a F(ab')$_2$, a single chain antibody (scFv), a dimerized V region (diabody), a disulfide stabilized V region (dsFv), and a peptide comprising CDR.

11. A pharmaceutical composition comprising the monoclonal antibody or antibody fragment thereof according to any one of claims 1, 2, 3, and 4, and a pharmaceutically acceptable carrier.

* * * * *